United States Patent
Juraszek et al.

(10) Patent No.: US 11,322,228 B2
(45) Date of Patent: May 3, 2022

(54) STRUCTURE BASED DESIGN OF D-PROTEIN LIGANDS

(71) Applicant: Janssen Vaccines & Prevention B.V., Leiden (NL)

(72) Inventors: Jaroslaw Juraszek, Amsterdam (NL); Davide Branduardi, London (GB); Ronald Vogels, Linschoten (NL); Robert Heinz Edward Friesen, Wassenaar (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 569 days.

(21) Appl. No.: 15/771,780

(22) PCT Filed: Oct. 27, 2016

(86) PCT No.: PCT/EP2016/075916
§ 371 (c)(1),
(2) Date: Apr. 27, 2018

(87) PCT Pub. No.: WO2017/072222
PCT Pub. Date: May 4, 2017

(65) Prior Publication Data
US 2020/0143911 A1   May 7, 2020

Related U.S. Application Data

(60) Provisional application No. 62/248,928, filed on Oct. 30, 2015.

(51) Int. Cl.
| | | |
|---|---|---|
| *G16C 20/50* | (2019.01) | |
| *G16C 20/20* | (2019.01) | |
| *G16C 20/30* | (2019.01) | |
| *G16B 20/50* | (2019.01) | |
| *G16C 20/62* | (2019.01) | |
| *G16C 20/70* | (2019.01) | |
| *G16B 15/30* | (2019.01) | |
| *C40B 30/04* | (2006.01) | |
| *G16B 20/30* | (2019.01) | |
| *C07K 1/107* | (2006.01) | |

(52) U.S. Cl.
CPC ............ *G16C 20/50* (2019.02); *C40B 30/04* (2013.01); *G16B 15/30* (2019.02); *G16B 20/30* (2019.02); *G16B 20/50* (2019.02); *G16C 20/20* (2019.02); *G16C 20/30* (2019.02); *G16C 20/62* (2019.02); *G16C 20/70* (2019.02); *C07K 1/107* (2013.01)

(58) Field of Classification Search
None
See application file for complete search history.

(56) References Cited

U.S. PATENT DOCUMENTS

| | | | |
|---|---|---|---|
| 2006/0110743 A1* | 5/2006 | Konishi | C07C 233/81 |
| | | | 435/6.12 |
| 2008/0305985 A1* | 12/2008 | Frank | C07K 14/00 |
| | | | 514/1.1 |
| 2011/0172981 A1* | 7/2011 | Al-Hashimi | G01R 33/465 |
| | | | 703/11 |
| 2013/0053541 A1 | 2/2013 | Shankar et al. | |
| 2015/0038408 A1 | 2/2015 | Baker et al. | |

FOREIGN PATENT DOCUMENTS

| | | | | |
|---|---|---|---|---|
| WO | 199735194 A2 | 9/1997 | | |
| WO | 2012078313 A2 | 6/2012 | | |
| WO | 2013138259 | * | 9/2013 | ............ A61K 38/00 |
| WO | 2013138259 A2 | 9/2013 | | |

OTHER PUBLICATIONS

Tlatli et al. FEBS Journal, 280, 2013,139-159.*
Marco et al. ChemMedChem (2007), 2(10), 1388-1401.*
Rongan et al. Perspectives in Drug Discovery and Design, Sep. 10, 2011, 181-209, 1998.*
Sievers et al., Structure-based design of non-natural amino-acid inhibitors of amyloid fibril formation, Nature, vol. 475, pp. 96-100.
Haupt et al., Biotechnologically engineered protein binders for applications in amyloid diseases; Trends in Biotechnology, vol. 32, No. 10, pp. 513-520, Aug. 26, 2014.
Int'l Search Report and Written Opinion dated Mar. 22, 2018 in int'l Application No. PCT/EP2016/075916.

* cited by examiner

Primary Examiner — Michael L Borin
(74) Attorney, Agent, or Firm — Ice Miller LLP

(57) ABSTRACT

A method of designing a D-polypeptide that binds with an L-target protein can include: identifying a polypeptide target having L-chirality; determining hotspot amino acids of a polypeptide ligand having L-chirality that have binding interactions with the L-target protein; determining transformations of side chains of the hotspot amino acids that retain the binding interactions with the target; generating inversed hotspot amino acids with chirality opposite to the one of the target; identifying a polypeptide having inverse chirality from the target protein, on which a combination of inversed hotspot amino-acid can be grafted without significantly changing their interactions with the target. The designed ligands can be processed and converted to D-ligands that bind with the L-target protein.

31 Claims, 27 Drawing Sheets
Specification includes a Sequence Listing.

Fig. 23

SEQUENCE LISTING

<160> NUMBER OF SEQ ID NOS: 27

<210> SEQ ID NO 1
<211> LENGTH: 35
<212> TYPE: PRT
<213> ORGANISM: Artificial Sequence
<220> FEATURE:
<223> OTHER INFORMATION: DP141050

<400> SEQUENCE: 1

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 2
<211> LENGTH: 35
<212> TYPE: PRT
<213> ORGANISM: Artificial Sequence
<220> FEATURE:
<223> OTHER INFORMATION: DP141071

<400> SEQUENCE: 2

Arg Ser Cys Ile Ala Thr Phe Pro Lys Ser Phe Cys Thr Ala Phe Leu
1               5                   10                  15

Cys Lys His Leu Met Lys Ala Arg Leu Ser Tyr Cys Arg Lys Thr Cys
            20                  25                  30

Gly Thr Cys
        35

<210> SEQ ID NO 3
<211> LENGTH: 35
<212> TYPE: PRT
<213> ORGANISM: Artificial Sequence
<220> FEATURE:
<223> OTHER INFORMATION: DP141090

<400> SEQUENCE: 3

Arg Ser Cys Ile Ala Thr Phe Pro Lys Tyr Phe Cys Thr Ala Phe Leu
1               5                   10                  15

Cys Lys His Leu Met Lys Ala Arg Leu Ser Tyr Cys Arg Lys Thr Cys
            20                  25                  30

Gly Thr Cys
        35

<210> SEQ ID NO 4
<211> LENGTH: 35
<212> TYPE: PRT
<213> ORGANISM: Artificial Sequence
<220> FEATURE:
<223> OTHER INFORMATION: DP141087

<400> SEQUENCE: 4

Arg Ser Cys Ile Ala Thr Phe Pro Lys Tyr Phe Cys Thr Ala Phe Leu
1               5                   10                  15

Cys Lys His Leu Met Lys Ala Arg Leu Ser Phe Cys Arg Lys Thr Cys
            20                  25                  30

Gly Thr Cys
        35

```
<210> SEQ ID NO 5
<211> LENGTH: 35
<212> TYPE: PRT
<213> ORGANISM: Artificial Sequence
<220> FEATURE:
<223> OTHER INFORMATION: DP141072

<400> SEQUENCE: 5

Arg Ser Cys Gln Ala Thr Phe Pro Lys Ser Phe Cys Thr Ala Phe Leu
1               5                   10                  15

Cys Lys His Leu Met Lys Ala Arg Leu Ser Tyr Cys Arg Lys Thr Cys
            20                  25                  30

Gly Thr Cys
        35

<210> SEQ ID NO 6
<211> LENGTH: 35
<212> TYPE: PRT
<213> ORGANISM: Artificial Sequence
<220> FEATURE:
<223> OTHER INFORMATION: DP141092

<400> SEQUENCE: 6

Arg Ser Cys Ile Ala Ala Phe Pro Lys Tyr Phe Cys Thr Ala Phe Leu
1               5                   10                  15

Cys Lys His Leu Met Lys Ala Arg Leu Ser Tyr Cys Arg Lys Thr Cys
            20                  25                  30

Gly Thr Cys
        35

<210> SEQ ID NO 7
<211> LENGTH: 35
<212> TYPE: PRT
<213> ORGANISM: Artificial Sequence
<220> FEATURE:
<223> OTHER INFORMATION: DP141080

<400> SEQUENCE: 7

Arg Ser Cys Ile Ala Ala Phe Pro Lys Ser Phe Cys Thr Ala Phe Leu
1               5                   10                  15

Cys Lys His Leu Met Lys Ala Arg Leu Ser Tyr Cys Arg Leu Thr Cys
            20                  25                  30

Gly Thr Cys
        35

<210> SEQ ID NO 8
<211> LENGTH: 35
<212> TYPE: PRT
<213> ORGANISM: Artificial Sequence
<220> FEATURE:
<223> OTHER INFORMATION: DP141073

<400> SEQUENCE: 8

Arg Ser Cys Ile Ala Ala Phe Pro Lys Ser Phe Cys Thr Ala Phe Leu
1               5                   10                  15

Cys Lys His Leu Met Lys Ala Arg Leu Ser Tyr Cys Arg Lys Thr Cys
            20                  25                  30

Gly Thr Cys
        35

<210> SEQ ID NO 9
<211> LENGTH: 35
<212> TYPE: PRT
```

<213> ORGANISM: Artificial Sequence
<220> FEATURE:
<223> OTHER INFORMATION: DP141094

<400> SEQUENCE: 9

Arg Ser Cys Ile Ala Thr Phe Pro Lys Tyr Phe Cys Thr Ala Phe Leu
1               5                   10                  15

Cys Lys His Leu Met Lys Ala Arg Leu Ser Tyr Cys Arg Leu Thr Cys
            20                  25                  30

Gly Thr Cys
        35

<210> SEQ ID NO 10
<211> LENGTH: 35
<212> TYPE: PRT
<213> ORGANISM: Artificial Sequence
<220> FEATURE:
<223> OTHER INFORMATION: DP141088

<400> SEQUENCE: 10

Arg Ser Cys Gln Ala Thr Phe Pro Lys Tyr Phe Cys Thr Ala Phe Leu
1               5                   10                  15

Cys Lys His Leu Met Lys Ala Arg Leu Ser Phe Cys Arg Lys Thr Cys
            20                  25                  30

Gly Thr Cys
        35

<210> SEQ ID NO 11
<211> LENGTH: 35
<212> TYPE: PRT
<213> ORGANISM: Artificial Sequence
<220> FEATURE:
<223> OTHER INFORMATION: DP141063

<400> SEQUENCE: 11

Arg Ser Cys Ile Ala Thr Glu Pro Lys Ser Phe Cys Thr Ala Phe Leu
1               5                   10                  15

Cys Lys His Leu Met Lys Ala Arg Leu Ser Tyr Cys Arg Lys Thr Cys
            20                  25                  30

Gly Thr Cys
        35

<210> SEQ ID NO 12
<211> LENGTH: 35
<212> TYPE: PRT
<213> ORGANISM: Artificial Sequence
<220> FEATURE:
<223> OTHER INFORMATION: DP141065

<400> SEQUENCE: 12

Arg Ser Cys Gln Ala Thr Glu Pro Lys Tyr Phe Cys Thr Ala Phe Leu
1               5                   10                  15

Cys Lys His Leu Met Lys Ala Arg Leu Ser Tyr Cys Arg Lys Thr Cys
            20                  25                  30

Gly Thr Cys
        35

<210> SEQ ID NO 13
<211> LENGTH: 35
<212> TYPE: PRT
<213> ORGANISM: Artificial Sequence
<220> FEATURE:
<223> OTHER INFORMATION: DP142130

-continued

```
<400> SEQUENCE: 13

Arg Ser Cys Gln Ala Thr Phe Pro Lys Leu Phe Cys Thr Ala Phe Leu
1               5                   10                  15

Cys Lys His Leu Met Lys Ala Arg Leu Ser Tyr Cys Arg Lys Thr Cys
            20                  25                  30

Gly Thr Cys
        35

<210> SEQ ID NO 14
<211> LENGTH: 35
<212> TYPE: PRT
<213> ORGANISM: Artificial Sequence
<220> FEATURE:
<223> OTHER INFORMATION: DP142131
<220> FEATURE:
<221> NAME/KEY: MISC_FEATURE
<222> LOCATION: (27)..(27)
<223> OTHER INFORMATION: x=3-naphtyl-D-alanine

<400> SEQUENCE: 14

Arg Ser Cys Gln Ala Thr Phe Pro Lys Ser Phe Cys Thr Ala Phe Leu
1               5                   10                  15

Cys Lys His Leu Met Lys Ala Arg Leu Ser Xaa Cys Arg Lys Thr Cys
            20                  25                  30

Gly Thr Cys
        35

<210> SEQ ID NO 15
<211> LENGTH: 35
<212> TYPE: PRT
<213> ORGANISM: Artificial Sequence
<220> FEATURE:
<223> OTHER INFORMATION: DP142133

<400> SEQUENCE: 15

Arg Ser Cys Gln Ala Thr Phe Pro Lys Ser Phe Cys Thr Ala Phe Leu
1               5                   10                  15

Cys Lys His Leu Met Lys Ala Arg Leu Ser Asn Cys Arg Lys Thr Cys
            20                  25                  30

Gly Thr Cys
        35

<210> SEQ ID NO 16
<211> LENGTH: 35
<212> TYPE: PRT
<213> ORGANISM: Artificial Sequence
<220> FEATURE:
<223> OTHER INFORMATION: DP142134

<400> SEQUENCE: 16

Arg Ser Cys Gln Ala Thr Phe Pro Lys Ser Phe Cys Thr Ala Phe Leu
1               5                   10                  15

Cys Lys His Leu Met Lys Ser Arg Leu Ser Tyr Cys Arg Lys Thr Cys
            20                  25                  30

Gly Thr Cys
        35

<210> SEQ ID NO 17
<211> LENGTH: 35
<212> TYPE: PRT
<213> ORGANISM: Artificial Sequence
<220> FEATURE:
```

<223> OTHER INFORMATION: DP142135
<220> FEATURE:
<221> NAME/KEY: MISC_FEATURE
<222> LOCATION: (23)..(23)
<223> OTHER INFORMATION: x=D-norleucine

<400> SEQUENCE: 17

Arg Ser Cys Gln Ala Thr Phe Pro Lys Ser Phe Cys Thr Ala Phe Leu
1               5                   10                  15

Cys Lys His Leu Met Lys Xaa Arg Leu Ser Tyr Cys Lys Thr Cys
            20                  25                  30

Gly Thr Cys
        35

<210> SEQ ID NO 18
<211> LENGTH: 35
<212> TYPE: PRT
<213> ORGANISM: Artificial Sequence
<220> FEATURE:
<223> OTHER INFORMATION: DP142136
<220> FEATURE:
<221> NAME/KEY: MISC_FEATURE
<222> LOCATION: (23)..(23)
<223> OTHER INFORMATION: x=D-norleucine

<400> SEQUENCE: 18

Arg Ser Cys Gln Ala Thr Phe Pro Lys Leu Phe Cys Thr Ala Phe Leu
1               5                   10                  15

Cys Lys His Leu Met Lys Xaa Arg Leu Ser Tyr Cys Arg Lys Thr Cys
            20                  25                  30

Gly Thr Cys
        35

<210> SEQ ID NO 19
<211> LENGTH: 35
<212> TYPE: PRT
<213> ORGANISM: Artificial Sequence
<220> FEATURE:
<223> OTHER INFORMATION: DP142137
<220> FEATURE:
<221> NAME/KEY: MISC_FEATURE
<222> LOCATION: (23)..(23)
<223> OTHER INFORMATION: x=D-norleucine
<220> FEATURE:
<221> NAME/KEY: MISC_FEATURE
<222> LOCATION: (27)..(27)
<223> OTHER INFORMATION: x=3-naphtyl-D-alanine

<400> SEQUENCE: 19

Arg Ser Cys Gln Ala Thr Phe Pro Lys Leu Phe Cys Thr Ala Phe Leu
1               5                   10                  15

Cys Lys His Leu Met Lys Xaa Arg Leu Ser Xaa Cys Arg Lys Thr Cys
            20                  25                  30

Gly Thr Cys
        35

<210> SEQ ID NO 20
<211> LENGTH: 29
<212> TYPE: PRT
<213> ORGANISM: Artificial Sequence
<220> FEATURE:
<223> OTHER INFORMATION: DP142093
<220> FEATURE:
<221> NAME/KEY: MISC_FEATURE
<222> LOCATION: (19)..(19)
<223> OTHER INFORMATION: x=D-homophenylalanine

```
<400> SEQUENCE: 20

Arg Phe Cys Pro Ser Ile Asx Lys Lys Cys Arg Arg Asp Ser Asp Cys
1               5                   10                  15

Pro Gly Xaa Cys Ile Cys Lys Gly Asn Gly Tyr Cys Gly
            20                  25

<210> SEQ ID NO 21
<211> LENGTH: 29
<212> TYPE: PRT
<213> ORGANISM: Artificial Sequence
<220> FEATURE:
<223> OTHER INFORMATION: DP141747
<220> FEATURE:
<221> NAME/KEY: MISC_FEATURE
<222> LOCATION: (19)..(19)
<223> OTHER INFORMATION: x=D-homophenylalanine

<400> SEQUENCE: 21

Arg Phe Cys Pro Asn Ile Leu Lys Lys Cys Arg Arg Asp Ser Asp Cys
1               5                   10                  15

Pro Gly Xaa Cys Ile Cys Lys Gly Asn Gly Tyr Cys Gly
            20                  25

<210> SEQ ID NO 22
<211> LENGTH: 29
<212> TYPE: PRT
<213> ORGANISM: Artificial Sequence
<220> FEATURE:
<223> OTHER INFORMATION: DP141748

<400> SEQUENCE: 22

Arg Phe Cys Pro Asn Ile Leu Lys Lys Cys Arg Arg Asp Ser Asp Cys
1               5                   10                  15

Pro Gly Glu Cys Ile Cys Lys Gly Asn Gly Tyr Cys Gly
            20                  25

<210> SEQ ID NO 23
<211> LENGTH: 29
<212> TYPE: PRT
<213> ORGANISM: Artificial Sequence
<220> FEATURE:
<223> OTHER INFORMATION: DP141749
<220> FEATURE:
<221> NAME/KEY: MISC_FEATURE
<222> LOCATION: (19)..(19)
<223> OTHER INFORMATION: X=D-homophenylalanine

<400> SEQUENCE: 23

Arg Phe Cys Pro Ser Ile Leu Lys Lys Cys Arg Arg Asp Ser Asp Cys
1               5                   10                  15

Pro Gly Xaa Cys Ile Cys Lys Gly Asn Gly Tyr Cys Gly
            20                  25

<210> SEQ ID NO 24
<211> LENGTH: 29
<212> TYPE: PRT
<213> ORGANISM: Artificial Sequence
<220> FEATURE:
<223> OTHER INFORMATION: DP141750

<400> SEQUENCE: 24

Arg Phe Cys Pro Ser Ile Leu Lys Lys Cys Arg Arg Asp Ser Asp Cys
1               5                   10                  15

Pro Gly Glu Cys Ile Cys Lys Gly Asn Gly Tyr Cys Gly
            20                  25
```

```
<210> SEQ ID NO 25
<211> LENGTH: 29
<212> TYPE: PRT
<213> ORGANISM: Artificial Sequence
<220> FEATURE:
<223> OTHER INFORMATION: DP141751
<220> FEATURE:
<221> NAME/KEY: MISC_FEATURE
<222> LOCATION: (7)..(7)
<223> OTHER INFORMATION: x=D-homoleucine
<220> FEATURE:
<221> NAME/KEY: MISC_FEATURE
<222> LOCATION: (19)..(19)
<223> OTHER INFORMATION: x=D-homophenylalanine

<400> SEQUENCE: 25

Arg Phe Cys Pro Ser Ile Xaa Lys Lys Cys Arg Arg Asp Ser Asp Cys
1               5                   10                  15

Pro Gly Xaa Cys Ile Cys Lys Gly Asn Gly Tyr Cys Gly
            20                  25

<210> SEQ ID NO 26
<211> LENGTH: 29
<212> TYPE: PRT
<213> ORGANISM: Artificial Sequence
<220> FEATURE:
<223> OTHER INFORMATION: DP141752
<220> FEATURE:
<221> NAME/KEY: MISC_FEATURE
<222> LOCATION: (7)..(7)
<223> OTHER INFORMATION: x=for D-homoleucine

<400> SEQUENCE: 26

Arg Phe Cys Pro Ser Ile Xaa Lys Lys Cys Arg Arg Asp Ser Asp Cys
1               5                   10                  15

Pro Gly Glu Cys Ile Cys Lys Gly Asn Gly Tyr Cys Gly
            20                  25

<210> SEQ ID NO 27
<211> LENGTH: 29
<212> TYPE: PRT
<213> ORGANISM: Artificial Sequence
<220> FEATURE:
<223> OTHER INFORMATION: DP141753

<400> SEQUENCE: 27

Arg Ala Cys Pro Arg Ile Leu Lys Lys Cys Arg Arg Asp Ser Asp Cys
1               5                   10                  15

Pro Gly Glu Cys Ile Cys Lys Gly Asn Gly Tyr Cys Gly
            20                  25
```

STRUCTURE BASED DESIGN OF D-PROTEIN LIGANDS

CROSS-REFERENCE TO RELATED APPLICATION

This application is a Section 371 of International Application No. PCT/EP2016/075916, filed Oct. 27, 2016, which was published in the English language on May 4, 2017 under International Publication No. WO 2017/072222 A1, and claims priority under 35 U.S.C. § 119(b) to Provisional Application No. 62/248,928, filed Oct. 30, 2015, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 688097_476US", creation date of Apr. 27, 2018, and having a size of 11.4 KB. The sequence listing submitted via EFS-Web is part of the specification and is herein incorporated by reference in its entirety.

FIELD OF THE INVENTION

The present invention relates to the field of design of synthetic proteins and polypeptides capable of binding to a target protein, and more particularly to design of synthetic proteins and polypeptides that include D-amino acids that bind to target proteins that include L-amino acids. The present invention further relates to the computing methods of designing and selecting the proteins and polypeptides and computing methods of optimizing the binding interaction between the designer proteins and polypeptides and the target protein. In addition, the present invention relates to the use of such designer proteins as prophylactic, therapeutic, or diagnostic agents.

BACKGROUND

Many prophylactic and therapeutic agents somehow interfere with the activity of molecules that play a role in disease or homeostasis. This interference involves binding of the agent to a target molecule, which binding results in regulation (e.g. inhibition or activation) of the function of that particular target molecule and/or of (e.g., one of) the molecules with which the target molecule interacts. Said target molecule, as non-limiting examples, can be a polypeptide, protein, nucleic acid, lipid or glycan and can be situated inside and/or outside of a cell. The prophylactic or therapeutic agent, often referred to as ligand, can be, as non-limiting examples, a small molecule drug, peptide (e.g. linear, cyclic, 'stapled', 'clipsed'), polypeptide, protein, nucleic acid (e.g. single stranded or double stranded RNA or DNA) or combinations of these. Well known examples of such prophylactic or therapeutic agents applied to prevent and/or treat many different diseases are, as non-limiting examples, chemical drugs, hormones, cytokines and antibodies. Hormones and cytokines generally bind to a receptor and evoke an activating or inhibiting signal. Antibodies and other proteins can do the same or can bind other molecules (e.g., other proteins) thereby influencing the activity of that molecule. Each of the above mentioned classes of agents has proven potency and advantages and disadvantages that make them particular suitable for a specific treatment or disease area. For example, small molecule drugs are, in part due to their small size, more often orally available and/or capable of penetrating cell membranes than large proteins (e.g. antibodies) are. Other advantages are the high stability and absence of immunogenicity. Furthermore, small molecule drugs are cheaper to produce than large proteins making it possible to compensate the short half-life by daily administration. The downside of small molecule drugs is that, also in part due to their small size, the binding to the target is less specific resulting in off-target binding and toxicity. Often, this limits prophylactic, but also the therapeutic use of chemical drugs.

Antibodies binding to proteins but also protein-protein interactions (PPI) generally have much larger surfaces available for the binding interaction which results in higher specificity and much less off-target binding and related toxicity. Also, due to the different size, the binding region of these classes of agents is very different from small molecules. Typically, larger interaction regions allow binding to flat surfaces whereas the small size of chemicals dictates interactions in a deeper pocket or groove. Furthermore, proteins, antibodies in particular, have a longer half-life, which often can even be extended by manipulation. All this has the consequence that in many cases the targets of small molecules and proteins as well as mechanism of action are different. Furthermore, as opposed to small molecules, antibodies and other proteins are sensitive to proteolytic cleavage and may be immunogenic. This reduces bio-availability and half-life as well as the opportunity of long term repeated administration. In summary, small molecules are in general cheap to produce, very stable, non-immunogenic, oral/intracellular available, need a cavity or relatively deep groove for binding, have a short half-life and show more off-target toxicity. Proteins (including antibodies) on the other hand are more costly to produce, less capable to penetrate cells, sensitive to proteolysis, potentially immunogenic, but capable of binding relatively flat surfaces and they show much less off-target toxicity.

This clear separation has the consequence that some targets are unfavorable for both classes of agents. Therefore, there is a clear need for a new class of molecules that combines the advantages of both small molecules and antibodies into one molecule. Such a molecule should have a high specificity, low toxicity and should be also very stable, resistant to proteolytic cleavage, non-immunogenic and cheap to produce. This application discloses methods and means to design synthetic polypeptides and proteins that are predicted to have the characteristics of such a molecule.

Typically, most organisms produce proteins from L-amino acids, where the "L" designates that the amino acids are L-isomers, which are characterized by being left-handed isomers. However, some microorganisms can produce D-amino acids, which are D-isomers that are characterized as being right-handed isomers. Most amino acids are chiral molecules that can have multiple isomers, where the L-isomers and D-isomers are mirror images of each other, and thereby L- and D-isomers structures cannot be superimposed onto each other. The chirality arises primarily from the absolute configuration at the carbon atom Cα that is connected to the carboxyl, amino, and side-chain groups of the amino acids. Under standard conditions the two arrangements cannot be interchanged into each other, and therefore they correspond to two distinct chemical entities, presenting different chemo-physical properties. Proteins that are built of D-amino acids are not recognized by L-isomer peptidases making them resistant to proteolytic breakdown. This lack of cleavage results in a longer half-life in vivo and makes the immune system relatively blind to proteins that are fully made of D-amino acids (D-proteins) likely at least in part due to absence of peptide presentation in MHC class I and II surface proteins. Thus, an improved class of binding proteins consists fully of D-amino acids and combines high binding specificity and low toxicity with high stability and lack of immunogenicity. Such proteins can be designed to bind and activate or repress receptor proteins, to bind to other proteins and interfere with their function or to bind to one of the participating proteins in a protein-protein interaction, thereby interfering with an extracellular or intracellular process. In addition, such proteins can be designed to bind nucleic acids, lipids or glycan molecules thereby also interfering with an extra- or intracellular process. However, polypeptides and proteins having D-amino acids are not easily made by existing biological protein production systems. They can be made by current readily available protein synthesis methods by anyone skilled in the art, but the length of the full D-amino acid protein can be prohibitive to synthesis. The challenge therefore is to select the right protein sequences to synthesize.

One method of screening for a polypeptide or protein having D-amino acids is described in patent WO1997035194 A3 or WO2012078313 A2, wherein mirror-imaged phage display and applications are presented. In brief, this method entails synthesis of the target L-protein with D-amino acids, resulting in an exact mirror image structure of the target. In the next step, a library of small scaffold proteins (e.g., L-scaffold) having L-amino acids is used to find and optimize L-ligands binding to the D-target proteins. The selected L-ligands are then converted to the corresponding D-ligands having D-amino acids sequences, which then are capable of binding to the natural L-amino acid version of the L-target. This method requires correct synthesis and folding of the target molecule in the D-target format, a step that limits its use to relatively small proteins.

Therefore, it would be advantageous to develop new methods of designing D-ligands that overcome the disadvantages and limitations in the current technologies.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

Figure 23:
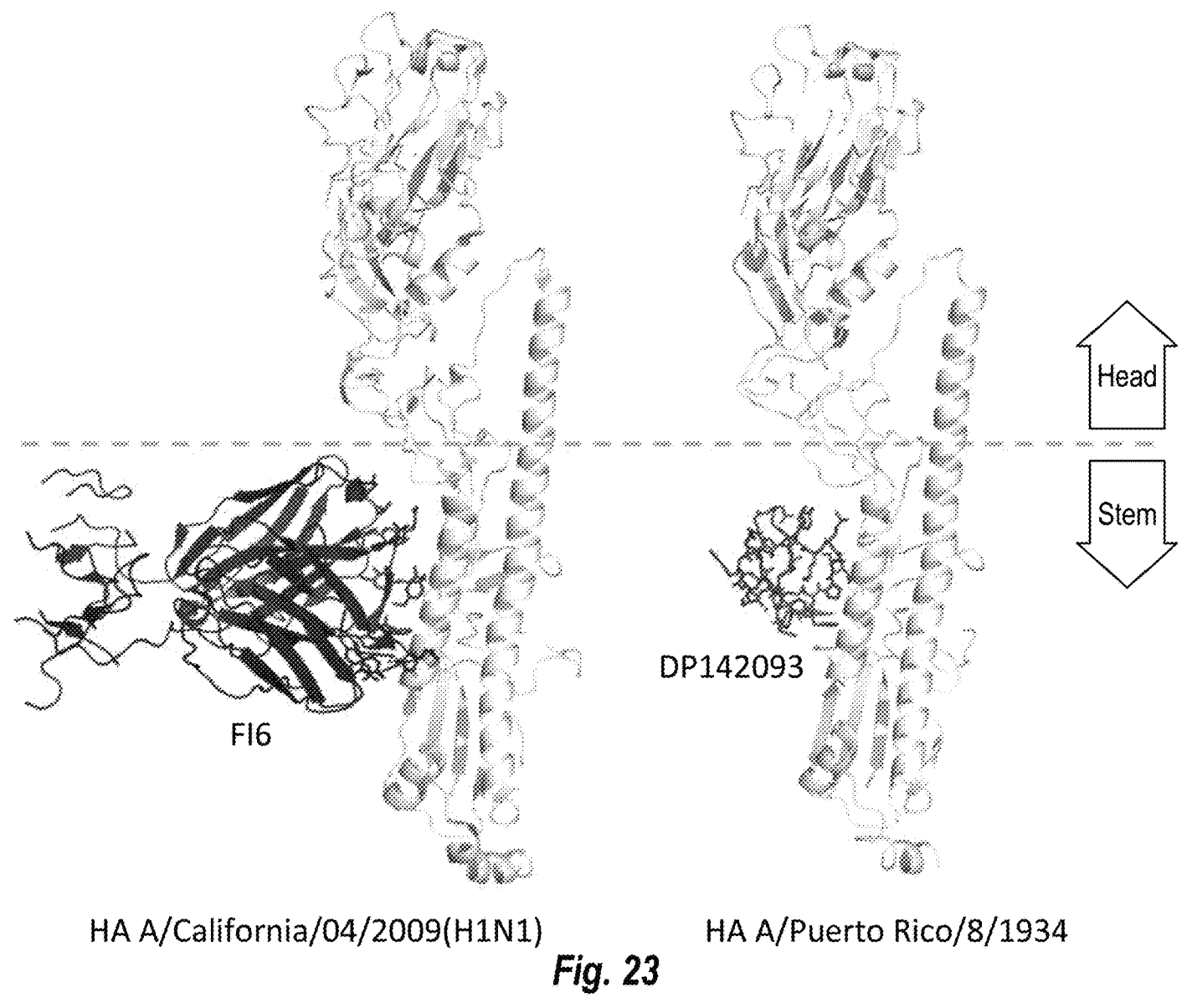

FIG. 23 shows the co-crystal of HA and FI6 Fab (left panel) used for designing the D-protein DP142093. The co-crystal of the HA and DP142093 complex presented in the right panel, proves the D-protein binds the same epitope as the FI6 antibody.

DEFINITIONS

Affinity: When two chemical entities, one being the target and the other being the ligand, interact with each other they form a complex. The propensity of ligand and target to form a complex is called binding affinity, or simply, affinity.

DDG: Delta-Delta G, which is the change of DG upon mutation of one or more amino acids, where the type of the mutation should be specified in the text. Here, expressed in Rosetta Units ("RU"), since Rosetta scoring function was used.

DG: Delta G, is the free energy change upon binding of ligand to target. Here, expressed in RU, since Rosetta scoring function was used.

Functional Group: a portion of an amino acid that recapitulates part of the interaction between the ligand and the target.

Hotspots (or L-hotspots): one or more complete residues in a peptide or protein ligand considered to be highly relevant for the interaction of the ligand with its target and formation of the target/ligand complex.

Hotspot Receivers: one or more residues in a target considered to be relevant for the interaction of the target with its ligand and formation of the target/ligand complex.

SASA: Solvent Accessible Surface Area buried upon binding of ligand to the target.

Scaffold: an L-protein of known sequence and/or structure that is used as a starting point to design a D-ligand.

Scoring Function: mathematical expression, which is a functions of molecular coordinates and aims at approximating binding affinity. Scoring functions are used to distinguish potential binders from non-binders. The result of a scoring function is a real number called "score" which, depending on the type of scoring function, must be either minimized or maximized.

Hotspot hypothesis: the list of amino acids in a complex that, via computational or experimental approaches, are considered to account for a significant part of the binding affinity via the interaction of their side chains with a target.

Pose: Three dimensional orientation of a ligand in the binding pocket of the receptor protein. A pose may come from an experiment such as X-Ray crystallography or from in silico modeling, e.g. docking.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to the field of synthetic design of proteins and polypeptides capable of binding to a target protein, and more particularly to synthetic design of proteins and polypeptides that include D-amino acids that bind to target proteins that are built of L-amino acids. The present invention further relates to the computing systems and methods for designing and selecting the proteins and polypeptides and computing methods of optimizing the binding interaction between the designer proteins and polypeptides and the target protein. The present invention includes methods to design D-ligands that are not limited by target size or ability to construct the target epitope in a D-protein. In addition, the present invention relates to the use of such designer proteins as prophylactic, therapeutic, or diagnostic agents. The designer proteins and polypeptides that are designed in accordance with the invention described herein include one or more D-amino acids and act as ligands with a target, and thereby are referred to herein as "D-ligands."

In one embodiment, the D-ligands designed with the computing systems and methods of the present invention can function as prophylactic and/or therapeutic agents that interfere with the activity of molecules that play a role in disease or homeostasis. This interference involves binding of the D-ligand to a target molecule, which binding results in regulation (e.g. inhibition or activation) of the function of that particular target molecule and/or one of the molecules with which that particular target molecule interacts. The target molecule, as non-limiting examples, can be a polypeptide, protein, nucleic acid, lipid or glycan and can be situated inside and/or outside of a cell. The D-ligand can be configured to prevent and/or treat many different diseases by being designed with properties that may be found in hormones, cytokines and antibodies that are used as prophylactic and/or therapeutic agents. The D-ligands that are designed with properties similar to antibodies, hormones, cytokines or other proteins may be capable of binding to a target (e.g., receptor protein) and evoke an activating or inhibiting signal, or can bind other molecules (e.g., other proteins) thereby influencing the activity of that molecule.

In one embodiment, the D-ligands that are designed with the computing systems and methods can be designed to have protein-protein interactions (PPI) with a target, where the D-ligands and target can have large surfaces available for the binding interaction, which results in higher specificity and lower off-target binding and related toxicity. The D-ligands are often larger than small molecules, and thereby due to the larger size, the binding region is different from the binding region of small molecules. The D-ligands can include larger interaction regions that allow binding to flat surfaces of targets, whereas the small size of chemicals dictates interactions in a deeper pocket or groove. The D-ligands can be designed to have a long half-life. The D-ligands are by nature less sensitive to proteolytic cleavage and less immunogenic compared to L-ligands that only have L-amino acids. Accordingly, the D-ligands can have improved bioavailability and half-life, as well as the opportunity of long term repeated administration. The methodologies of the present invention provide for techniques of designing in silico D-protein libraries, which can be screened in vitro for D-ligands. The design methodology is good enough to yield D-ligands from a library with a small complexity of $10^2$, which can be synthesized and screened. This is very important for the application of the methodology since larger libraries are hard to access through chemical synthesis. The lack of an efficient design approach is the reason why D-proteins against common disease targets have not been identified until now.

Figures 1A, 1B:
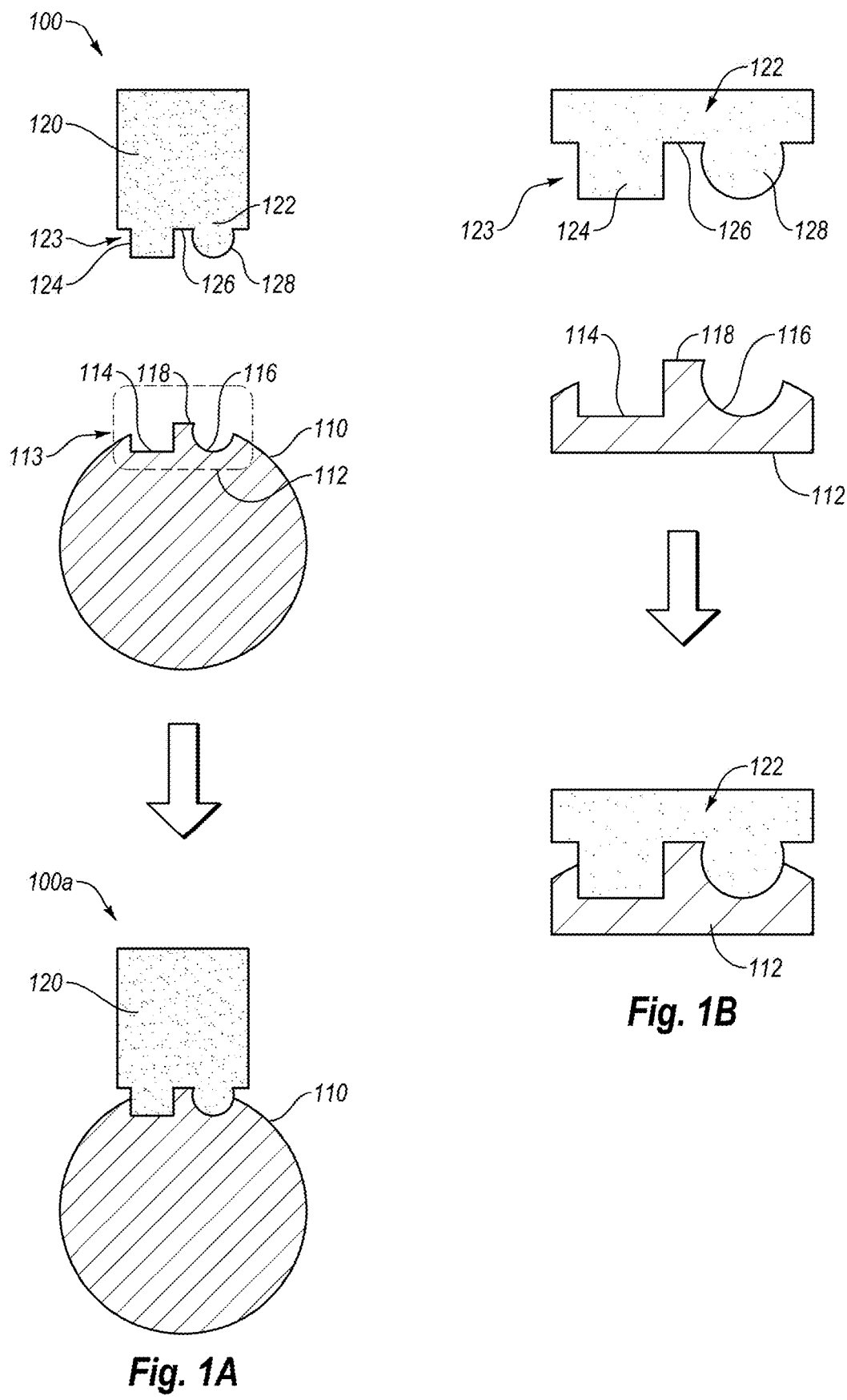
FIG. 1A includes a schematic representation of a protein target (i.e., L-target), protein ligand (i.e. L-ligand), and complex formed from the target and ligand (i.e. L-target/ligand complex).
FIG. 1B includes a schematic representation of an epitope and its hotspots, a paratope and its hotspot receivers, and a complex of the epitope and paratope (i.e., epitope/paratope complex).

In one embodiment, the present invention relates to computing systems and methodologies for designing D-ligands in silico that bind with targets. The targets can be any type of protein or portion thereof that can interact with a ligand, where a non-limiting example includes L-protein receptors, or more particularly L-protein cellular surface receptors. However, the target can be an L-protein, such as hormonal, enzymatic, structural, defensive, storage, transport, receptor, contractile, or other proteins. The targets that are L-proteins or portions thereof can be referred to as L-targets. However, the targets can be any type of protein or portion thereof whether or not a traditional receptor or receptor domain thereof. The D-ligand can be configured to target any L-target or portion thereof as well as any target substance, natural or synthetic. That is, the D-ligand can be configured to target any target substance, whether polypeptide, protein, nucleic acid, lipid or glycan, or portions thereof or combinations thereof. As such, a target may not be a traditional protein receptor, and the target can be any biological substance or portion thereof. In one example, the target can be influenza virus hemagglutinin (HA) or the stem thereof. While any biological substance may be a target; however, for explanation of an embodiment of the invention the targets are generally referred to as L-targets while the D-ligand may be designed to bind to any type of target substance.

The D-ligands can be proteins or portions thereof that can include D-amino acids that are sequenced in a D-polypeptide or combination of D-polypeptides. The D-ligands interact with a target so as to be considered a ligand, and thereby not all D-proteins can be D-ligands. The D-ligand can be included in a D-ligand grouping or system that includes a plurality of D-ligand polypeptides that cooperate with structural epitopes to form a D-ligand system. As such, the D-ligand system can include a combination of D-ligand polypeptides, separate or linked together, that form a structural epitope that together interact with the target. That is the D-ligand or D-ligand system can include at least one ligand domain that interacts with a receptor domain of the target.

In one embodiment, the L-target includes at least one L-polypeptide that interacts with and associates with at least one D-polypeptide of the D-ligand. The L-target has L-amino acids that arrange themselves in a three-dimensional conformation that provides a receptor domain that interacts with and associates with the D-ligand, and the D-ligand has D-amino acids that arrange themselves in a corresponding three-dimensional conformation to associate with the L-amino acids of the L-target. Thus, the three-dimensional conformation of the D-ligand interacts with and associates with the three-dimensional conformation of the L-target. Accordingly, the present invention can be simply described as the systems and methods configured for in silico computational design of one or more D-ligands (e.g., D-ligand library) that can be screened in vitro for binding with an L-target.

Since D-proteins, and thereby D-ligands, do not normally occur in an animal and are more stable than L-proteins in biological systems, D-ligands may be useful for administration into mammalian bodies, such as human bodies. The chemical properties of the D-ligands allow them to be configured as L-target agonists or antagonists. For example, D-ligand agonists may promote activity of an L-target. On the other hand, D-ligand antagonists may inhibit activity of an L-target. Also, D-ligands can be linked to cargo molecules similar to L-proteins, and thereby can be useful for delivery of cargo molecules that are therapeutic agents or any other cargo into cells having target receptors for the D-ligand. Accordingly, there may be significant uses for D-ligands that associate with L-targets.

The D-amino acids of the D-ligands designed in accordance with the present computing methods can be any type of natural, unnatural, essential, non-essential, canonical or non-canonical amino acids that are in the D-isomer structure. Such types of amino acids are well known, and their three-dimensional spatial orientation, hydrophilicity/hydrophobicity and charge character are well studied. However, the D-ligand includes one or more D-amino acids (e.g., at least one D-amino acid or D-amino acid sequence), and thereby may include one or more L-amino acids. For nomenclature, reference to a D-ligand indicates the presence of one or more D-amino acids with the possibility of one or more L-amino acids. In many instances, the D-ligand can be completely D-amino acids. In some instances, the D-ligand can include one or more L-amino acids, individually or in sequence, dispersed throughout the D-ligand. The present invention utilizes the base knowledge of these types of well-characterized amino acids and the data of their relative three-dimensional conformations, three-dimensional spatial orientation, symmetric folding properties respect to L counterparts, hydrophilicity/hydrophobicity and charge in order to design the D-ligands under the protocols provided herein. However, D-ligands having only canonical amino acids can be preferred in some instances.

FIG. 1A shows a schematic representation of ligand-target binding environment 100 that has a target 110 and a ligand 120. The target 110 can be any protein, such as a protein in a human body, protein of a pathogen, or any other protein, or any target substance or molecule able to bind to a protein via specific interactions. The target 110 includes an epitope 112, which is a place on the surface of the target 110 where the ligand 120 is known to interact or can interact with the target 110. The epitope 112 can include one or more three-dimensional conformations that each arises from the polypeptide sequence and physicochemical nature in the region of the epitope 112, and possibly also because of other amino acids in the target 110 that interact with the amino acids in the epitope 112 due to their physiochemical properties. The three-dimensional conformation or structure of the epitope 112 can be influenced by the positive and negative charges, hydrogen boding, van der Waals forces or other atomic interactions that can be involved in binding with the ligand 120. Here, the schematic representation of the epitope 112 includes a square recess 114 and round recess 116 separated by a protrusion 118, the epitope 112 can be any recess or protrusion that is exposed on the surface of the target 110.

In one embodiment of the present invention, the target 110 can be an L-protein with L-amino acids that are linked together in one or more L-polypeptides to form the epitope 112 (e.g., L-epitope). The square recess 114 and round recess 116 separated by a protrusion 118 of the epitope 112 can be a schematic representation of hotspot receivers 113 as they receive hotspots 123 of the paratope 122 as described below. It should be noted that the paratope 122 includes the hotspots 123.

The ligand 120 can be any type of ligand, where a protein ligand is described herein for the purposes of preparing the D-ligands. The ligand 120 can be any type of protein that can interact with and bind to the epitope 112 of the target 110. An example of a ligand 120 is an antibody. The ligand 120 can include a paratope 122, which is a place on the surface of the ligand 120 that interacts and binds with the epitope 112 of the target 110. The paratope 122 includes hotspots 123, which are the portions of the paratope 122 that contribute (e.g., significantly contribute) to the binding energy when binding to the epitope 112. Here, the hotspots 123 are schematically represented by a square protrusion 124 and a round protrusion 128 separated by a recess 126. For illustration purposes, the square protrusion 124 and round protrusion 128 separated by the recess 126 of the paratope 122 match and mate with the square recess 114 and round recess 116 separated by the protrusion 118 of the epitope 112, which is shown in environment 100a. The binding of the paratope 122 with the epitope 112 facilitates the ligand 120 targeting and binding with the target 110. While FIGS. 1A-1B provide a schematic illustration of ligand-target association and binding, it is representative of the interactions that are desirable for the D-ligands that are designed by the present invention. Accordingly, the present invention can allow for computational design of D-ligands (e.g., 120) that bind with L-targets (e.g., 110). FIG. 1B shows an enlargement of the binding of the epitope 112 and paratope 122.

In one embodiment, the method of designing D-ligands uses information (e.g., experimental data) about an antibody (also denoted as L-antibody) binding to L-target protein. As such, the starting information can be obtained from the structure of the complex between two different L-proteins: L-antibody and L-target. In one example, the information is experimental data that is available from a databank. From the experimental data available for the L-antibody and L-target, computer data processing and manipulation protocols can arrive at one or more D-ligands that bind the L-target. It is preferable that the protocols of the D-ligand design methodologies result in a plurality of D-ligands that bind with the L-target, which can be included in a D-ligand library. The designed D-ligands can be computationally analyzed and screened in silico for theoretical binding with the virtual L-target. Once criteria for prioritizing one or more D-ligands (e.g., lead D-ligands) from the D-ligand library are determined, these lead D-ligands can be synthesized and tested in vitro for binding with the L-target and/or in-vivo in various screening assays. Accordingly, the method of designing D-ligands can include in silico design protocols and real synthesis of D-ligands and in vivo assays and/or in-vivo assays with real L-targets.

The computing systems that process the computing methods of the invention that design D-ligands can be any type of computing system that has the modules and software described herein. These computing systems can include memory devices having computer-executable instructions for performing computing functions for the D-ligand design methodologies. The computing systems can receive certain data regarding L-proteins, and computational manipulation of the data can generate sequences of amino acids of the D-proteins. This can include sequences that include D-amino acids, and optionally some L-amino acids. While the invention covers various computational protocols that can be implemented to design D-protein ligands that target L-protein targets, such computational protocols may be varied under the concepts provided herein for D-ligand design. Accordingly, the computing systems can be used for implementing in silico methodologies to design of the D-ligands. In one example, the computing protocols can be processed with data obtained from real interactions of an L-antibody that binds with the L-target, which real interactions can be obtained from data from deposited crystal structures or other experimental data.

Figure 2A:
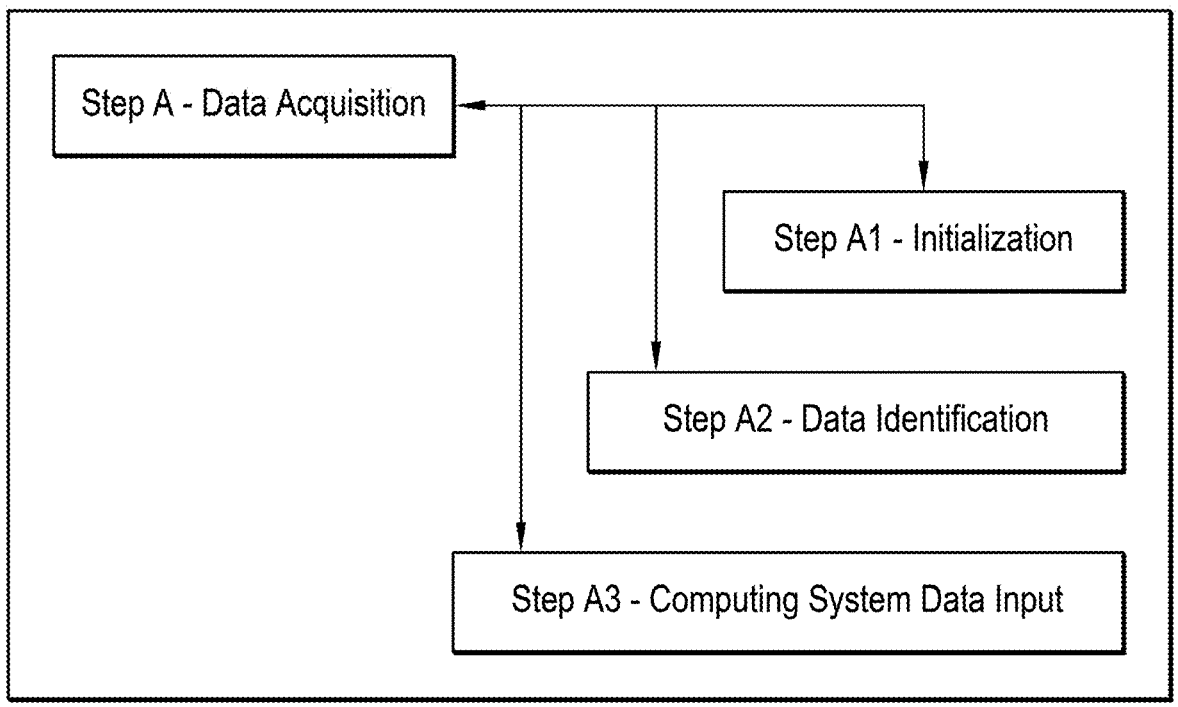
FIG. 2A includes a diagram of method steps of an in silico computing methodology for data acquisition.
Figure 2B:
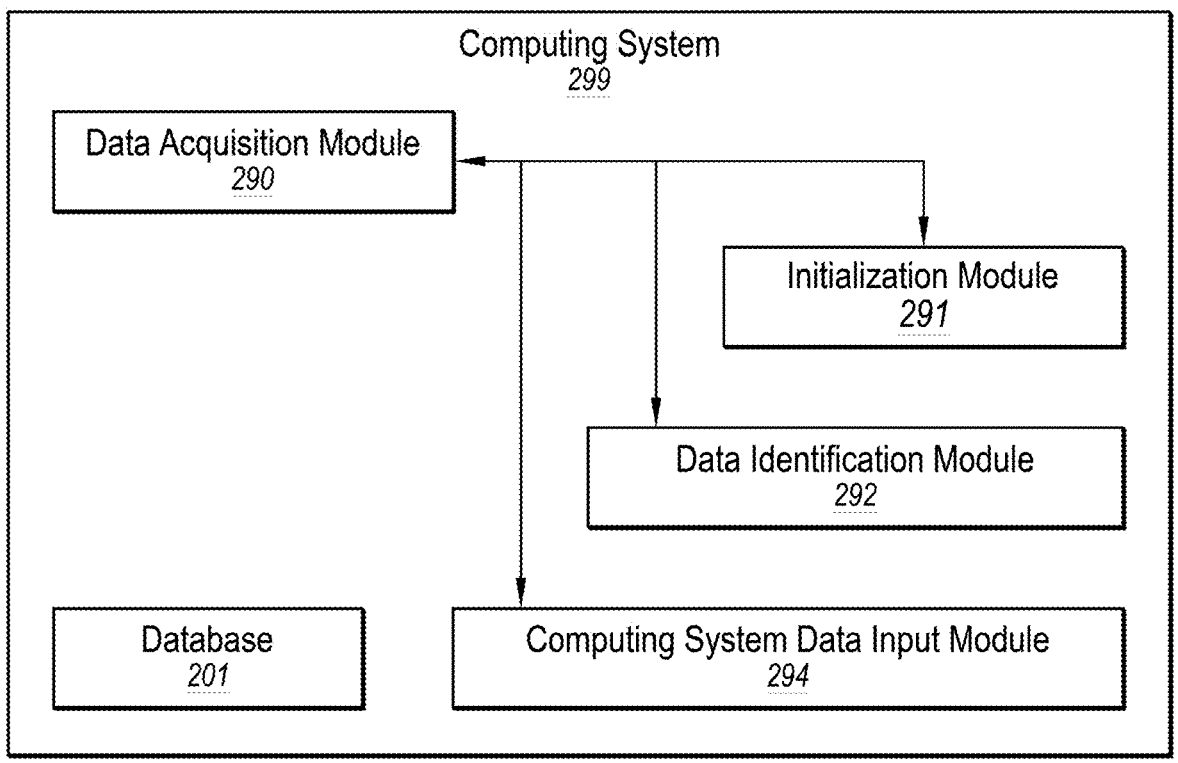
FIG. 2B includes a schematic diagram of a computing system with modules configured for performing the in silico computing methodology of FIG. 2A.

FIG. 2A shows Step A—Data Acquisition to include: Step A1—Initialization; Step A2—Data Identification; and Step A3—Computing System Data Input. These steps and sub-steps are described below. FIG. 2B shows the computing system 299 having computing modules that can perform the computing methodologies of FIG. 2A, such as Step A—Data Acquisition.

FIG. 2B illustrates the computing system 299 with the database 201 and computing modules configured to perform the steps of FIG. 2A. While not specifically shown, the computing system 299 can have a computing module configured to perform any of the method steps described herein, and reference to any method step is also a reference to a module configured to perform that method step. The computing modules can be any combination of data storage device (e.g., memory device), software, hardware, or the like. As shown, the computing system 299 includes a data acquisition module 290 that can be coupled to or include sub-modules. The data acquisition module 290 can be configured to implement data acquisition protocols in accordance with the principles described in connection to Step A or other method steps. Also included is an initialization module 291 that can be configured to implement initialization protocols in accordance with the principles described in connection to the method steps described herein. A data identification module 292 can be included and configured to implement data identification protocols in accordance with the principles and method steps described herein. Further, the computing system 299 can include a computing system data input module 294 configured to implement data input into the computing system in accordance with the principles described herein in connection with method steps, which can include manual or automatic data input from human, computer, or database sources.

In FIG. 2A, Step A (e.g., Step A—DATA ACQUISITION) is shown to perform data acquisition (e.g., experimental analysis and/or experimental databank) of an L-ligand (e.g., an L-antibody) 130 that binds with a protein L-target 110 to form an L-target/L-ligand complex 140. That is, the L-ligand 130, L-target 110, and/or L-ligand/L-target complex 140 may be analyzed with in vitro and/or in vivo assays to obtain experimental data related to the amino acids and polypeptides of: the L-paratope 122 and L-hotspots 123 of the L-antibody ligand 130; L-epitope 112 and L-hotspot receivers 113 of the L-target 110; and interactions of the amino acids of the L-paratope 122 and L-epitope 112 and of the L-hotspot and L-hotspot receivers of the L-antibody/L-target complex 140. This can include analysis of the L-epitope 112 hotspot receivers 113 and/or the L-paratope 122 hot spots 123, as well as the interaction and binding thereof. However, such experimental data may be in a databank that can be accessed, such as automatically or from input by a human. Particularly, the data of Step A can include amino acid and/or polypeptide data from three-dimensional structures, hydrophilicity/hydrophobicity profiles and charge alone or in relation to other amino acids and/or polypeptides. Examples of, Step A data that can be acquired can include: molecular structure data; mutagenesis data; and binding data, whether from experiment or in silico simulation and prediction. The data acquisition can depend on experience of a human molecular modeler to identify data for the methodology 200 as well as obtaining such data. A result of this phase can be a three-dimensional model of the L-ligand in complex with the L-target.

Step A1 can include an initialization phase, which may or may not be done by the computing system or methodology software. The initialization phase can include the protocols for initializing the methodology. This can include instructions for the methodology to begin, which may be instructions to a human molecular modeler to obtain the data or instructions to the computing system 299 to access a database 201 and acquire the data.

Step A2 can include a data identification phase for identifying key contact amino acids of the L-ligand, which in this context can be defined as hotspots. The identification of key contact amino acids of the L-ligand can be conducted through one or more of the following methods: 1) visual inspection; 2) mutagenesis data; 3) analysis of conserved interactions; and 4) in silico prediction of binding energies, as well as other methods.

Step A3 may also include inputting such data into a database 201 of the computing system 299. The data can be input into the database 201 by any method, including human input and/or the computing system 299 accessing the data from another database and/or computing system. The data is input into a database 201 of the computing system 299 so that the computing system 299 can perform data processing operations in accordance with the in silico methodologies described herein. The database 201 can be a hotspot hypothesis data base. Also, the database 201 can be accessed in any method step to obtain the requisite data, and any data determined by any method step can be input into the database 201. Accordingly, the computing system 299 and database may be continually accessed for information and modified by information as it is obtained during the in silico methodologies.

Figure 3:
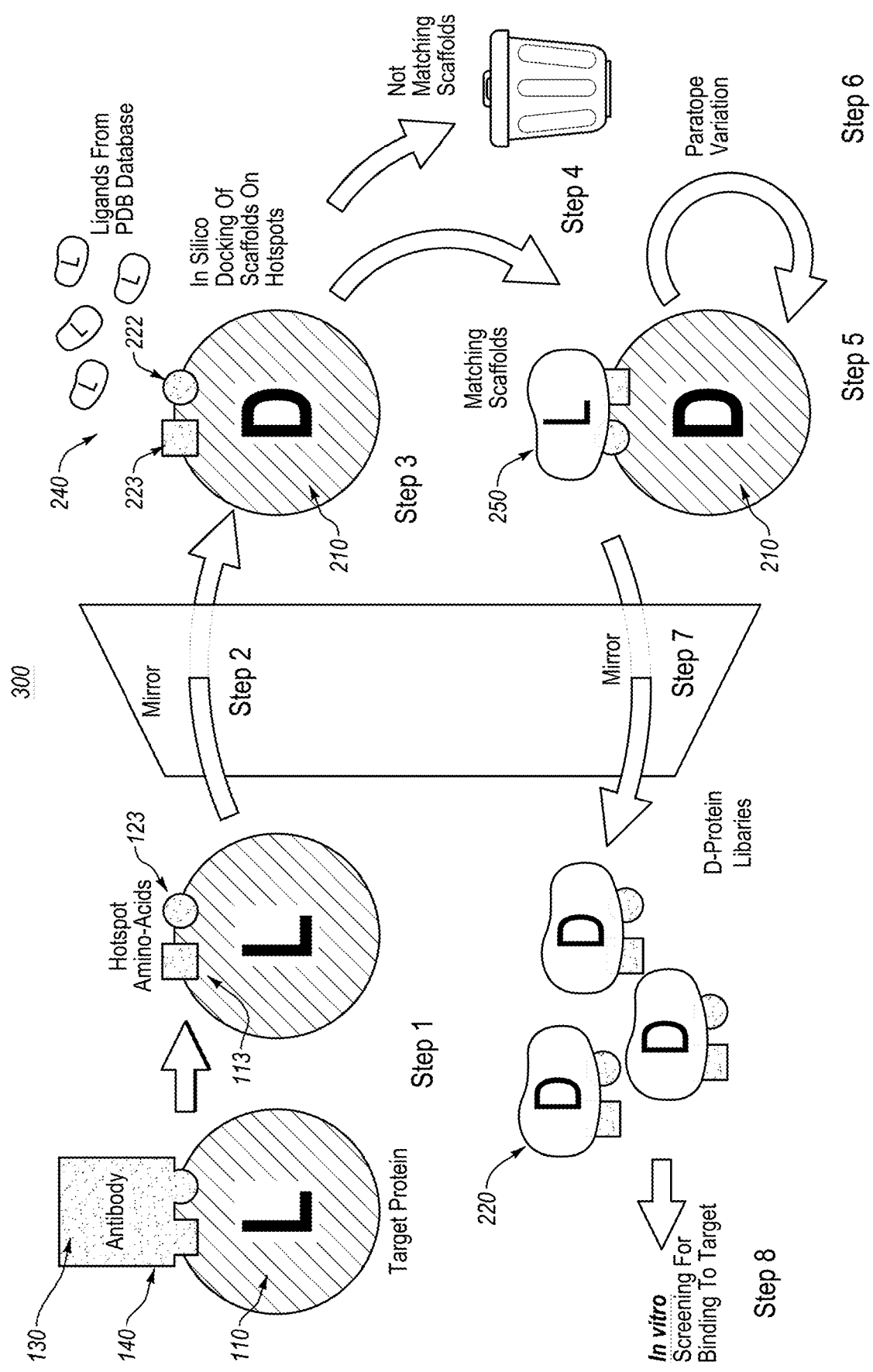
FIG. 3 includes a schematic representation of an in silico computing methodology for designing D-ligands that bind with L-targets.

FIG. 3 illustrates a schematic representation of an in silico methodology 300 for designing D-ligands 220. Various steps are shown for the methodology 300; however, the steps may be rearranged in another order, and some steps may be omitted or modified in accordance with the principles described herein. In FIG. 3, the methodology 300 is shown to include: Step 1 (e.g., Step 1—HOTSPOT HYPOTHESIS); Step 2 (e.g., Step 2—MIRROR INVERSION); Step 3 (e.g., (Step 3—HOTSPOT LIBRARY GENERATION); Step 4 (e.g., Step 4—SCAFFOLD MATCHING); Step 5 (e.g., Step 5—HIT IDENTIFICATION); Step 6 (e.g., Step 6—HIT OPTIMIZATION); Step 7 (e.g., Step 7—HIT MIRROR INVERSION); and Step 8 (e.g., Step 8—SYNTHESIS AND SCREENING).

Figure 10:
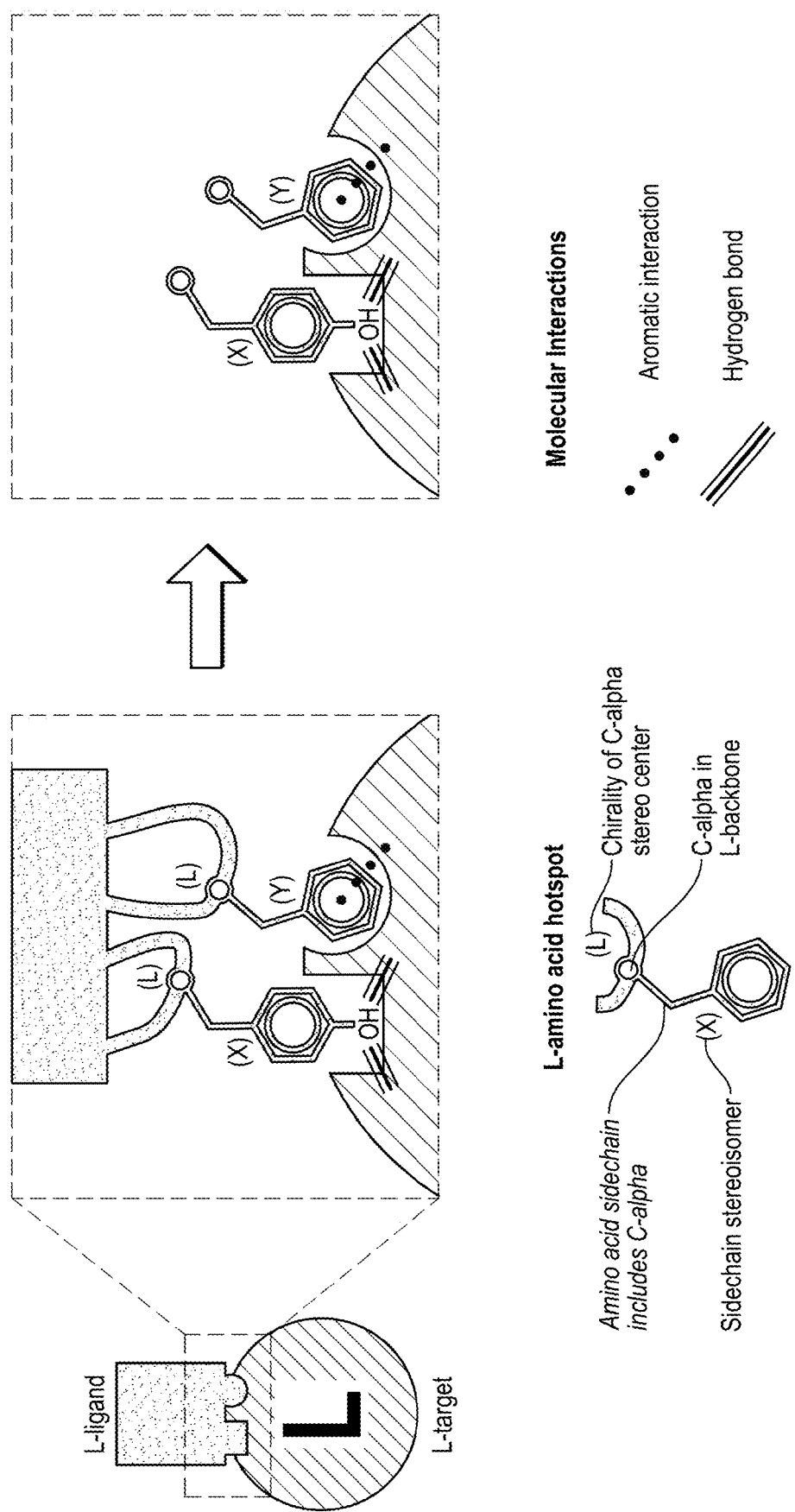
FIG. 10 includes a schematic diagram of isolating hotspot side chains from the rest of the polypeptide backbone.

Step 1—HOTSPOT HYPOTHESIS generally includes data analysis of the binding between the antibody 130 and target protein 110 to form the target/ligand complex 140, or more particularly binding between paratope of antibody 130 and epitope of target protein 110, or more particularly binding between hotspots 123 of the paratope with hotspot receivers 113 of the epitope, and structural manipulation of the antibody 130, paratope, and hotspots 123. Then, the antibody-target complex structure can be manipulated in-silico by removing the entire antibody except for the hotspot side chains. Step 1 can include structure manipulations in which a number of in-silico variants of the complex between the target and different sets of hotspot side chains are generated. Each of such complexes is called a hotspot hypothesis. More specifically, as shown in FIG. 10, the template L-ligand (e.g., antibody) can be deleted so as to leave only side chains of the hotspots 123 interacting with the target protein 110. A result of this, the data can include a three-dimensional model of the side chains of the hotspots 123 in complex with the L-target 110. The data can be complemented with further information, such as mutagenesis or other experimental data. FIG. 3 depicts the D-ligand design process for only one hotspot hypothesis represented by hotspot amino-acids 123. In a case where multiple hotspot hypotheses are defined, the design procedure can be repeated for each hotspot hypothesis.

Figure 11:
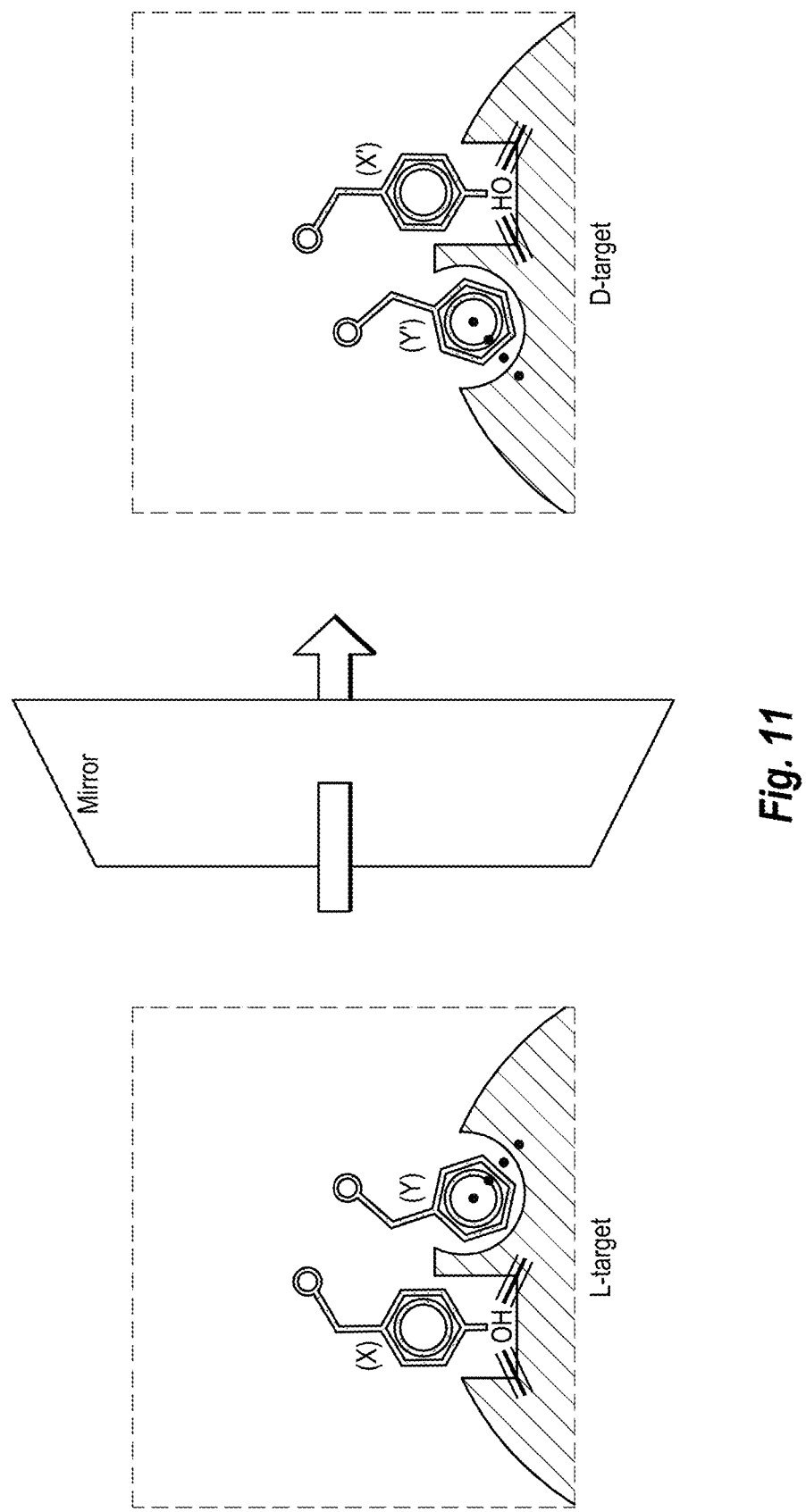
FIG. 11 includes a schematic diagram of mirror inversion.

Step 2—MIRROR INVERSION can include the mirror inversion of the L-target 110 in complex with L-hotspot side chains 123. It is noted that Step 2 may be optional in certain embodiments where the design is done without implementation of a mirror inversion. This operation results in a complex 240 of D-target 210 and mirror D-hotspot side chains 222 and 223. FIG. 11 illustrates a mirror inversion. Mirror inversion is performed by manipulating the data of the coordinates of the atoms of the target-hotspot complexes. Mirror inversion can be performed through any arbitrarily placed mirror plane.

Figure 19:
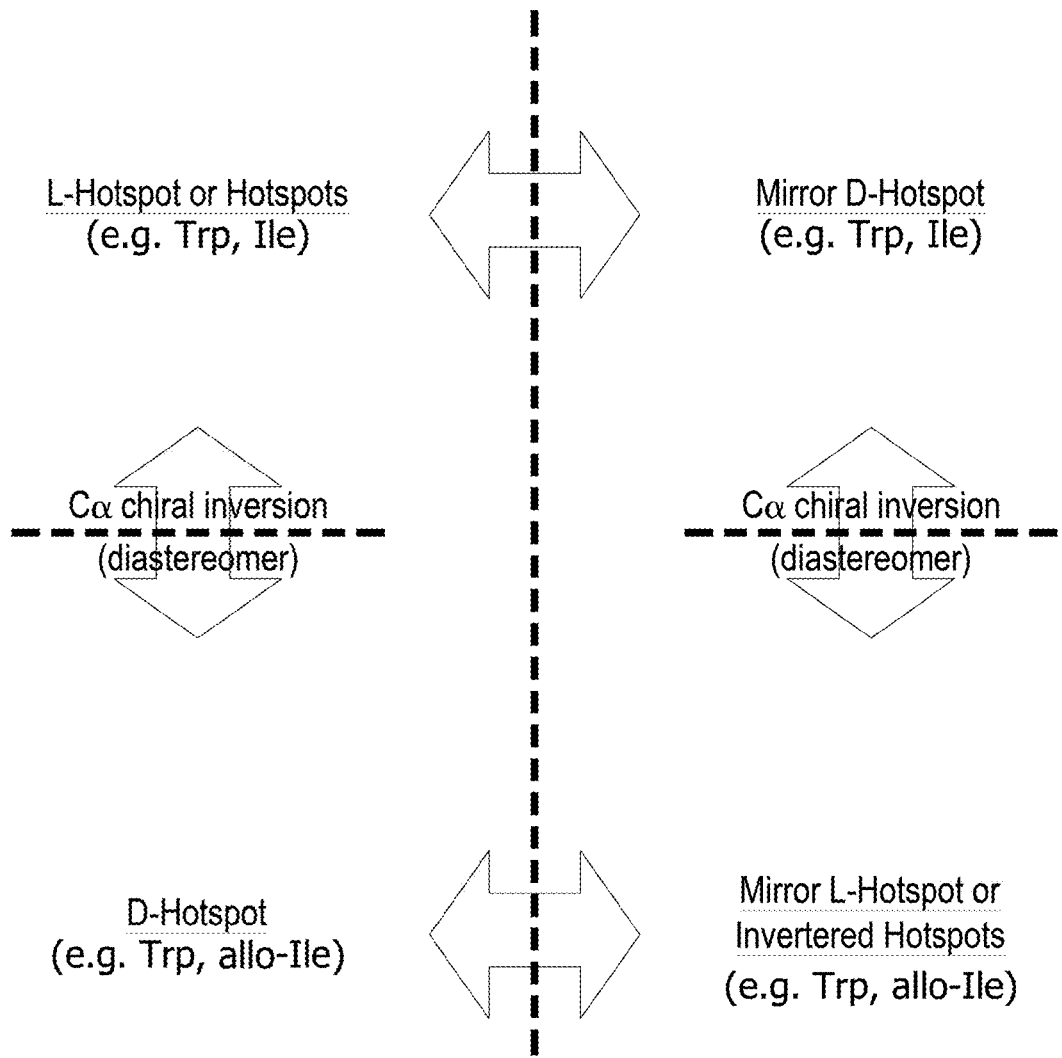
FIG. 19 includes a diagram of amino-acid name conventions, with mirror referring to sidechain chirality and L/D referring to Cα chirality.

Step 3—HOTSPOT LIBRARY GENERATION can include steps for determining alternative mirror D-hotspot side chains, mirror D-hotspot side chain poses and conformations that are compatible with the hotspot receivers of the target. This results in a plurality of mirror D-hotspot side chains and mirror D-hotspot side chain positions that cumulatively together can be referred to as a mirror D-hotspot side chain library. The mirror hotspot side chain library can then be processed with backbone regeneration to obtain a mirror L-hotspot amino-acid library, to which we further refer to as "hotspot library". In Step 3, the orientations of the mirror D-hotspot side chains 222 and 223 are diversified by various interaction-preserving transformations (see FIG. 12). In one example, only the orientations that preserve the native target-ligand interactions are accepted in the library. All or a portion of the orientations of the mirror D-hotspot side chains 222 and 223 are next submitted to a routine that recreates the entire (or portion, such as functional portion) amino acid starting from the side-chain (see FIG. 13)—so called backbone regeneration. The missing backbone atoms are rebuilt with inverted chirality of the Cα (L-chirality) resulting in "Mirror L-hotspot aminoacids" or simply "inverted hotspots" (See FIG. 13). Here, the word inverted applies to the inverted chirality of the Cα. The inverted hotspots are amino-acids with L-chirality; however their sidechain conformations are mirror images of the conformations of the respective L-hotspots. For each inverted hotspot in the library, all (or a portion) available sidechain rotamers are included whenever the structure of the target sterically allows for it. Note that the backbone regeneration can also be performed prior to the interaction-preserving transformations without loss of generality. The hotspot library can then be further diversified in a way that preserves the hotspot-target interactions. For instance by redocking the inverted hotspots or by using other conformational sampling techniques. This final step results in a further refined hotspot library (see FIG. 14). In the end all (or a selected portion) amino-acids in the library are tested for overlap with the target protein, and all residues of the library which present clashes with the D-target are rejected. As a result of Step 3, each amino-acid in the hotspot library preserves the native hotspot interactions, does not clash with the target receptor, and has chirality inverse to that of the target. In FIG. 19 the nomenclature adopted in this document is clarified: the hotspot amino acid (or L-hotspot) becomes mirror D-hotspot amino acid when mirror inversion is performed. Once the Cα chiral inversion is performed, mirror D-hotspots become mirror L-hotspots or inverted hotspots. This step of the methodology is the key step of the invention, that allows for the change of the chirality of the ligand.

Figure 15:
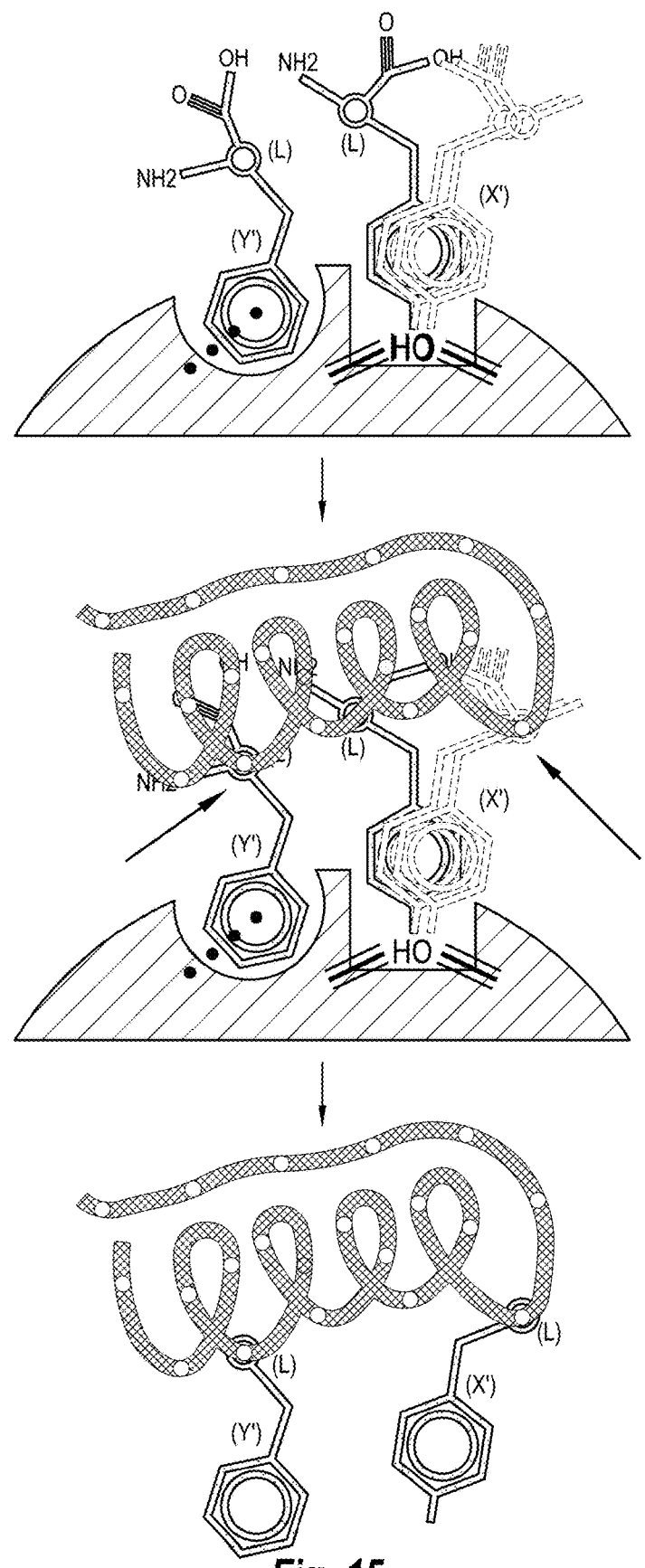
FIG. 15 includes a schematic diagram of the inverted hotspot library being matched with L-scaffolds.
Figure 16:
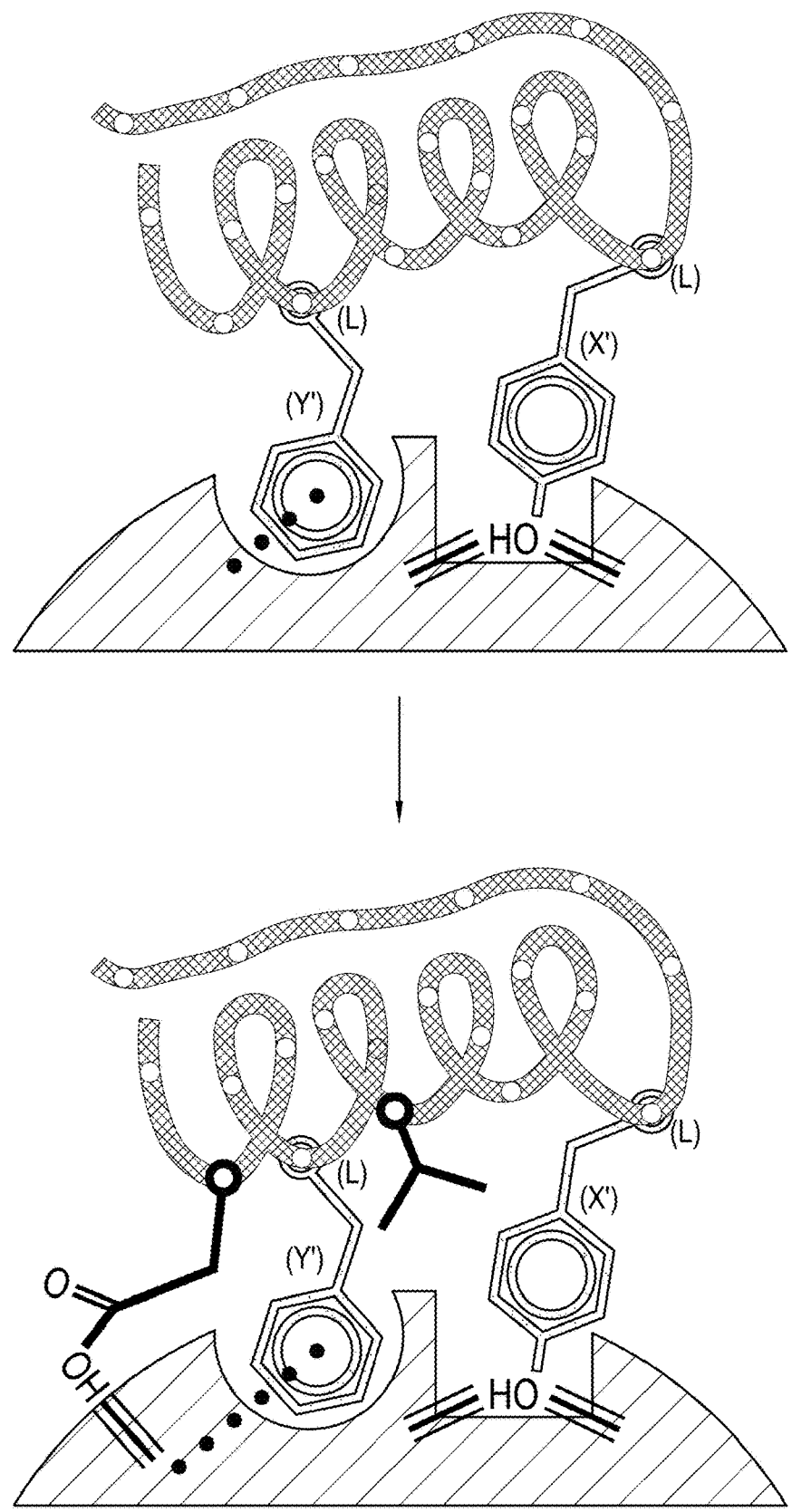
FIG. 16 includes a schematic diagram of generating scaffolds with similar conformations having different amino acids around the hotspots to obtain hits.

Step 4—SCAFFOLD MATCHING can also include the generation of a database of the L-scaffolds that may potentially bind with the D-target 210. As shown in FIG. 15, the hotspot libraries are matched with a database of scaffolds to determine scaffolds that could simultaneously acquire all different inverted hotspots from the library (as in ref WO2013138259 A2). In the example in FIG. 15, hotspot amino-acid Tyrosine has three conformations, while the Phenylalanine has only one conformation. Only one of the three conformations of the Tyrosine allows for simultaneous grafting of all hotspots (Phenylalanine and Tyrosine) on the scaffold. The other, non-matching conformations are neglected for this scaffold, but can be reused for another scaffold. A large number of conformations for each hotspot increase the chances of finding a good match with an L-scaffold. As shown in FIG. 15, the matching process results in a complex of the L-scaffolds and the D-target. The L-scaffold is superimposed on the hotspots, and the matching hotspot conformations are selected and merged with the L-scaffold. The resulting L-scaffolds having grafted hotspots can have the surrounding amino acids redesigned in order to increase shape complementarity with the D-target, reduce intramolecular clashes and improve the score of the in-silico complex (see FIG. 16). Here, an L-scaffold with grafted inverted hotspots is subject to two mutations (Valine and Aspartic Acid) that may remove the clashing or improve complementarity between the L-scaffold and the D-target thus improving the score of the complex. The resulting complex can then be subject to a number of criteria qualifying it as a hit in Step 5.

Step 5—HIT IDENTIFICATION can include selecting design for further redesign and optimization. The selected designs are called hits 250. The hits 250 are L-scaffolds having the hotspots 222 and 223 from the antibody 130 grafted in such way that they keep the antibody's paratope 123 three dimensional structure. The hits 250 also have a number of additional mutations that improve the complex 250-210 score.

Step 6—HIT OPTIMIZATION can include improving the initial L-ligand hits 250 that are predicted to bind with the D-target 210 by in silico mutation analysis, repeated docking, side-chain repacking, re-assessment of the quality of the designs according further criteria (re-scoring), molecular dynamics, any other method that can help improve the binding affinity of one protein against its target receptor (see FIG. 17). If at any point of the hit optimization, the similarity to the antibody paratope structure 123 is lost, the hit can be neglected from further processing.

Step 7—HIT MIRROR INVERSION can include the mirror inversion of the improved L-ligand hits 250 to their corresponding D-ligands 220.

Step 8—SYNTHESIS AND SCREENING can include synthesis and in-vitro screening of the D-ligands 120 for binding with the L-target 110 to confirm D-Ligand/L-target specific binding.

The computational steps and logic flow diagrams for Step 1 are provided in FIG. 4. The computing system 299 and corresponding modules for implementing Step 1 of the in silico methodology 300 for designing D-protein ligands 220 is illustrated and described in connection with FIG. 5.

Step 1 can include identification of key contact amino acids in a target/ligand complex for determination of hotspot hypotheses. Here, the hotspot hypothesis can include a set of key amino-acids in the paratope, which likely contribute significantly to ligand binding affinity or specificity. The set of hotspot amino-acids can be determined with different methodologies, for instance with alanine scanning or computational methods. If the number of hotspots is larger than 2, multiple hotspot hypotheses can be derived, containing different numbers and different types of amino-acids belonging to the hotspot amino-acid set. Accordingly, one or a plurality of hotspot hypotheses can be determined. Often, there is usually a plurality of hotspot hypotheses. Non-hotspot amino-acids can be added to the hotspot hypotheses in case they form specific interactions with the target. Some hotspots can be determined by the human molecular modeler based on the methods described herein. The different hotspot hypotheses may lead to different D-ligands and possibly to different D-ligand libraries.

Determination of the hotspot hypothesis can include identifying paratope amino acids that are likely to be a hotspot. In one aspect, various methods can be used for identifying hotspots, and as such any method known or developed can be used. In one aspect, hotspots are normally large amino acids that form multiple interactions with the target epitope. As such, mutating a hotspot amino acid to alanine may in some instances result in a significant decrease of binding affinity. The crystal structure can provide information for amino acids that are potential hotspots.

Determination of the hotspot hypothesis can include identifying hydrophobic paratope amino acids. In one aspect, the hotspot hypothesis can initially include large hydrophobic amino acids, such as tryptophan (Trp or W) or phenylalanine (Phe or F), as first candidates for a hotspot residue analysis. These amino acids have large interaction surfaces and are likely to contribute significantly to binding affinity if buried at the complex interface. Secondly, other hydrophobic amino acids can be considered.

Determination of the hotspot hypothesis can include identification of one or more extra paratope amino acids that contribute specific interactions or stabilize the conformation of hotspots. The extra paratope amino acids can be at any position in the paratope, such as adjacent to or far from the hotspot amino acids. The adjacent or proximal amino acids can be 1 to 30 Angstrom away from a hotspot, or preferably 1-10 Angstrom amino acids away, or more preferably adjacent to the hotspot. In one aspect, the one or more extra paratope amino acids can be a flanking residue stabilizing the conformation of the neighboring hotspot. In another aspect, the extra paratope amino acids can be amino acids that form a hydrogen bond or salt-bridge, or have a high level of shape complementarity with the receptor. Thus, at least one extra paratope amino acid can be added to the hypothesis.

In one embodiment, the hotspot hypothesis can include Step 1A (e.g., Step 1A—Isolate Hotspot Sidechains) which includes isolating hotspot sidechains from the rest of the native ligand. This can include the in silico methodology to process the L-ligands and/or L-paratopes and/or the L-hotspots into the amino acid side chains thereof. The amino acid side chains remain intact, and retain the three-dimensional spatial orientation and relative conformation with each other, as well as the hydrophilicity/hydrophobicity and ionic character. Once disconnected from the protein backbone, the side chains are no longer chiral, and thereby not L or D, except for Thr and Ile. During removal of the non-hotspots from the ligand structure, alpha carbons are kept, but since the rest of the amino-acid backbone is also removed, the carbons lose their chiral character.

FIG. 10 shows that the structure of the template L-ligand (e.g., antibody) can be removed so as to leave only side chains of the hotspots interacting with the L-target. Here, sample hotspot amino acids interacting with the receptor are depicted, the chirality of carbons-alpha is indicated (L) and the side chains of the hotspot amino acids are indicated as X and Y. If the side chain X is not chiral then its mirror image X' will be the same chemical moiety as X, so X=X'. In case the side chain has a chiral center(s) then X≠X'. While the representative side chains may not actually be chiral, the X and Y indicate that some amino acids other than those illustrated may have such side chain chirality. The side chains may also be from non-canonical or other non-natural or non-essential amino acids. The aromatic interactions and hydrogen bonding interactions are schematically represented for the L-ligand bound to the L-target receptor. Then the L-ligand is removed except for the side chains of the amino-acids belonging to the hotspot hypothesis, and their carbons-alpha. The side chains remain docked in the L-target, and keep their structure, but the chiral center at the carbon-alpha is removed.

In one aspect, once the hotspot hypothesis is selected, everything but the hotspot side chains and the hotspot amino acid alpha carbons is removed in silico from the L-ligand. As presented in FIG. 3, L-ligand hotspot side chain 123 is isolated from its native polypeptide chain.

However, in one aspect, the L-ligand does not need to be removed at this precise stage. The following processing can be performed with the entire amino acid, paratope, or ligand. As such, the following processes can be performed with the entire amino acid, paratope, or ligand that contains the hotspots. For example, the mirror inversion can be performed with the entire target/ligand complex. In still another aspect, the L-ligand removal can occur after the mirror inversion.

The systems and methods can use any process for detecting hotspots, which can include validation of being a hotspot. Various computing processes can be used for the amino acid hotspot analysis to determine hotspot amino acids that form interactions with the target. Hotspots are normally large amino acids that form multiple interactions with the target. Mutating the hotspot to alanine results in significant decrease of binding affinity, thereby indicating the hotspot is involved in binding with the target. The hotspot hypothesis proceeds until one or more hotspots are identified.

Accordingly, FIG. 10 can represent: A) identification of structure of L-ligand binding the L-target; B) performing the hotspot hypothesis by determining which amino acids are hotspots for the binding of the L-ligand with the L-target; and C) removing the L-ligand so as to only leave the hotspot side chains with the carbon alpha.

FIG. 4B also shows Step 2—Mirror Inversion. The mirror inversion in Step 2 can include complex inversion, and inversions of any portions thereof containing the target—ligand interface, such as inversion of the target or the epitope in complex with the ligand, ligand paratope, ligand hotspots or ligand hotspot side chains. For example, different methods may use different mirror inversions depending on external modeling software capabilities employed in the process. Accordingly, the entity that is processed through mirror inversion may be used for further processing in the in silico methodology 300. Also, a combination of the mirror inverted entities may be combined to create the mirror inverted entity that is further processed. The mirror inversion can be performed by algorithms that use data about the entities in order to generate a spatial mirror image thereof. The mirror inversion of the entity may or may not be rendered in a graphical user interface. The computing system 299 of FIG. 5 can include a mirror inversion module 280 to perform the mirror inversion methodologies of Step 2.

Generally, in Step 2 the mirror inversion can be conducted on the entity or entities to be further processed. Step 2 can be conducted based on the data obtained from the data of Step 1. However, additional information may be accessed from public or proprietary data, such as crystal structure data. In one example, after identification of hotspot hypothesis in Step 1, the three-dimensional coordinates of the complex of the L-hotspot receivers with the L-hotspots can be obtained, and then the mirror inversion of the three dimensional coordinates is performed. As such, the L three-dimensional coordinates are mirror inverted to D three-dimensional coordinates.

FIG. 11 illustrates a mirror inversion of sample amino acid side chains belonging to the hotspot hypothesis. Here, only the side chains attached to a carbon alpha are shown. The sidechains before mirror inversion are called X and Y, and their enantiomers are called X' and Y'.

Accordingly, the structure of the D-target can be generated in Step 2. Also, the three-dimensional coordinates of the L-target and/or L-epitope and/or L-hotspot receivers or side chains thereof can be mirror inverted into three-dimensional coordinates of the D-target and/or D-epitope and/or D-hotspot receivers or side chains thereof in Step 2. Similarly, a D-ligand or D-paratope or D-hotspots can be generated in Step 2. Also, the three-dimensional coordinates of the L-ligand and/or L-paratope and/or L-hotspots can be mirror inverted into three-dimensional coordinates of the D-ligand and/or D-paratope and/or D-hotspots in Step 2. Also, the three-dimensional coordinates of the complex of the L-target/L-ligand and/or complex of the L-epitope and L-paratope can be mirror inverted into the complex of the D-target/D-ligand complex and/or complex of the D-epitopes and D-paratopes and/or the complex of the D-hotspot receivers and D-hotspots. As can be realized in accordance with Step 2, the mirror inversion can be performed on any of the molecules or portions thereof or side chains thereof.

In one aspect, the mirror inversion can be a simple conversion of a sequence of L-amino acids (abbreviated here an L-sequence) to the same sequence of D-amino acids (abbreviated here a D-sequence). Here, L-structure represents the three-dimensional coordinates of the amino acids of a protein defined by the L-sequence and the D-structure represents the three-dimensional coordinates of the amino-acids of a protein defined by the D-sequence. Conversion of an L-sequence to a corresponding D-sequence results in a protein folding into a D-structure that is the exact mirror image of its L-structure.

In one aspect, the mirror inversion can be a basic mathematical transformation of a geometrical object. This can include defining a plane (e.g., arbitrary choice, in this case xy-plane) and changing the sign of all z coordinates. Similarly, xz-plane, yz plane, or any other plane can be used for the reflection transformation. It is worth noting that the resulting chirality of the transformed molecule is not depending on the adopted plane.

The mirror inversion protocol can be recalled and performed at various stages within the in silico 300 methodology whenever is most convenient according to the external modeling software capabilities employed in the process.

Accordingly, FIG. 11 represents the geometric mirror inversion of the complex between the L-target and side-chains of a hotspot hypothesis. This includes mirror inversion transformation of the coordinates of the L-target resulting in the conversion of the L-target to the D-target and mirror inversion of the hotspot side chains docked with the L-target as shown. The sidechains X and Y can be chiral, so their mirror images X' and Y' may be different chemical moieties. This mirror inversion process can be performed at any step of the protocols described herein. Also, any portion of the ligand target complex containing the epitope and the paratope interface can be inverted for further processing by the methodology of FIG. 4. As such, any portions containing the target—ligand interface, such as target or the epitope in complex with the ligand, ligand paratope, ligand hotspots or ligand hotspot side chains can be mirror inverted and then inverted back again. The inversion can occur at the steps described herein or at any time during the protocol.

Step 3 includes steps for preparation of protein structures (e.g., hotspots and scaffolds) for Step 4, where the inverted hotspots can be grafted on a scaffold in order to identify L-ligands that may possibly have L-hotspots that interact with and bind to the D-hotspot receivers of the D-target and/or D-epitope. In Steps 3 and/or 4 the scaffolds are obtained and entered into the database 201 of the computing system 299 so that the in silico screening for binding to the D-target can be performed. The scaffolds may also be obtained by iterative design, for instance, by performing molecular dynamics simulations, or any other conformational sampling technique, applied on the scaffolds already stored in the database. The 3D coordinates may include NMR and/or crystal structure data or de-novo generated structures. The obtained 3D coordinates can then be processed to generate larger set of alternative conformations for each scaffold with Molecular Dynamics ("MD") or other in silico conformational sampling techniques, which can be done with any molecular dynamics ("MD") package, for example GROMACS, NAMD or Desmond.

Figure 4:
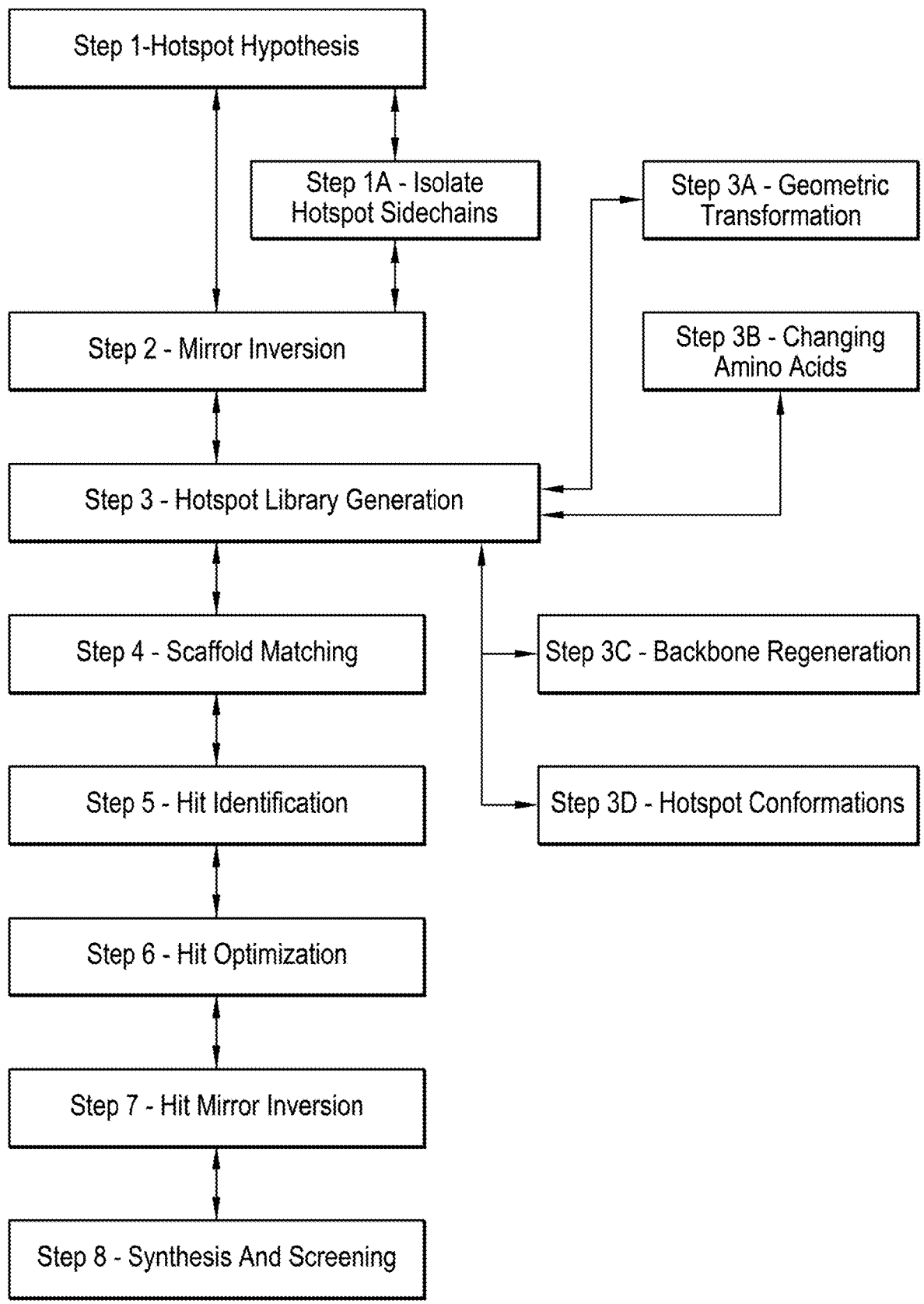
FIG. 4 includes a diagram of method steps of an in silico computing methodology for generating D-ligands that bind with an L-target.
Figure 12:
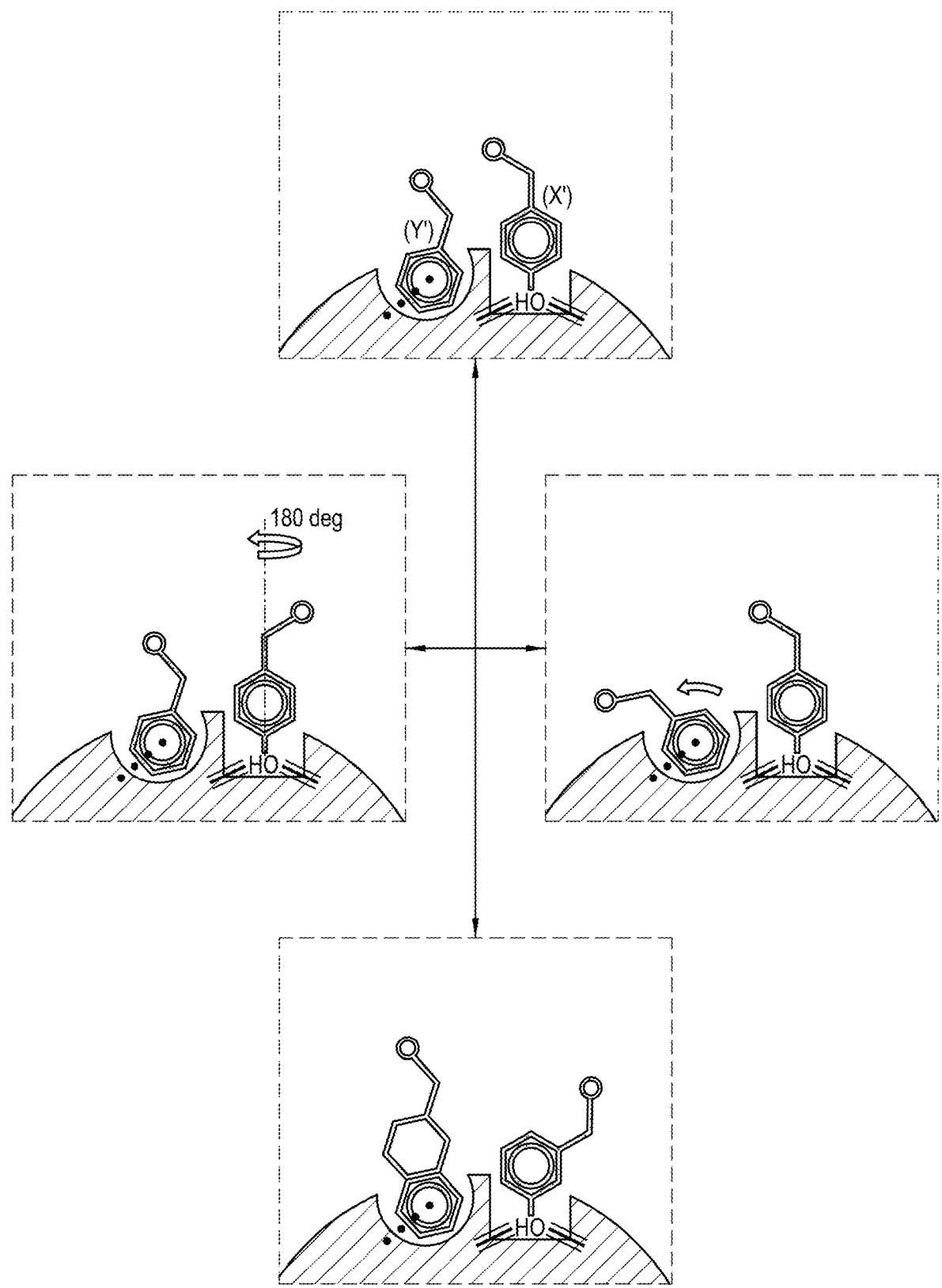
FIG. 12 includes a schematic diagram of transformations preserving hotspot side chain interaction.

FIG. 4 shows a part of the in silico methodology 300 for preparing the hotspots before the matching phase against scaffolds, which can correspond to Step 3 of FIG. 3. The methodology 300 can include various steps, depending on the chemical nature of the hotspot side chains involved. These steps may include: Step 3A (e.g., Step 3A—Geometric Transformation) for determining geometric transformations of the interacting amino acid by exploiting the internal symmetry of the hotspot side chain; and Step 3B (e.g., Step 3B—Changing Amino Acids) for modifying the chemical nature of the interacting amino acids. The steps may also include: Step 3C (e.g., Step 3C—Backbone Regeneration) for regenerating a portion or all of the backbone of the hotspot side chains that are identified in Steps 3A and/or 3B;

In FIG. 12, Step 3A can be explained on the example of a phenylalanine hotspot. If the phenyl ring is the major interaction group of the amino acid, the symmetry of the ring can be exploited. The ring can be rotated by 60, 120, 180, 240, 300 and 360 degrees around the axis perpendicular to the plane of the ring, and these rotations will preserve the interaction between the phenyl ring and the target, unless the rest of the amino-acid clashes with the target. As shown, rotating tyrosine except for the HO group, by 180 degrees preserves interactions with the target but generates new position of the carbon-alpha.

Figure 13:
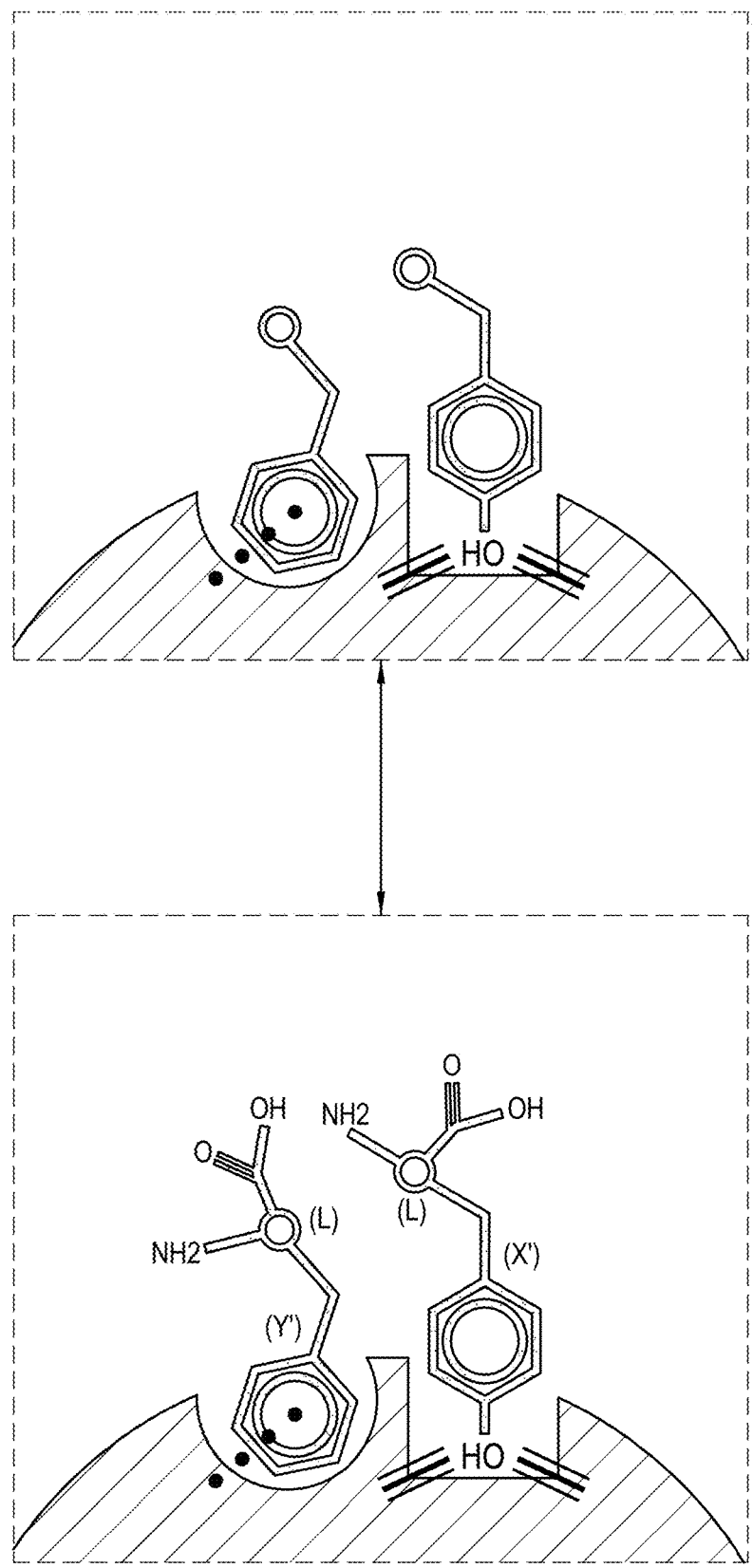
FIG. 13 includes a schematic diagram of backbone regeneration.
Figure 14:
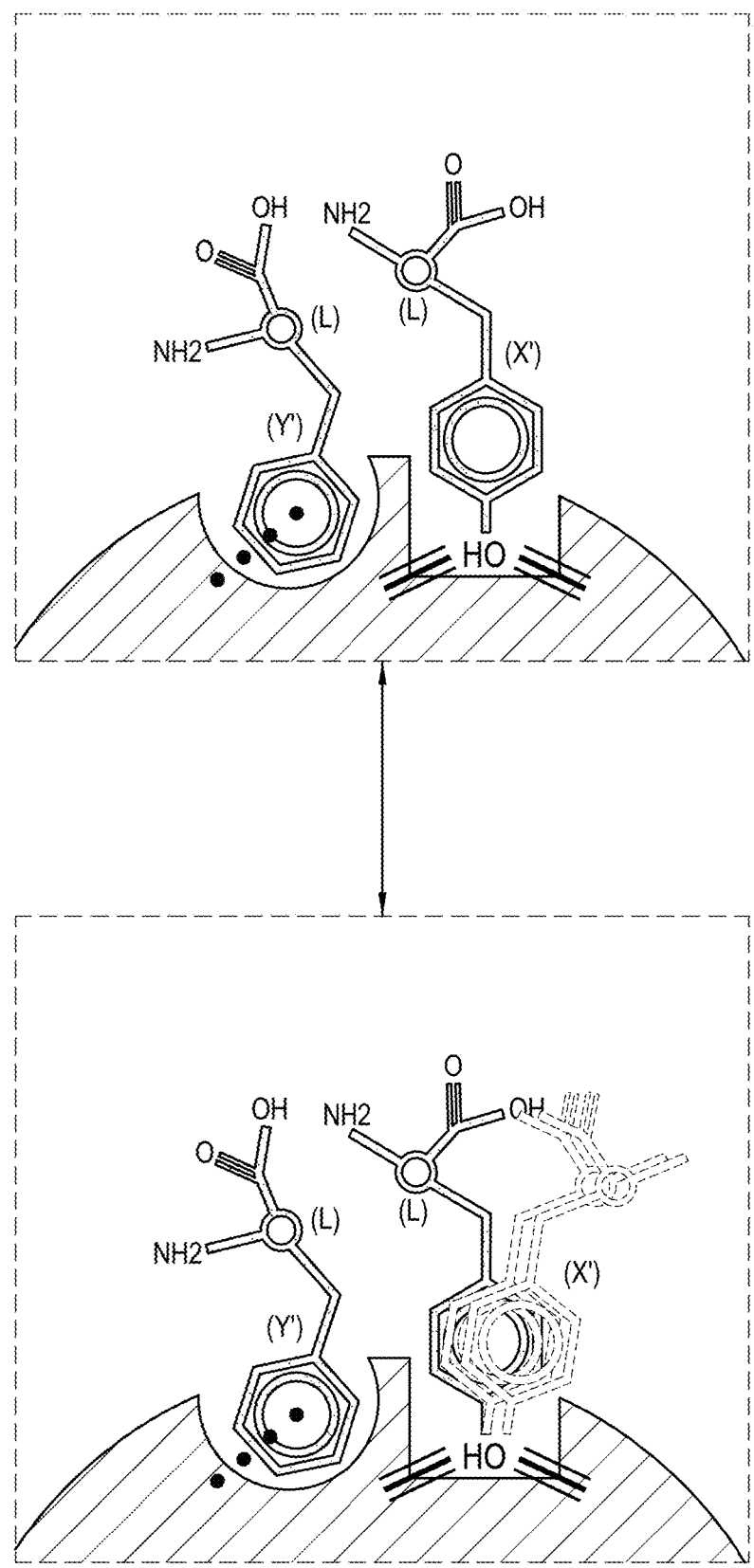
FIG. 14 includes a schematic diagram of inverted hotspot library generation.

Another transformation that preserves the interactions is rotation by 180 degrees around any axis crossing two phenyl ring carbons and the center of the ring. These symmetric transformations can be defined only for some specific side chains, while for others they are not possible.

In FIG. 12, Step 3B shows the hotspot amino acid may be replaced by another amino acid of any type, so long as the hotspot interactions with the target are preserved by such transformation. For example, phenyl ring of phenylalanine hotspot interacting with the target, may be replaced by naphthalene. The chemical nature of the interacting phenyl ring in both amino acids is similar and this transformation will only affect the position of the backbone and not the interactions with the target. Using noncanonical aminoacids can preserve the initial interaction and allow for different positions of the carbon alpha.

Any of the transformations in Steps 3A and 3B or any number of combinations of these transformations, are conducted in a manner to increase the variety in the positions of the hotspot carbon-alpha atom, which are exploited in the next step of the methodology. By introducing transformations in Steps 3A and 3B, a large library of alternative side chain positions for each hotspot can be generated while keeping the essential interactions identified in the hotspot hypothesis. Having alternative conformations for each hotspot (called a hotspot library) can increase the opportunity for finding a scaffold that matches all of the hotspots from the hotspot hypothesis. The side chains functional moieties are still reproducing the native complex interactions; however, the rest of the side chain can be changed.

Accordingly, any transformation that may result in a different location of the carbon-alpha while retaining the interactions of the side chains with the epitope can be performed. This can include all possible rotations, mutations, or the like to preserve the interactions. For example, the interactions are preserved so that if there is a hydrogen bond, the hydrogen bond interaction is preserved so that the angle and distance can be maintained for the interaction. Some change can be tolerable depending on the type of interaction; there can be a cutoff for when the change is too significant such that the interaction is not preserved. Thus, the interactions do have a degree of variability, and depending on the type of interaction and interacting atoms involved, cutoffs for interaction distances and angles can be defined based on existing experimental evidence. These are clearly known limits in the field. The plurality of the side chain positions can be visualized as the hotspot side chain library.

Step 3A represents geometric transformations, such as rotation, and Step 3B represents changing amino acid structure. However, one or both of these steps may be performed in any sequence. In some instances, only Step 3A will be performed, in others only Step 3B will be performed, and when in sequence either Step 3A or Step 3B can be performed before the other step. After these steps, the protocol can include determining whether or not the generated side chains sterically clash with the D-target and/or D-paratope and/or D-hotspot receivers. If no steric clashes are detected, the transformed hotspot side chains are further processed, such as through Step 3C, Step 3D, and Step 4 and onward. If steric clashes are present then the hotspot side chain is rejected and discarded from further processing. Steps 3A and 3B are shown in FIG. 12. As shown in FIG. 4, after Steps 3A and 3B, Step 3C (e.g., Step 3C—Backbone Regeneration) can include the process where backbone regeneration is performed so that each of the side chains belonging to the hotspot sidechain library becomes a full amino acid. This can include constructing the L-backbone starting from the side chains having the functional groups that were mirror inverted, optionally together with the mirror inversion of L-target into D-target. The L-backbone can be regenerated from the 3D structure of the functional groups binding the D-target.

Backbone regeneration works by fixing the functional groups, and allowing the amino-acid backbones to be constructed in either L or D configuration, depending on the chirality of the target protein. The process is capable of preserving the protein-protein interactions mediated by the hotspot sidechain, while simultaneously changing chirality of the carbon-alpha stereo center of the hotspot amino acids. Since this transformation is not univocal, the process generates a large set of backbone conformations, which increases the size of the hotspot library and chances of finding a scaffold that matches the hotspots in Step 4. FIG. 13 shows the backbone regeneration. Also, L-backbones can be regenerated from sidechain structures inverted through the mirror, for all variants generated in Step 3 (e.g., Steps 3A and/or 3B). The figure shows the L chirality is regenerated while maintaining the original interactions between the side chains and epitope of the D-target.

Figure 6:
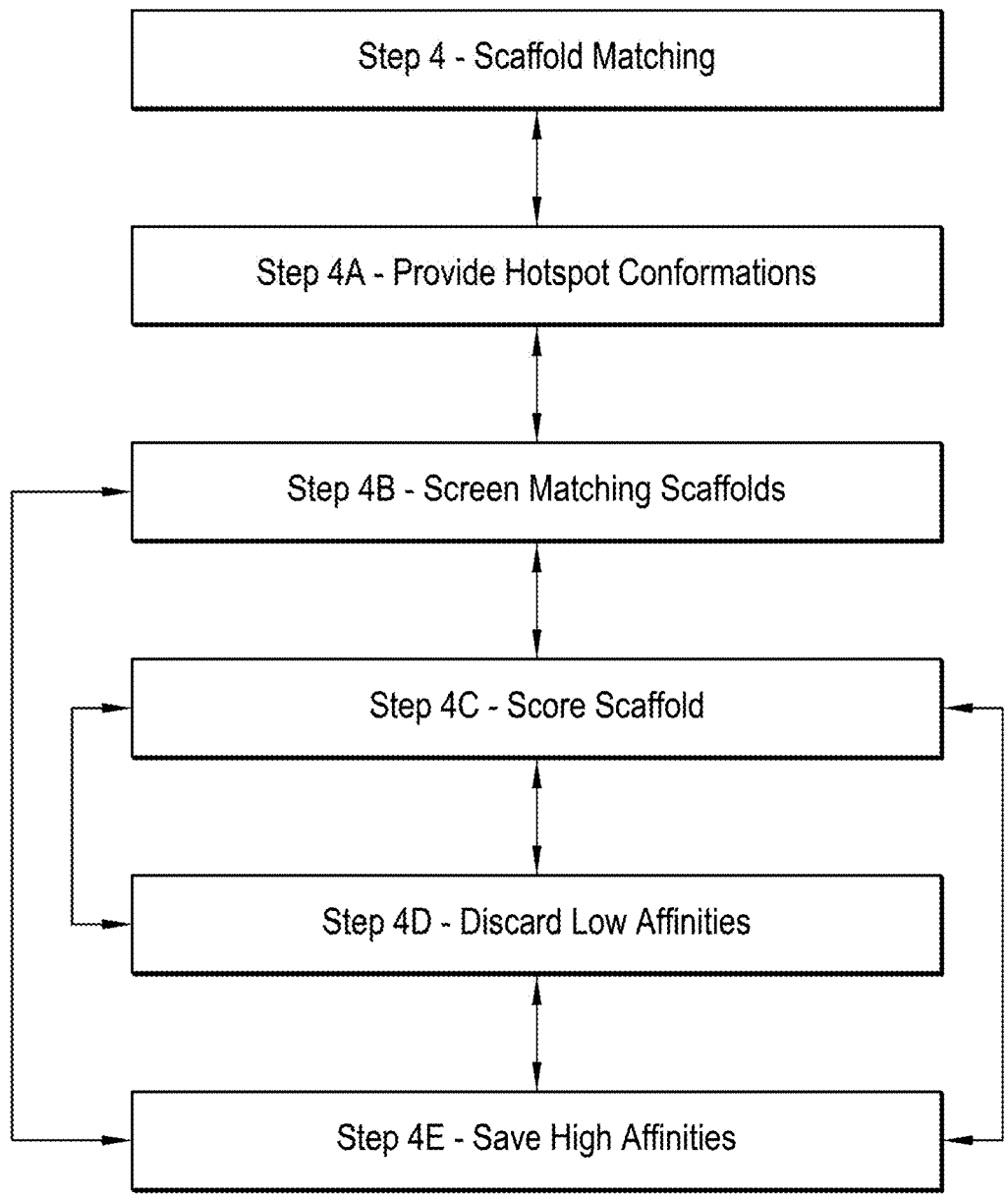
FIG. 6 includes a diagram of method steps of an in silico computing methodology for scaffold matching.

Step 3C can include backbone regeneration as shown in FIG. 13, which can involve complementing the hotspot sidechain structures with amino-acid backbones The regenerated backbones have L-chirality at every hotspot side chain whenever the target presents D-hotspot receivers and/or D-paratope and/or the entire D-target. Depending on the amino-acid type, multiple rotamers are allowed, and all of these conformations are included, multiplying the number of hotspot structures belonging to the hotspot library. Conventional notion of rotamer consists of changing the position of the sidechain by fixing the backbone. Here instead, in order to preserve the interaction of the sidechain with the target, the backbone position is changed.

Once the hotspot amino-acid structures have been completed with backbones they are tested for steric clashes with the D-hotspot receivers and/or D-paratope and/or D-target. The inversion of the chirality of the backbone of the hotspot amino-acids may often result in structures that no longer allow the hotspot sidechains bind in the same way as in the original complex. Hotspot amino acids that clash sterically with the target are rejected from the hotspot library. In one example, if a structure of a hotspot amino acid clashes with the D-target or other hotspot amino acid, the hotspot amino acid structure can be rejected. In another example one can use a molecular visualization tool to detect the clashing hotspot amino acids belonging to adjacent hotspots and selectively reject those entries. In all cases only those hotspot amino acid structures that do not directly clash with the D-target are selected and saved for further processing.

FIG. 4 also shows the Step 3D (e.g., Step 3D—Hotspot Conformations) for generating the final hotspot library. This step includes additional modifications to all conformations in the hotspot library.

FIG. 14 illustrates additional variation of the hotspot amino-acid conformations that is allowed in order to further increase the variation of the hotspot library. At this point, transformations that may slightly change the position of the hotspot sidechains, such as redocking, minimization, molecular dynamics, are allowed. This can generate hundreds of conformations or more for the hotspot amino-acids In one example, redocking of the hotspot amino acids can create additional conformations for the hotspot library. In one example, the hotspot library can represent hundreds or more different conformations that retain the original hotspot side chain interactions with the epitope of the D-target.

Any hotspot amino acid can be diversified as described herein and selected for further processing. The diversification results in the final hotspot library.

In Step 3D, the hotspots with regrown L-backbones, so called inverted hotspots, are allowed to vary position, without losing interactions of the hotspot side chains with the D-target. The result of Step 3D can include a larger set of hotspot backbones in the hotspot library. Transformations that can be applied at this point include re-docking of the hotspots on the D-target. Molecular dynamics of the hotspot amino acids with the D-target can be performed. Also, any other conformational sampling technique that can improve conformational sampling of the hotspot conformations with respect to the D-target hotspot receivers can be employed. Every conformation obtained in the Step 3D can be tested for the preservation of the hotspot-hotspot receiver interactions (e.g., hotspot-epitope interactions), before being added to the hotspot library database (e.g., database 201).

In one aspect, any hotspot side chains of Steps 3A and 3B and hotspot amino-acids generated in Steps 3C and/or 3D may be excluded if they do not properly dock with the D-target epitope, e.g. docking does not recreate original interactions. If at any step a hotspot conformation clashes with the D-target, then that conformation is rejected from the hotspot library database. Otherwise, the hotspot conformations can be saved and selected for further processing.

FIG. 4 also shows Step 4 (e.g., Step 4—SCAFFOLD MATCHING) for grafting the inverted hotspots on a L-scaffold in order to identify the scaffolds that may possibly have hotspots that interact with and bind to the D-hotspot receivers of the D-target and/or D-epitope. Accordingly, scaffolds obtained in this step are entered into the database 201 of the computing system 299 so that the in silico screening can be continued. The matching process results in a scaffold that can acquire simultaneously all hotspots from the hotspot hypothesis, in one of their allowed conformations that are stored in the hotspot library database. When the hotspots are grafted on the scaffold, they should be able to present the sidechains in a way that mimics the original hotspot interactions and preserve a conformation of both side-chain and backbone atoms which resembles that of natural occurring proteins.

In one aspect, Step 4 can include: A) identifying L-scaffolds that match with the hotspots; and B) grafting the hotspots onto the matching L-scaffolds to generate the scaffolds for further processing. This is shown in FIG. 15.

The scaffolds used for the scaffold-hotspot library matching algorithm may also be obtained by iterative design, for instance, by performing molecular dynamics simulations, or any other conformational sampling technique, applied on the scaffolds already stored in the database. This is a part of the in silico methodology 300 for matching hotspots against scaffolds, and selecting appropriate scaffolds. FIG. 15 shows the hotspot library being matched with a potential L-scaffold, and the matching L-scaffold being selected. The process allows for the computing system 299 to match the hotspot library with the L-scaffolds. The hotspot library can provide a large number of conformations for each hotspot, which increases the chances of finding a good matching L-scaffold. As shown in FIG. 15, best matching hotspot conformations are selected for each hotspot. However, it should be recognized that only one scaffold is shown, and other scaffolds can have different sequences and three-dimensional structures.

Generally, low energy L-hotspot conformations can be created in Step 3, and screened for matching with the scaffolds. In one example, the Rosetta hotspot matching algorithm can be employed here. There are other algorithms that perform similar function and can be used for the purpose, such as the Medit package. The hotspot matching algorithm can include grafting the hotspots onto scaffolds, whenever steric constraints allow for it. The matching scaffold determination may also vary neighboring amino acids in order to improve in-silico predicted affinity (score) and minimize molecular clashes of the scaffold/D-target complexes. As such, matching scaffolds are identified and saved as hits for further processing or refinement.

An iterative process can be implemented for scaffold matching (e.g., Step 4), such as shown in FIG. 6. Here, the individual conformations for each hotspot from the hotspot library obtained in Step 3 are provided for scaffold matching. As such, Step 4A (e.g., Step 4A—Provide Hotspot Conformations) includes providing the hotspot conformations for scaffold generation. Step 4B (e.g. Step 4B—Screen Matching Scaffolds) can include screening for scaffolds that can have the inverted hotspots grafted. The screening can involve interface redesign around the grafted hotspots. The screening in Step 4B can result in data, e.g. predicted protein-protein complexes, which can be ranked and scored. As such, Step 4C (e.g., Step 4C—Score Scaffold) can be implemented to give each of the scaffold designs a relative score. Any protein-protein interactions scoring functions can be used (e.g. Rosetta scoring function). The score can be indicative of the binding affinity and allow for selection of L-scaffolds with grafted hotspots that have higher binding affinities, and discarding of entities with lower binding affinities. Accordingly, the low binding affinity can be discarded in Step 4D—Discard Low Affinities. The high affinities can be saved in Step 4E—Save High Binding Energies. The saved high affinity entities can be selected for further processing. The L-ligands with high binding affinity and optimized interface are called hits (or L-hits) and may be used for further mutation and variance. The Steps 4A-4E can be implemented in the scaffold matching module 284 of the computing system; however, unique modules for each step may be utilized.

FIG. 4 also shows Step 5 (e.g., Step 5—HIT IDENTIFICATION) for deciding which of the matched scaffolds can be called hits and be taken for further analysis. Accordingly, Step 5A can include obtaining 3D coordinates of potential L-ligand scaffolds that may bind with the D-target. The coordinates of the L-scaffolds that have the hotspots grafted are obtained from Step 4—Scaffold Matching (e.g., Step 5A—Obtain Matched Scaffold Data from Database). The scaffold can then be selected for further analysis based on a number of criteria and constraints. For example, one constraint can include available computational resources. In principle all matched scaffolds could be further optimized, however this can be computationally expensive. For this reason, some matched scaffolds can be pruned. Neglecting some of the matched scaffolds can be done based on a number of criteria that can help select more promising scaffolds. One such criterion can be based on the structure of the complex between the target and the matched scaffold, for instance a threshold in change of the solvent accessible surface upon binding can be used. The complex score can also be used as a threshold. Number of mutations in the scaffold can also be used as a threshold. Another parameter that can be used to select promising hits can be the ratio of score and the number of mutations. Another important threshold can be the similarity of the grafted inverted hotspot sidechains to the original mirror inverted hotspot sidechains. If the sidechains were distorted during grafting, the resulting scaffold can be rejected, otherwise it can be accepted. The values of the thresholds only depend on the computational resources available. The scaffolds with the least advantageous set of parameters can be excluded. The thresholds can be implemented and applied to the set of matched scaffolds in step 5B—Filter Hits. The filtered hits can then be saved for further processing in step 5C—Save Hits. The Steps 5A-5C can be implemented in the hit identification module 285 of the computing system; however, unique modules for each step may be utilized.

Figure 17:
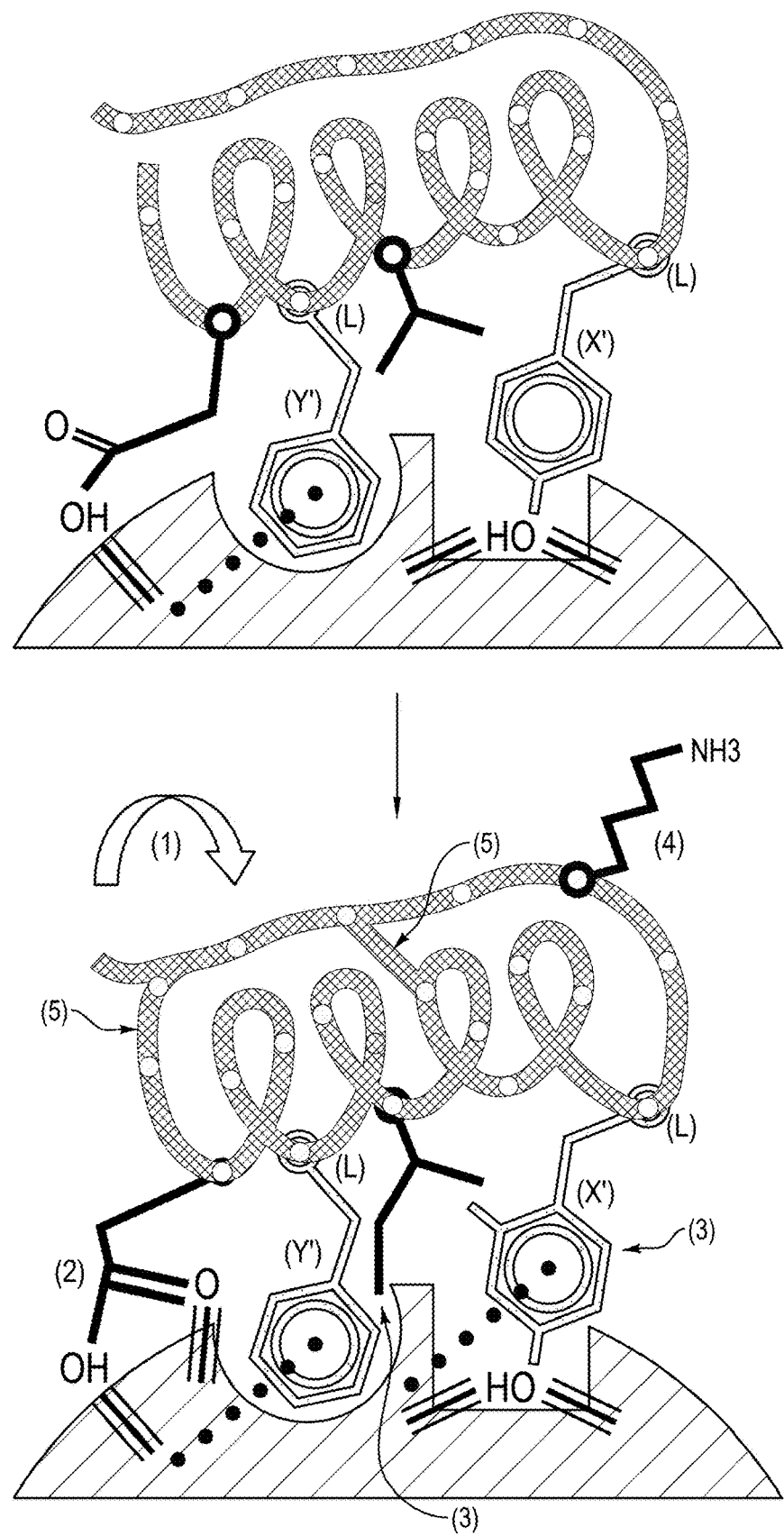
FIG. 17 includes a schematic diagram of hit optimization.
Figure 18:
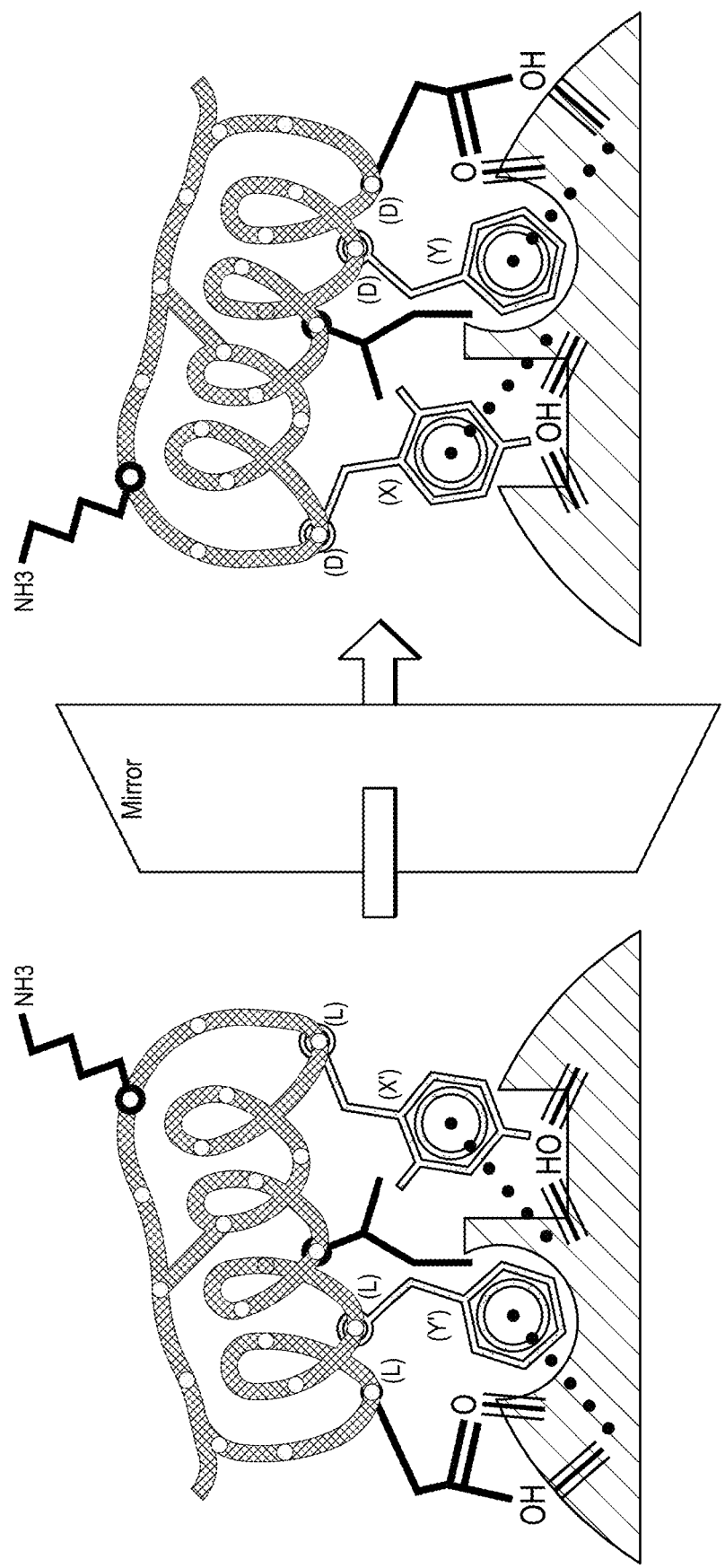
FIG. 18 includes a schematic diagram of mirror inverting the optimized hits.

FIG. 4 also shows Step 6 (e.g., Step 6—HIT OPTIMIZATION) for optimizing the hits obtained in Step 5. Hit optimization can include one or more rounds of optimization protocols performed in the computing system 299. A single round can include: 1) redocking the hit with the D-target, where the hit sequence and structure is not changed; 2) regeneration of low energy sidechain conformations (re-packing); 3) creating single/double/triple mutants at the interface or direct surroundings; 4) creating mutations that improve solubility and/or stability; 5) create cyclisation modifications; 6) removing mutations that do not improve scoring function and 7) propagating the hit with molecular dynamics, or any other molecular dynamics/Monte-Carlo method that allows to explore the phase space of the protein complex. Protocols 1, 2, 3, 4, and 5 are illustrated in FIG. 17. The reason for including point 6 is that any transformation of the in silico complex may render certain previous mutations irrelevant. Since it is preferred to keep the number of mutations as low as possible, and only include the necessary mutations, Step 6 can be performed at every point of the Hit Optimization protocol. The molecular dynamics of protocol 7 can be performed as generally known in the art.

Figure 8:
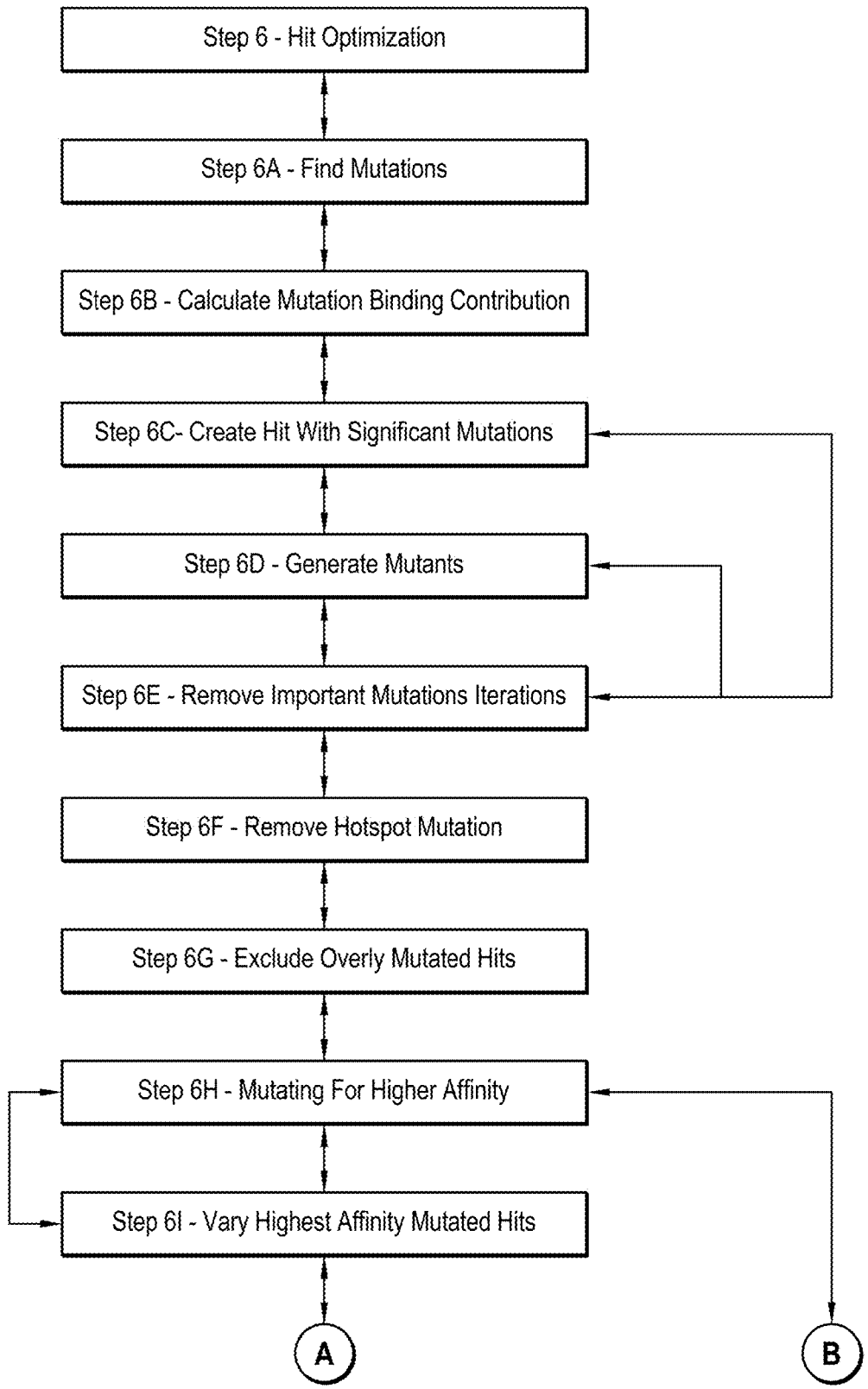
FIG. 8 includes a diagram of method steps of an in silico computing methodology for hit optimization.
Figure 8:
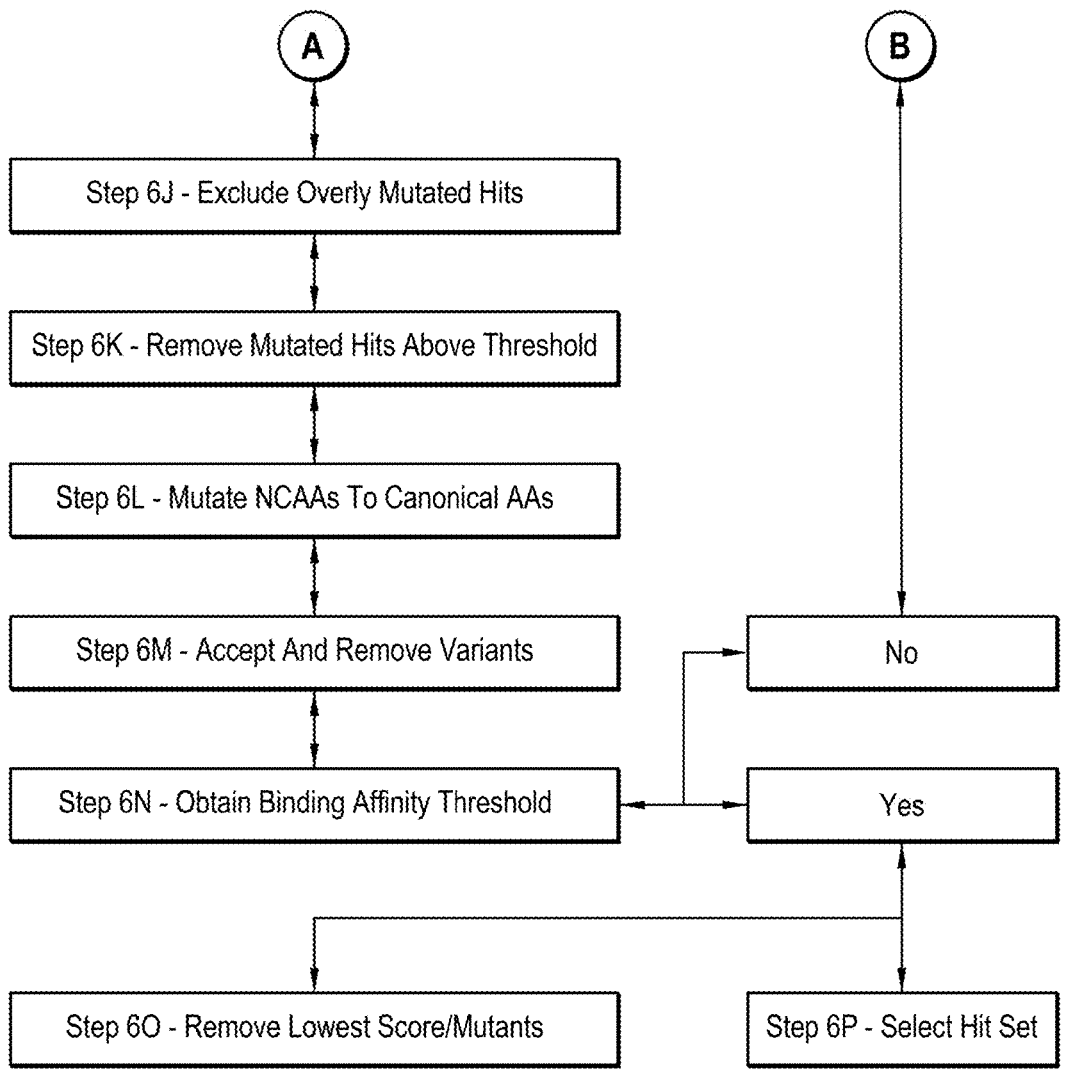

FIG. 8 shows an in silico methodology for hit optimization or improving initial hotspot-grafted scaffolds that were designed in Step 5 to bind with the D-target, which can correspond with Step 6 of FIG. 4. Step 6 can include further modifying hits coming from Step 5—Hit Identification, to develop an improved mini-library (e.g., containing designs with further improved scoring function, solubility, stability or other physic-chemical properties). Step 6A (e.g., Step 6A—Find Mutations) can include finding mutations between the hit and the wild type scaffold from which the hit derives. The matching phase of hit identification of Step 5 can introduce mutations via hotspot grafting and accessory mutations to amino acids surrounding the hotspots that improve the hit scoring function for binding with the D-target. Here, the protocol can include simply looking at the sequences of both the wild-type scaffold and the hit and identifying the mutations, such as by regular alignment. As such, differences between the initial wild-type scaffold and the hit can be determined in Step 6A—Find Mutations. Step 6B can include calculating the contribution to the binding score for every of the mutations identified in Step 6A compared with its corresponding back-to-wild-type mutation (e.g., Step 6B Calculate Mutation Binding Contribution). In case the contribution of a certain mutation to the score is negligible, the mutation may be removed and wild-type scaffold amino acid may be restored at the position. Mutations with significant contribution to binding score may be retained. In Step 6B, contributions for all mutations are calculated and sorted from the most to the least significant. The binding affinity can be estimated with various methods and software. In one non-limiting example, the method can be implemented in Rosetta as the DDG score calculation module. However, any affinity calculation module or protocol can be used. In one example, any other method that predicts binding affinity between the hit and the D-target can be used. The calculated binding affinity, can be referred to as the DG, and the change of DG upon mutation can be referred to as DDG=DG_mut—DG. DDG more than −0.5 RU is marked as rejected, a DDG greater than −2.0 RU and less than −0.5 RU is marked as important, and a DDG less than −2.0 RU is marked as a hotspot. Step 6C includes creating a design, which includes a structure where all rejected mutations (e.g., DDG>−1) are mutated back to wild-type (i.e. BTW) (e.g., Step 6C—Create Hit with Significant Mutations). Step 6D includes generating mutants starting from the hit with the significant (i.e. hotspot and important) mutations only and implementing single BTW mutations on positions marked as important mutations (e.g., Step 6D—Generate Mutants). Step 6D can be iterated until no important mutations are left in Step 6E—Remove Important Mutations Iteration. This results in hit that only contains hotspot mutations. The hotspot mutation only containing hit can then be mutated to remove the hotspots through single BTW mutations until the wild-type scaffold is achieved (e.g., Step 6F—Remove Hotspot Mutation). All combinations of BTW hotspot mutations are included and stored. Since these mutants are not supposed to bind, they are negative controls for the following in vitro experiments. The 3D structures of all mutants are generated using standard software methods present in all molecular modeling packages like Maestro, Rosetta, Pymol, MOE. The set of hit designs thus obtained that have more than 15 mutations and/or more than 50% of amino acids being mutated, preferably more than 12 mutations and/or more than 40% of amino acids being mutated and most preferably more than 10 mutations and/or more than 30% of amino acids being mutated are excluded, and thereby overly mutated hits and designs are excluded (e.g., Step 6G—Exclude Overly Mutated Hits). With this parameter the size of the library is reduced to a reasonable number, where too many hits can be a limiting factor. The hit designs with less than or 15 mutations and/or less than or 50% of amino acids being mutated, preferably with less than or 12 mutations and/or less than or 40% of amino acids being mutated, and most preferably less than or 10 mutations and/or less than or 30% of amino acids being mutated are selected.

After the overly mutated hits designs are excluded, the methodology begins with a protocol for generating a set of further improved ligands that can be converted to the mirror inverted D-ligands.

Step 6H can include mutating the selected hit designs to find higher affinity ligands (e.g., Step 6H—Mutating For Higher Affinity). See FIG. 17. This can include mutating the selected hits designs with single and/or double and/or triple mutations in the paratope, hotspots, and/or side chains, which can be repeated and analyzed for optimized scoring function in complex with the D-target. The complexes with most improved binding score are identified. The mutated hit designs can be accepted when the scoring function has been improved preferably by 5%, more preferably by 8%, most preferably by 10% per mutation made compared to the starting hit.

Step 6I can include protocols to vary the mutated hits from Step 6H with highest predicted affinity (e.g., Step 6I—Vary Highest Affinity Mutated Hits). The hits can be selected with a threshold of 50%-100%, more preferably within 60%-100% and most preferably within 70%-100% of the maximum score within the given hit scaffold class. The threshold is used in order to select only the best designed hits per scaffold family for further modifications. The selected hits can then be redocked using any docking algorithm and their paratopes redesigned by again being processed through Step 6H, with the single and/or double, and/or triple mutations in the paratope. The resulting hits are called optimized hits.

Once Step 6I has been performed, optionally with one or more iterations, designs that do not fulfill various general and system specific criteria can be excluded. The varied, mutated hit designs can be refined by excluding overly mutated hits (e.g., Step 6J—Exclude Overly Mutated Hits). The overly mutated hits can be excluded if they have more than 15 mutations and/or more than 50% of mutations, preferably more than 12 mutations and/or more than 40% of mutations, and most preferably more than 10 mutations; and/or more than 30% mutations. Mutants that have a small interaction surface or SASA of less than 400 Angstroms squared (Å$^2$), more preferably less than 600 Å$^2$, most preferably less than 800 Å$^2$ can be neglected.

The optimized hits can be further refined by removing designs with a parameter value less than a threshold. Here, the parameter can be the in silico predicted binding affinity per number of mutations compared to wild-type scaffold being less than 5% of the predicted binding affinity (e.g., the threshold), preferably less than 10% and most preferably less than 15% (e.g., Step 6K—Remove Inefficient binders).

The optimized hits may be still further refined by mutating any of the non-canonical amino acids ("NCAAs") back to canonical amino acids ("AAs") as in Step 6L—Mutate NCAAs to Canonical AAs. In case this change does not significantly affect the in silico predicted binding energy or affinity, canonical amino acids can be preferred. Here, if the in silico predicted binding affinity increases upon mutation by less than 5% of the maximum score per family, more preferably by 8% or most preferably by 10%, then the process can accept and remove the NCAA variant in Step 6M—Accept and Remove Variants.

Once the improved hit designs have been refined, a determination can be made of whether or not the optimized hits family reached a certain binding affinity/scoring function threshold. This can be Step 6N—Obtain Binding Affinity Threshold. This threshold depends on a particular scoring function used, and can also be decided based on the number of sequences that can be synthesized. If one has resources to synthesize more sequences, the threshold can be more permissive. It can also be decided depending on the D-target epitope, since some epitopes will result in better scores on average. The threshold can be defined based on the best scores reached per scaffold family. The total best score can be used as a reference, and only scaffold families that reached 50%, more preferably 60% and most preferably 70% of that score are identified. Has a scaffold family reached the threshold? If the answer is no, then the process can be iterated starting with Step 6H. If the answer is yes, then the process can continue.

The continued process can include even more refinement of the optimized hits if it is determined the set is too large by removing the structures with lowest score per number of mutants (e.g., score/n_mut), which can be Step 6O (e.g., Step 6O—Remove Lowest Score/Mutants). This can be done until a desired number of structures are obtained.

Accordingly, certain optimized hits designs can be selected (e.g., Step 6P—Select Hit Set).

The Steps 6A-6P can be implemented in the hit optimization module 286 of the computing system; however, unique modules for each step may be utilized.

All these different steps can be taken in various orders with the goal of proving the robustness of the hits upon slight change of coordinates, providing a panel of possible variants by mutating amino acids in the interface, and optimizing the score. The variations in the optimization phase can include modulating the hit to actually have less mutations while keeping a good score. In part, less mutations can be beneficial because the number of mutations increases the risk of misfolding of the scaffold.

Having as few mutations as possible can be a goal of the optimization phase, next to improving the score which can correlate with binding affinity. Thus, it can be advantageous to optimize the score/mutation ratio, where a higher score and lower mutation is desirable, instead of just optimizing the score which does not take into account the probability of folding in a specific structure.

In one aspect, if the hit is highly hydrophobic, it can be advantageous to introduce certain mutations that increase water solubility. These water solubility mutations can be more water soluble amino acids (e.g., lysine or glutamic acid), which can be introduced into locations that do not interact with the epitope of the D-target (FIG. 17, modification 4). It can be advantageous for the hit and eventually D-ligand to be water soluble. As such, mutations to water solubilizing amino acids can be advantageous, when they do not interfere with the binding interactions. In one aspect, it can be beneficial to introduce amino acids increasing water solubility to the N-terminus and/or C-terminus.

In one aspect, cyclisation introducing mutations can be employed. These amino acids can form covalent bonds with other amino-acids or backbone termini, in order to stabilize the folded structure of the scaffold (FIG. 17, modification 5).

Additionally, Step 6 can include a step—Molecular Structure Optimization—that can directly act on the structure of the optimized hits—D-target complex by performing molecular dynamics, molecular minimization or using other phase space sampling methods. If performed, it can occur before or after the steps in the protocol of FIG. 8 or at any time during or between the protocols of FIG. 8. For example, the optional Molecular Structure Optimization can occur prior to any loop of back-to-wild-type mutations, redocking, single/double/triple mutation designs, or other process of Step 6. The Molecular Structure Optimization can result in hits with increased binding score per number of mutations. In one aspect, the hit optimization of Step 6 can include a loop of back-to-wild-type mutations, redocking, and mutation designs (e.g., single mutation design, double mutation design, and/or triple mutation design), which back-to-wild-type mutations, redocking, and mutation designs can be performed in any order and any number of times per loop. The loop can take any step shown in FIG. 8, and loop back to any preceding step. Then the back-to-wild-type mutations, redocking, and mutation designs can be implemented for hit optimization. The method can result in any number of hit optimization loops. The hit optimization loops in can be performed in any order and in any manner described to obtain optimized hits that have increased binding scores per number of mutations. Optimally, maximized binding scores per number of mutations for an optimized hit. By performing the Hit Optimization protocol, one finds that the hit population does not change anymore, indicating that all the relevant and possible hit variation that retains high score and optimally low number of mutations has been explored.

FIG. 4 also shows Step 7 (e.g., Step 7—HIT MIRROR INVERSION) for performing a mirror inversion of the optimized hits to their corresponding D-ligands. The mirror inversion protocol can be performed as described herein or generally known in the art. The mirror inversion can be for the hit with or without being docked in the D-ligand. As such, the hit can be mirror inverted alone to get the D-ligand (as in FIG. 3, step 7) or in complex with the D-target to get the L-target/D-ligand complex. FIG. 18 shows the hit mirror inversion of the structure of the optimized hit. Here, it can be seen that all of the chiral centers are inverted (e.g., L to D, X' to X, and Y' to Y). In the D-ligand, one or more amino-acids are (D)-amino acids. However, some amino acids may be L amino acids. In the case the hotspot side chain has a stereo center, the hotspot becomes an epimer of the original hotspot amino-acid, with only the carbon-alpha stereo center inversed in the D-ligand.

Once the optimized hit designs are selected, their sequences can be mirror inverted to obtain the D-ligands in the in silico methodology in accordance with the invention. For example, if the hit has the sequence GLFGHQA, then the corresponding D-ligand with a mirror structure will have a sequence GlfGhqa, where capitals are used for L-amino acids and lower case letter for corresponding D-amino acids. As such, the L to D conversion for an amino-acid side-chain that is not chiral is trivial. In case the amino-acid side chain is chiral (for example Threonine or Isoleucine), then attention needs to be paid to also inverting the side chain chiral centers. Any process of mirror inversion can be performed. Accordingly, the D-ligand can be obtained by performing the mirror inversion of the chirality of the L-amino acids in the optimized hit designs to the D-amino acid isomer (e.g., Step 7). This mirror inversion can be done in hit mirror inversion module 287, which may be the same or different from mirror inversion module 282.

FIG. 5 illustrates the computing system 299 with computing modules configured to perform the steps of FIG. 4. The computing system 299 can include a database 201 that can read/write with the modules, where data can be saved to or accessed from the database 201 to manipulation in the modules, and the data obtained from such manipulation can be saved in the database 201. As shown, the computing system 299 includes a hotspot hypothesis module 280 that can be coupled to or include sub-modules, which can read and write to the database 201. The hotspot hypothesis module 280 can be configured to implement hotspot hypothesis protocols in accordance with the principles described in connection to Step 1. Also included is a hotspot amino acid identification module, large amino acid identification module, hydrophobic amino-acid identification module, and/or extra paratope amino acid identification module that can be configured to implement the hotspot hypothesis protocols. The computing system can include a hotspot isolation module 281 configured to implement isolating hotspot amino acid sidechains from the rest of the ligand to leave the hotspot side chains in accordance with the principles described herein in connection with Step 1A. The computing system can include a mirror inversion module 282 configured to implement in silico mirror image inversion of the L-hotspots amino acid side chains and of the L-hotspot receivers and/or of the L-paratope and/or of the L-target in accordance with the principles described herein in connection with Step 2. However, at any stage of the process the system can be mirror inverted with the mirror inversion module 282. The computing system can include a hotspot library generation module 283 configured to implement in silico hotspot amino acid library generation in accordance with the principles described herein in connection with Step 3. The hotspot library generation module 283 may also be configured to implement Step 3A, 3B, 3C, and/or 3D or separate modules can be included. The computing system can include a geometric transformation module 283*a* configured to implement in silico geometric transformation of the hotspot amino acid side chains in accordance with the principles described herein in connection with Step 3A. The computing system can include a changing amino acids module 283*b* configured to implement in silico changing amino acid side chains of the hotspots to other amino acid side chains in accordance with the principles described herein in connection with Step 3B. The computing system can include a backbone regeneration module 283*c* configured to implement in silico backbone regeneration for the hotspot amino acid side chains in accordance with the principles described herein in connection with Step 3C. The computing system can include a hotspot conformation module 283d configured to implement in silico generation of alternative hotspot conformations in accordance with the principles described herein in connection with Step 3D. The computing system can include a scaffold matching module 284 configured to implement in silico grafting the amino acid side chains of the hotspots to scaffolds in accordance with the principles described herein in connection with Step 4. The computing system can include a hit identification module 285 configured to implement in silico identification of hits from the hotspot-matched scaffolds in accordance with the principles described herein in connection with Step 5. The computing system can include a hit optimization module 286 configured to implement in silico optimization of hits to identify hits to be inverted to D-ligands in accordance with the principles described herein in connection with Step 6. The computing system can include a hit mirror inversion module 287 configured to implement in silico mirror inversion of hits to D-ligands accordance with the principles described herein in connection with Step 7, which may be the same or different from mirror inversion module 282.

It is noted that Steps 1, 2, 3, 4, 5, 6, and 7 can include sub-steps that are performed computationally, such as those described herein or developed in order to facilitate the protocols described herein.

Accordingly, optimized hits can be inverted to the D-ligand that will bind with the L-target. One or more of the D-ligands can be selected that are suitable for synthesis. The D-ligands that are selected for synthesis can be good or bad binders (negative controls) with the L-target.

FIG. 4 also shows Step 8 (e.g., Step 8—SYNTHESIS AND SCREENING), which can include real synthesis and in vitro screening of the D-ligands for binding with the L-target to confirm L-target/D-ligand complex formation. Also, the binding affinities and other relevant experimental data of the D-ligand binding the L-target can be measured.

The D-Ligands that were obtained by the in silico methodology can then be synthesized and screened in vitro for binding with the L-target. The in vitro screening can be done via ELISA, competition ELISA, Octet, surface plasmon resonance or any other technique that can detect specific binding of a peptide to a protein.

Generally, the final D-protein libraries are generated by inverting the chirality of every amino-acid in the L-protein libraries. These libraries are then synthesized using standard peptide synthesis and tested for binding. However, any method of synthesis and screening the D-proteins for binding against the L-target can be performed.

Additionally, the methodologies described herein can be modified to design D-ligands for any L-target protein. The L-target protein can be a receptor, it can be any protein or any other substrate for which it is possible to formulate a scoring function for interaction with a protein. The methodologies described herein provide significant flexibility in the computational protocols for obtaining the D-ligand library. This allows for the D-ligand library to be designed with a distribution of binding affinities per D-ligand scaffold family and with the desired final number of compounds for the screening. The distribution of binding energies can be provided with binding energies over a certain threshold. The D-ligands can be designed with minimum mutations. As such, the D-ligand scaffold families can include a plurality of D-ligand proteins that have increased binding energies to the L-target protein while minimizing the number of mutations.

Moreover, the target does not have to be a protein. The target can be a nucleic acid, such as a DNA strand for example. The only requirement is that the scoring function is defined for predicting binding of L and D peptides with this kind of target.

In one embodiment, the methodologies described herein can be performed with any starting L-ligand protein or polypeptide or set of polypeptides that binds with any L-target protein. The starting L-ligand can have any binding affinity for the L-target. As such, some L-ligands with low binding energy can be processed through the in silico methodologies in order to obtain strongly binding D-ligands based thereon. Also, some L-ligands with high binding energy can be processed through the in silico methodologies in order to obtain D-ligands based thereon. Accordingly, the methodologies described herein can allow for in silico development of a potent D-ligand by starting from a micromolar or nanomolar binder L-ligand.

In one embodiment, the in silico methodologies described herein allow for the ability to design L-Target/D-ligand complexes using experimental structures of the ligand and target. This is a significant advancement in the art of peptide ligand design, and some beneficial and surprising and unexpected results are obtained. This can include the in silico methodologies providing for computational conversion of L-hotspots that bind the L-target into D-hotspots that bind the L-target by preserving interacting groups of the L-hotspots and L-target (e.g., L-hotspot receivers).

Additionally, it is surprising and unexpected that the in silico methodologies allow for using L-proteins for designing D-proteins, which also includes the use of L-protein data bases (e.g., public or private Protein Data Bases) for designing the D-ligand proteins.

Also, it is surprising and unexpected that the in silico methodologies presented here can design D-peptides with a probability of finding a binder (i.e. a hit rate) large enough so that a synthesis of small D-peptide library would be sufficient. Since D-peptides are difficult to be directly screened for through display technologies, this is a very important and surprising finding. The D-ligands that bind with the L-target to a sufficient degree, which can vary depending on the L-target or desired binding, can provide a hit, and that D-ligand can undergo further screening for confirmation of forming a D-ligand/L-target complex. The size of the libraries allows for synthesis of soluble libraries (few hundred peptides). The screening can use only the L-target or cells or cellular components including the same. Any ligand-target screening can be used with the D-ligand libraries.

In one embodiment, the present invention can use a methodology where only scaffold mirror inversion is conducted. As such, the computing methodologies can use the invention described herein but with the target being an L-target and designing D-ligands by matching mirror images of scaffold structures against the inverted hotspots.

Figure 4A:
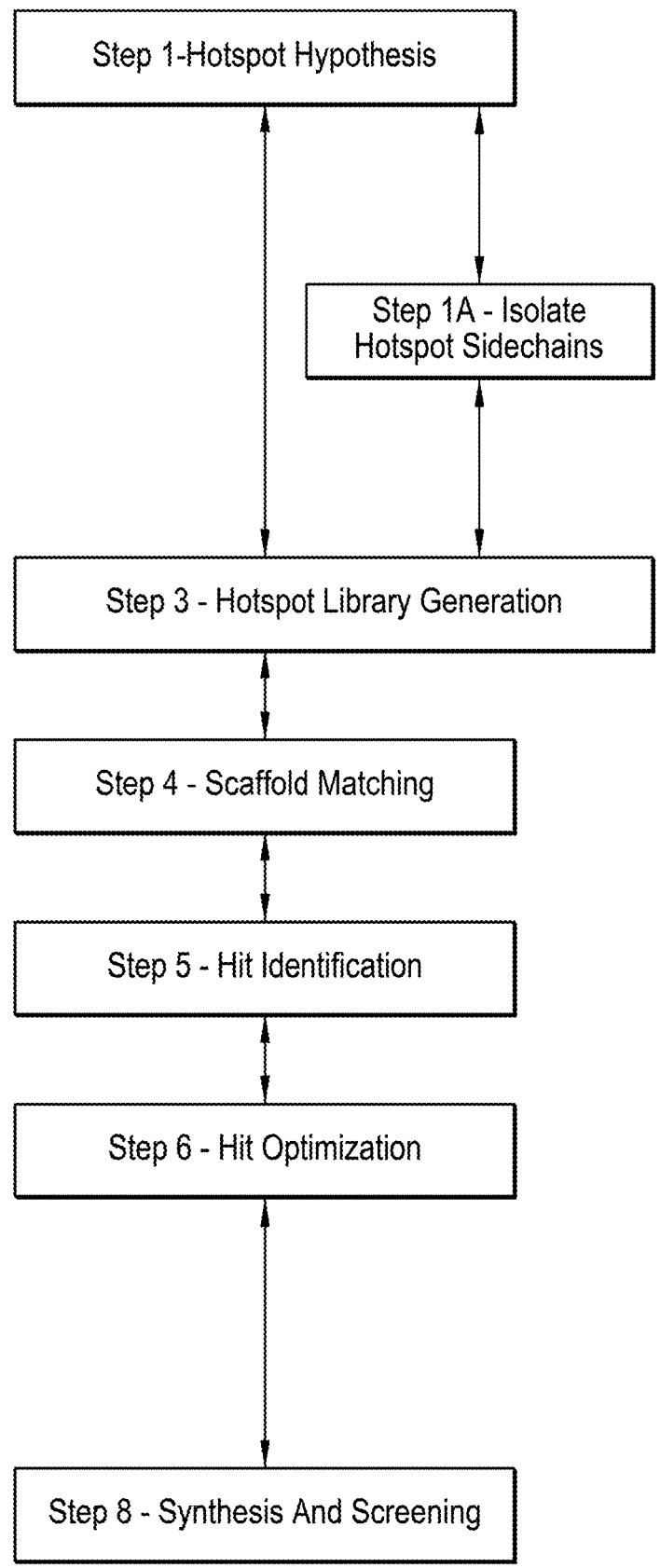
FIG. 4A includes a diagram of method steps of an in silico computing methodology without mirror inversion for generating D-ligands that bind with an L-target.
Figure 4B:
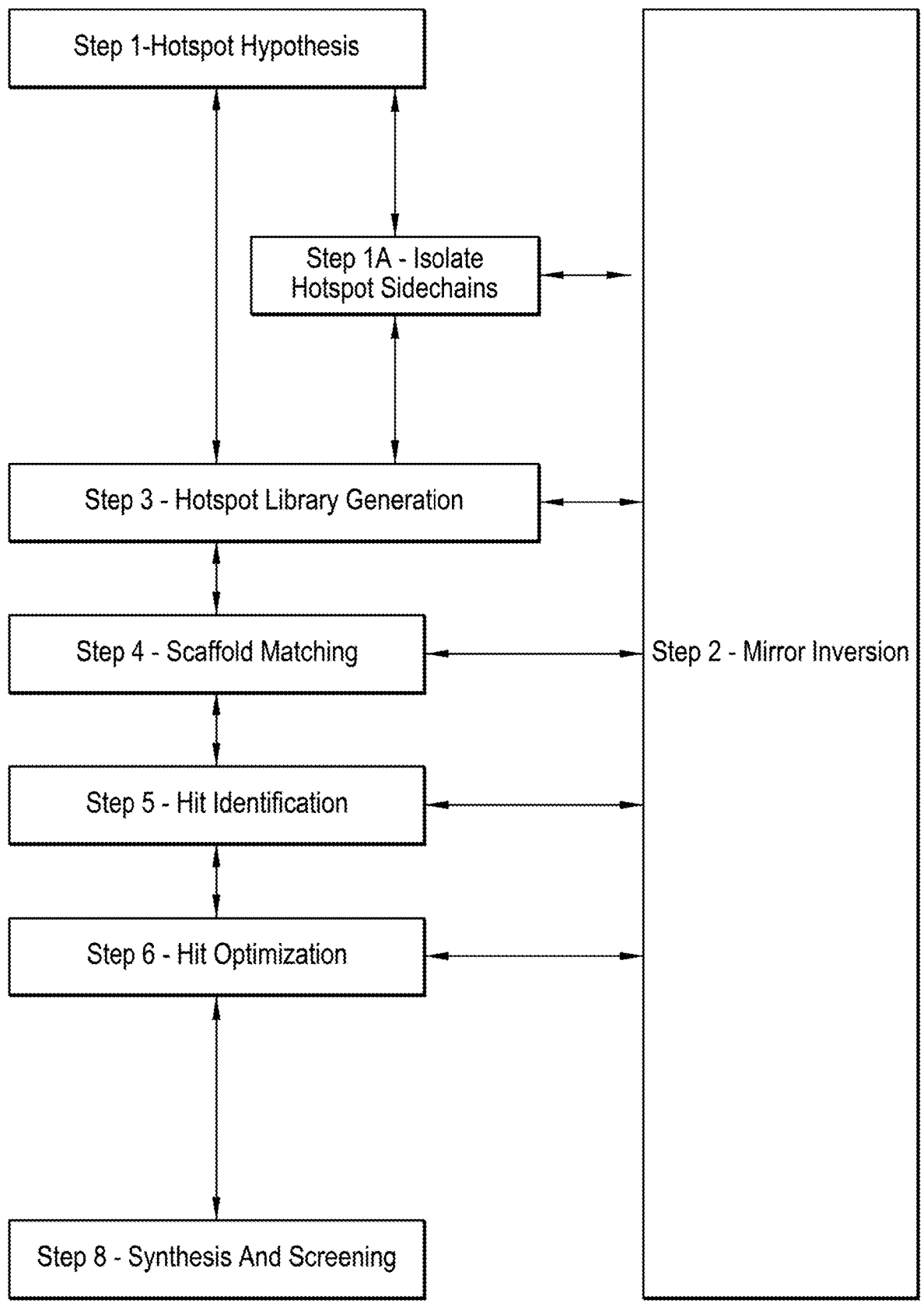
FIG. 4B includes a diagram of method steps of an in silico computing methodology with optional mirror inversion at any step for generating D-ligands that bind with an L-target.
Figure 5:
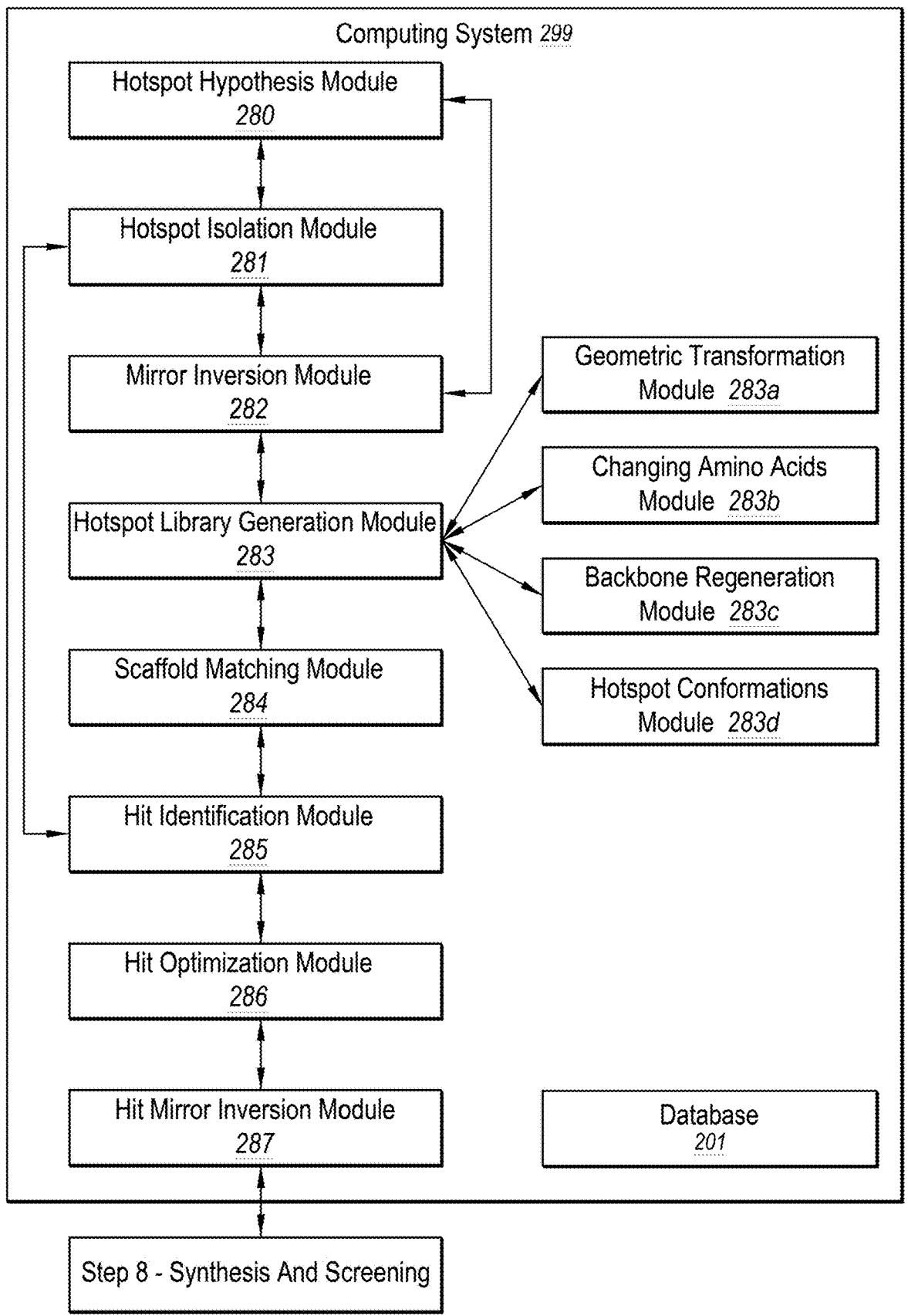
FIG. 5 includes a schematic diagram of a computing system with modules configured for performing the in silico computing methodology of FIG. 4.

As shown in FIGS. 4A and 4B, Step 2 (Mirror Inversion) can be performed at any stage of the design procedure or not be performed at all. Mirror inversion can be introduced in some instances to facilitate the methodology described herein. For instance, if docking of D-hotspots on L-target is computationally difficult, mirror inversion can be advantageously applied followed by the docking of L-hotspots on the D-target. The particular route with mirror inversion in Step 2 and 7, as shown in FIG. 4, has been chosen for convenience because of the employed modeling software (Rosetta package), but may be omitted in some instances. The mirror transformation presented in the design protocol in Step 3, within Step 3C (Backbone Regeneration), where the chirality of the hotspot backbone is inverted, resulting in inverted hotspots can be beneficial. This step can be performed on any side of the mirror and since it only acts on hotspots and not on the target, it allows designing ligands with different chirality from the target and the original ligand.

FIG. 4A illustrates a methodology for determining a D-ligand that binds to an L-target without performing any mirror inversion. As such, Step 3 is performed as described herein except the L-target is used instead of the D-target, and the hotspot side chains are not mirror-inverted. The side chains of the original L-hotspots are then connected with backbone as in D-amino acids. As such, Steps 3A-3D are performed with the L-target and hotspot side chains without any mirror inversion. However, the backbone is always connected with the side chains in a way that results in having D-amino-acids binding L-target. Steps 4, 5, and 6 are performed with the L-target and D-scaffolds or D-hits that are all built of D-amino acids. The mirror inversion has been used in order to obtain structures of these D-scaffolds from the corresponding L-scaffolds. The protocols described herein can be performed in accordance with this modification that does not use mirror inversion of the target. Instead of testing with the L-scaffold and/or L-hit that include the hotspot side chain amino acids with L-chirality, the testing is done with scaffolds and hits with the hotspot side chain amino acids with D-chirality. The result is that after hit optimization in Step 6 that includes a D-hit that binds with the L-target, the D-hit is directly synthesized and screened. The D-hit becomes the D-ligand that includes the hotspot side chain amino acids with D-chirality, where some or all of the other amino acids that are not hotspots having D-chirality and/or L-chirality. In some instances, the D-ligand only has D-amino acids. In step 6, Hit Optimization, some L-amino acids may be introduced in the sequence, as any other non-canonical amino acids.

In one embodiment, at any step or sub-step described herein, a mirror inversion of the target and the hotspots, hotspot backbones, hotspot backbone library, scaffolds or hits can be performed. This can be convenient to take advantage of specific features or circumvent limitations of various molecular modeling packages connected to handling amino acids with opposite chirality. Then, the protocol can be performed with the L-target instead of the D-target, and the hotspots, hotspot backbones, hotspot libraries, scaffolds or hits generally being D-chirality, if chirality is defined.

FIG. 4B illustrates a methodology for determining a D-ligand that binds to an L-target, where mirror inversions can occur before, during or after any step, but where the mirror inversions may be optional. That is, any of Steps 1A, 3, 4, 5, or 6 can be performed with before, during or after mirror inversion, and any of which can be performed with the target and hotspot side chains on either side of the mirror. The first side of the mirror keeps the target an L-target in its original chirality and interacts with backbones, scaffolds, hits, and ligands with the hotspot side chain amino acids having D-chirality. The second side of the mirror inverts chirality of all the centers of the target to a D-target which interacts with backbones, scaffolds, hits, and ligands with the hotspot side chain amino acids having L-chirality. Any of the Steps can be performed on the first side of the mirror or the second side of the mirror, and any process step may switch to the first side or second side of the mirror before or after performing the step. The result is a D-ligand that can bind with the L-target. The D-ligand can be synthesized and screened for physical binding with the L-target.

In one embodiment, the methodology can include a person interacting with the computing system to facilitate performance of certain steps. The person can be considered an operator of the methodology that interacts with the computing system to provide input and/or make selections, among other actions to facilitate the methodology.

In one aspect, the operator can facilitate Step A—Data Acquisition by interacting with the computing system and providing input thereto. In a methodology where multiple templates are available as a starting point for the D-protein design, the operator can decide which template to take for further processing, and enter the decision into the computing system. This can include the operator viewing information received from the computing system, and then entering instructions or selections into the computing system. This decision can be case specific, and can depend on the target's biology.

In one aspect, the operator can facilitate Step 1—Hotspot Hypothesis by interacting with the computing system and providing input thereto. In this step, the operator can review information provided by the computing system and then decide which amino-acids will be used for hotspot conformation library generation. Once the decision is made, the operator can input the decision and instructions into the computing system. The operator can make the decision based on the isolated hotspot affinity prediction, and on visual inspection on case per case basis. As such, the computing system can provide data related to the prediction or the operator can make the prediction based on data and experience in the field. The operator can then receive visual information from the computing system, and then enter the decision into the computing system to facilitate the methodology. For example, some amino-acids can be included solely based on target specific insights from the operator based on data provided to the operator from the computing system.

In one aspect, the operator can facilitate Step 3—Hotspot Library Generation by interacting with the computing system and providing input thereto. During this step, the hotspot libraries can be provided by the computing system to the operator for review. Once the hotspot libraries and data associated therewith is reviewed, the operator can approve the hotspot library upon visual inspection thereof, such as a computer screen graphic or printout provided by the computing system. The operator can then enter approved one or more hotspot libraries into the computing system. It may be that the hotspot conformations vary in a way that may not be beneficial for a particular case study, and thereby the operator can enter input into the computing system to omit or exclude such particular hotspot conformations or libraries having the same. Whether this is the case, can be evaluated by the operator, with knowledge of the target biology and structure. This allows the operator to control the methodology and provide input into the computing system.

In one aspect, the operator can facilitate Step 3B—Changing Amino Acids by interacting with the computing system and providing input thereto. The amino acid chemical space is nearly infinite, and thereby the operator can receive information from the computing system, and then determine one or more amino acids to be in this step. The selection of one or more amino acids can be based on amino-acid availability and/or on the target structure. The selection may be based on visual inspection of data provided by the computing system, such as structures and conformations of amino acid chains. If certain specific non-canonical amino acids are beneficial for hotspot grafting and/or offer additional interactions or alternative anchoring positions for the scaffold, such non-canonical amino acids can be selected. The data, such as graphs or other data, provided to the operator can facilitate the selection of the one or more amino acids. Once the data is reviewed, the operator can then enter instructions into the computing system to be used in the protocol of Step 3B. This allows the operator to instruct the computing system to select certain amino acids for Step 3B.

In one aspect, the operator can facilitate Step 5—Hit Identification and/or Step 6 Hit Optimization. During Step 5, the computing system can provide matched scaffold data from a database, and the operator can select one or more matched scaffolds by inputting instructions into the computing system. The operator may also manually filter hits by entering either hits to include or hits to exclude into the computing system. Additionally, the user can enter hits to save into the computing system. During Step 6, the operator can receive data from the computing system, analyze the data, and then enter appropriate instructions into the computing system to facilitate any of the sub-steps. For example and without limitation, the operator can facilitate any of the following steps by receiving and reviewing information from the computing system and then providing appropriate input into the computing system, such as Step 6A, Step 6C, Step 6D, Step 6E, Step 6F, Step 6G, Step 6H, Step 6I, Step 6J, Step 6K, Step 6L, Step 6M, Step 6O and/or Step 6P. After the Hit Finding and Hit Optimization steps, certain hit classes may be excluded from further processing by the operator. The operator can receive and review data regarding one or more hits families, and identify and/or select hits for exclusion that do not reproduce hotspot interaction correctly or that interact with the target in an improbable way, and then enter the selection into the computing system. The operator may also enter hits for further analysis into the computing system that reproduce hotspot interactions correctly, or interact with the target in a probable way. After these steps, the operator can make a decision regarding the hits to take further into synthesis based on all design parameters, and/or based on visual inspection of the quality of the grafted interactions as provided by the computing system.

In one embodiment, a method of designing a ligand that binds with a target can include: identifying a polypeptide target having L-chirality; determining hotspot amino acids of a polypeptide ligand having L-chirality that have binding interactions with the target; determining transformations of side chains of the hotspot amino acids that retain the binding interactions with the target; and generating a D-polypeptide having one or more hotspot amino acid side chains with D-chirality that retain the binding interactions with the target so that polypeptide binds with the target.

In one embodiment, the method can include determining the hotspot amino acids as amino acids that bind with an epitope of the target.

In one embodiment, the method can include isolating the hotspot amino acids from the rest of the polypeptide ligand so that the hotspot amino acid side chains are each retained with their carbon alpha.

In one embodiment, the method can include determining rotations of the hotspot amino acid side chains that retain the binding interactions with the target, the rotations being around any axis and angle that result in a different orientation of the hotspot sidechain but preserve the nature of the original hotspot interactions (e.g. hydrophobic, hydrogen bond, aromatic).

In one embodiment, the method can include determining chemical modifications of the hotspot amino acid side chains that retain the binding interactions with the target, the chemical modifications resulting in canonical or non-canonical amino acid side chains as the transformed hotspot amino acid side chains.

In one embodiment, the method can include: analyzing interactions between the transformed amino acid side chains and the target; and determining whether the transformed amino acid side chains retain the binding interactions with the target. If the binding interactions with the target are retained, the transformed amino acid side chains are selected. If the binding interactions with the target are not retained, the transformed amino acid side chains are discarded.

In one embodiment, the method can include: analyzing interactions between the transformed amino acid side chains and the target; and determining whether the transformed amino acid side chains sterically clash with the target. If the transformed amino acid side chains do not sterically clash with the target, the transformed amino acids are selected. If the transformed amino acid side chains sterically clash with the target, the transformed amino acids are discarded.

In one embodiment, the method can include: generating a hotspot polypeptide L or D-backbone conformation starting from one or more transformed hotspot amino acid side chains; and determining whether the generated conformation sterically clashes with the target. If the generated conformation does not clash with the target, it is selected. If the generated conformation clashes with the target, it is discarded.

In one embodiment, the method can include: selecting the hotspot polypeptide backbone; and generating a plurality of alternative hotspot polypeptide backbone conformations (Hotspot Library), each capable of binding with the target. In one embodiment, the method can include: selecting the hotspot amino acid; and generating a plurality of hotspot amino acid conformations each capable of binding with the target. In one aspect, the generation of alternative conformations includes conformational sampling techniques. In one aspect, the conformational sampling techniques include molecular dynamics.

In one embodiment, the method can include: performing visual inspection of the generated hotspot library and removing overlapping amino acids from adjacent hotspots. In one embodiment, the method can include: performing a systematic screening of each amino acid from the hotspot library and discarding it if any steric clash occurs with any other hotspot amino acid.

In one embodiment, the method can include: selecting the hotspot amino acid conformations; and: determining scaffolds having a three dimensional structure that allows for grafting the hotspot amino acids on this structure without affecting their relative three dimensional arrangement.

In one embodiment, the method can include: selecting the ligand scaffolds;
  mutating non hotspot amino acids in the ligand scaffold; determining whether the mutated ligand scaffolds have an improved binding score over the ligand scaffolds; and selecting mutated ligand scaffolds having the improved binding score as hits.

In one embodiment, the method can include: selecting the hits; changing sequences of the selected hits to yield optimized hits; and determining whether the optimized hits bind with the target. In one aspect, the sequences of the selected hits are modified after applying conformational sampling techniques to the hits. In one aspect, the conformational sampling techniques include molecular dynamics.

In one embodiment, the method can include: selecting the hits; and changing the sequence of the hits to determine one or more optimal hits having increased binding scores with the target per number of mutations compared to the wild type ligand scaffold. In one aspect, the changing of the sequence of the hits includes one or more of: changing one or more amino acids in the hits that are different from the ligand scaffold back to the amino acids of the original ligand scaffold; mutating single amino acid within 10 Angstrom from the target in the modeled target-ligand complex; mutating two amino acids within 10 Angstrom from the target in the modeled target-ligand complex; mutating three amino acids; mutating less water-soluble amino acids to polar or charged amino-acids; introducing covalent bonds with a purpose of cyclisation; mutating non-canonical amino acids to canonical amino acids; mutating canonical amino acids to non-canonical amino acids; or implementing conformational sampling techniques with the purpose of increasing the binding score. In one aspect, the method can include performing one or more iterative loops with one or more of the changes to the sequence; determining whether the one or more changes to the sequences results in an increased binding score with the target per number of mutations from the ligand scaffold; and selecting hits with increased binding score with the target per number of mutations from the ligand scaffold as optimized hits.

In one embodiment, after being selected, one or more of the optimized hits can be synthesized. The synthesized optimized hits can be capable of binding with the target. In one aspect, the optimized hits are D-ligands. In one aspect, the optimized hits are L-ligands, and the method can include mirror inverting the L-ligands to D-ligands before synthesizing the D-ligands.

In one embodiment, the method can include: mirror inverting the polypeptide target to a D-target having D-chirality; and mirror inverting the side chains of the hotspot amino acids before transformations. The subsequent steps can be performed with the D-target and mirror-inverted hotspot side chains. After backbone regeneration the hotspot amino acids that are generated from the inverted hotspot side chains can be L-amino acids that bind with the D-target. Any of the method steps can be performed with the D-target together with L-hotspot amino acids. In one aspect, the method can include: isolating entire hotspot amino acids from their native polypeptide ligand before the mirror inversion. Any of the method steps described herein can be performed under the D-target and inverted hotspot side chain paradigm, where the inverted hotspot side chains are grafted into the L-ligand. At the end of the protocol the optimized L-ligands can be mirror inverted to D-ligands and the D-ligands can be synthesized.

In one embodiment, the method using the D-target and inverted hotspot side chains can include: determining symmetry operations of the mirror inverted hotspot amino acid side chains that retain the binding interactions with the target, the symmetry operations being around any axis and/or plane and with any angle that result in a different orientation of the hotspot side chain but preserve the nature of the original hotspot interactions (e.g. hydrophobic, hydrogen bond, aromatic, pi-cation); and/or determining chemical modifications of the mirror inverted hotspot amino acid side chains that retain the binding interactions with the target, the chemical modifications resulting in canonical or non-canonical amino acid side chains as the components of the hotspot library.

In one embodiment, the method using the D-target and inverted hotspot side chains can include: analyzing interactions between the transformed amino acid side chains and the D-target; and determining whether the transformed amino acid side chains retain the binding interactions with the D-target. If the binding interactions with the D-target are retained, the transformed amino acid side chains are selected. If the binding interactions with the D-target are not retained, the transformed amino acid side chains are discarded.

In one embodiment, the method using the D-target and inverted hotspot side chains can include: analyzing interactions between the transformed amino acid side chains and the D-target; and determining whether the transformed amino acid side chains sterically clash with the D-target. If the transformed amino acid side chains do not sterically clash with the D-target, the transformed amino acids are selected. If the transformed amino acid side chains sterically clash with the D-target, the transformed amino acids are discarded.

In one embodiment, the method using the D-target and inverted hotspot side chains can include: generating L-backbone atoms starting from one or more transformed hotspot amino acid side chain conformations; and determining whether the generated conformation sterically clashes with the D-target. If the generated conformation does not clash with the D-target, the conformation is selected. If the generated conformation clashes with the D-target, it is discarded.

In one embodiment, the method using the D-target and inverted hotspot side chains can include: selecting a plurality of alternative hotspot amino acid conformations capable of binding with the D-target each having L-chirality. In one aspect, the generation of alternative conformations includes conformational sampling techniques. In one aspect, the conformational sampling techniques include molecular dynamics.

In one embodiment, the method using the D-target and inverted hotspot library can include: selecting the hotspot amino acids; and determining scaffolds having a three dimensional structure that allows for grafting the hotspot amino acids on this structure without affecting their relative three dimensional arrangement.

In one embodiment, the method using the D-target and inverted hotspot library can include: selecting the ligand scaffolds; mutating non-hotspot amino acids in the ligand scaffold; determining whether the mutated ligand scaffolds have an improved score over the ligand scaffolds; and selecting mutated ligand scaffolds having the improved binding score as hits.

In one embodiment, the method using the D-target and inverted hotspot library can include: selecting the hits; changing sequences of the selected hits to yield optimized hits; and determining whether the optimized hits present an improved score. In one aspect, the sequences of the selected hits are modified after applying conformational sampling techniques to the hits. In one aspect, the conformational sampling techniques include molecular dynamics.

In one embodiment, the method using the D-target and inverted hotspot library can include: selecting the hits; and changing the sequence of the hits to determine one or more optimal hits having increased scores with the target per number of mutations from the ligand scaffold. In one aspect, the optimized hits are L-ligands, and the method can include mirror inverting the L-ligands to D-ligands. Once determined the D-ligands they can be chemically synthesized.

In one embodiment, the designing of the ligands is performed in silico. Once designed, the D-ligands can be synthesized.

In one embodiment, any of the methods that use L-targets and/or D-targets to create the ligands can involve mirror inversions. As such, the methods described herein can include one or more of the following: performing one or more mirror inversions of the target from L-chirality to D-chirality; performing one or more mirror inversions from L-chirality to D-chirality of one or more of the following: ligand, hotspots, hotspot backbone, scaffolds, hits, diversified hits, optimized hits; or performing one or more mirror inversions from D-chirality to L-chirality of one or more of the following: ligand, hotspots, hotspot backbone, scaffolds, hits, diversified hits, optimized hits; or performing mirror inversion of any amino acid sidechain.

One skilled in the art will appreciate that, for these and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular in silico methods, reagents, compounds compositions or biological systems, which can, of course, vary. It is also to be understood that the terminology used herein is for the purpose of describing particular embodiments only, and is not intended to be limiting.

In one embodiment, the present methods can include aspects performed on a computing system, which can be considered to be in silico methodologies. As such, the computing system can include a memory device that has the computer-executable instructions for performing the method. The computer-executable instructions can be part of a computer program product that includes one or more algorithms for performing any of the methods of any of the claims. The memory device can include the instructions for performing any of the steps, alone or combinations thereof, as provided herein.

In one embodiment, any of the operations, processes, methods, or steps described herein can be implemented as computer-readable instructions stored on a computer-readable medium. The computer-readable instructions can be executed by a processor of a wide range of computing systems from desktop computing systems, portable computing systems, tablet computing systems, hand-held computing systems as well as network elements, and/or any other computing device. The computer readable medium is not transitory. The computer readable medium is a physical medium having the computer-readable instructions stored therein so as to be physically readable from the physical medium by the computer.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of modules that can include hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of physical signal bearing medium used to actually carry out the distribution. Examples of a physical signal bearing medium include, but are not limited to, the following: a recordable type medium such as a floppy disk, a hard disk drive, a CD, a DVD, a digital tape, a computer memory, any other physical medium that is not transitory or a transmission. Examples of physical media having computer-readable instructions omit transitory or transmission type media such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Figure 9:
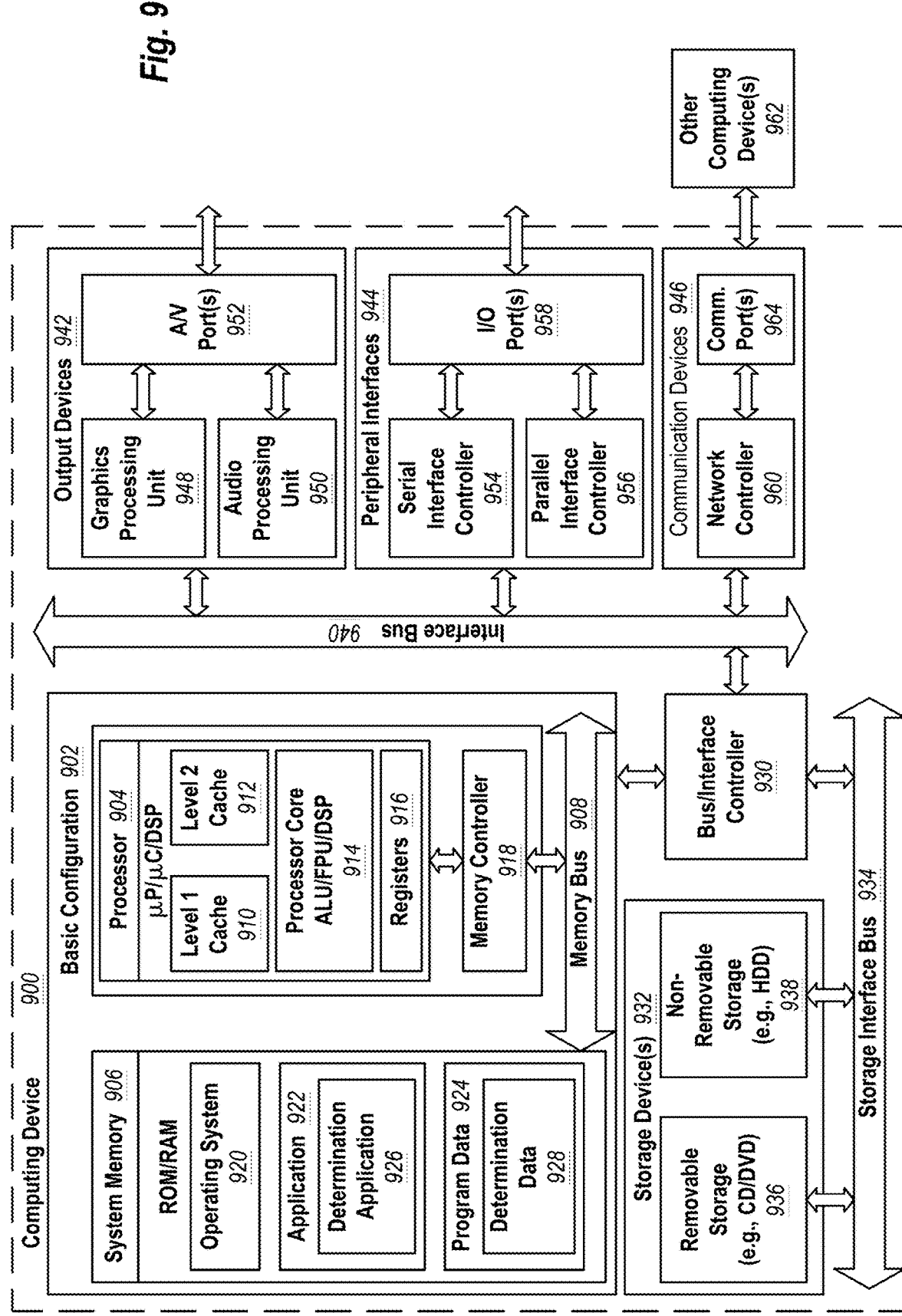
FIG. 9 includes a schematic diagram of a computing system that can include the modules that are configured for performing the in silico computing methodologies.

FIG. 9 shows an example computing device 900 that is arranged to perform any of the computing methods described herein. The computing system 900 can represent a user side computing device, such as a mobile computer. In a very basic configuration 902, computing device 900 generally includes one or more processors 904 and a system memory 906. A memory bus 908 may be used for communicating between processor 904 and system memory 906.

Depending on the desired configuration, processor 904 may be of any type including but not limited to a microprocessor (µP), a microcontroller (µC), a digital signal processor (DSP), or any combination thereof. Processor 904 may include one more levels of caching, such as a level one cache 910 and a level two cache 912, a processor core 914, and registers 916. An example processor core 914 may include an arithmetic logic unit (ALU), a floating point unit (FPU), a digital signal processing core (DSP Core), or any combination thereof. An example memory controller 918 may also be used with processor 904, or in some implementations memory controller 918 may be an internal part of processor 904.

Depending on the desired configuration, system memory 906 may be of any type including but not limited to volatile memory (such as RAM), non-volatile memory (such as ROM, flash memory, etc.) or any combination thereof. System memory 906 may include an operating system 920, one or more applications 922, and program data 924. Application 922 may include a determination application 926 that is arranged to perform the functions as described herein including those described with respect to methods described herein. Program Data 924 may include determination information 928 that may be useful for analyzing the contamination characteristics provided by the sensor unit 940. In some embodiments, application 922 may be arranged to operate with program data 924 on an operating system 920 such that the work performed by untrusted computing nodes can be verified as described herein. This described basic configuration 902 is illustrated in FIG. 9 by those components within the inner dashed line.

Computing device 900 may have additional features or functionality, and additional interfaces to facilitate communications between basic configuration 902 and any required devices and interfaces. For example, a bus/interface controller 930 may be used to facilitate communications between basic configuration 902 and one or more data storage devices 932 via a storage interface bus 934. Data storage devices 932 may be removable storage devices 936, non-removable storage devices 938, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 906, removable storage devices 936 and non-removable storage devices 938 are examples of computer storage media. Computer storage media includes, but is not limited to, RAM, ROM, EEPROM, flash memory, solid state drives (SSDs) or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 900. Any such computer storage media may be part of computing device 900.

Computing device 900 may also include an interface bus 940 for facilitating communication from various interface devices (e.g., output devices 942, peripheral interfaces 944, and communication devices 946) to basic configuration 902 via bus/interface controller 930. Example output devices 942 include a graphics processing unit 948 and an audio processing unit 950, which may be configured to communicate to various external devices such as a display or speakers via one or more A/V ports 952. Example peripheral interfaces 944 include a serial interface controller 954 or a parallel interface controller 956, which may be configured to communicate with external devices such as input devices (e.g., keyboard, mouse, pen, voice input device, touch input device, etc.) or other peripheral devices (e.g., printer, scanner, etc.) via one or more I/O ports 958. An example communication device 946 includes a network controller 960, which may be arranged to facilitate communications with one or more other computing devices 962 over a network communication link via one or more communication ports 964.

The network communication link may be one example of a communication media.

Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 900 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 900 may also be implemented as a personal computer including both laptop computer and non-laptop computer configurations.

The embodiments described herein may include the use of a special purpose or general-purpose computer including various computer hardware or software modules in accordance with the modules described herein that can perform the steps of the in silico methodologies.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" can refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system. All design steps can be performed by the operator using the computing system, and once designed the D-ligand can be synthesized and tested on the L-target.

EXPERIMENTAL

In all examples, it is possible for the operator of the computational design methods to implement some or all data acquisition and data input protocols with the computing system, and implement any computational design selections or choices with the computing system. When the computing system obtains or generates computational design data, the operator can receive such data from the computing system, analyze the data with or without the computing system, and then enter input into the computing system based on the computational design data and analysis thereof.

Example 1: Computational Design of a D-Protein Binding to Interleukin-17A

Interleukin 17A is a member of IL-17 family of cytokines, forming a dimer that presents a cysteine-knot fold with two intramolecular disulfide bridges. IL17 response is involved in diseases such as asthma, rheumatoid arthritis and psoriasis. In this example a proprietary structure of a complex between the FAB of a proprietary anti-IL17 antibody CNT06785 and IL17A is used in order to design a D-protein ligand that can bind to the IL17A dimer. A class of D-protein ligands is shown to exhibit competition with a proprietary centyrin WPW, binding to an epitope overlapping with the epitope of CNT06785 and does not compete with the antibody CAT2200 binding in a different region of IL17A. Thus, a D-protein ligand can be designed as described herein, and then synthesized and tested for in vitro binding with the IL17A dimer.

Regarding the modelling part, for all of the following examples, the force-field (i.e., the estimator of steric/chemical correctness and binding, which is a function of molecular coordinates of a complex) of choice was the mm_std version of Rosetta force-field although those skilled in the art will recognize that other force fields can be used for the same purpose. Therefore, all the estimates of the free energy of binding, being DG or DDG, will be expressed in Rosetta Units (RU).

The starting point for designing the D-protein binder to IL-17 was a crystal structure of a complex of IL17 and a proprietary anti-IL17A antibody. The structure was first reduced by removing the constant region of the FAB since they do not directly interact with the IL17 dimer. Then, the missing hydrogen atoms were added and the sidechains were rebuilt so to reproduce the force-field closest local minimum (this operation is also referred to as Prepacking). The resulting structure closely corresponded to the initial X-Ray crystal structure. These operations are represented by Step A—Data Acquisition.

Subsequently, the model was optimized by choosing the lowest score among four parallel optimization runs. Each optimization process included a succession of prepacking, backbone optimization, local minimization, local redocking of the FAB followed by further local minimization and prepacking. The backbone was allowed to have only a minimal change since the full optimization of a reduced complex could affect the final conformation. In each round, the best structure from the four parallel optimization runs was selected and input into the next round. Once the convergence of the Rosetta score was reached, the complex was considered ready for further processing.

Step 1: Hotspot Hypothesis

Each residue belonging to the FAB paratope was locally optimized after being isolated from the context of the FAB. This was done to see whether the amino-acid interactions were retained in absence of the FAB (FIG. 4, Step 1). Two Phenylalanine residues—F92 and F91, buried deeply in a pocket on IL17, and one Tyrosine residue Y89, were identified as having DG (the calculated binding free-energy) below 2.5 RU's and preserved the original interactions when taken away from the context of the FAB. The same residues were initially identified as forming most atomic contacts with the target, and were tagged as hotspots by visual inspection. Based on all indications, the three amino-acids were selected as the starting point for designing the D-protein ligand, and from now on called hotspots.

Step 2: Mirror Inversion

Figure 7:
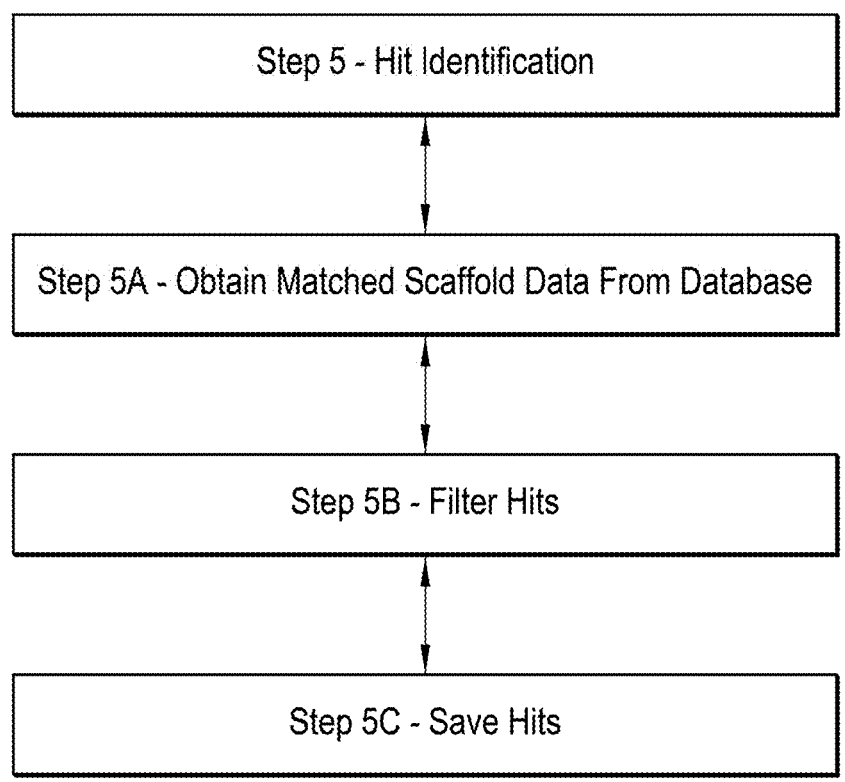
FIG. 7 includes a diagram of method steps of an in silico computing methodology for hit identification.
Figure 20A:
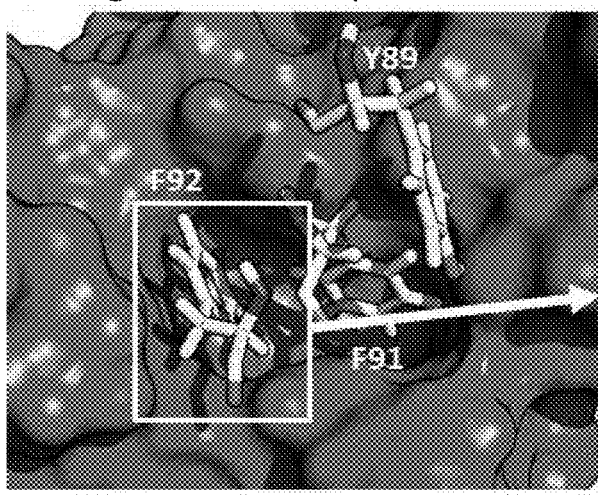
FIG. 20A includes images that show the D-complex, composed of D-target and D-hotspots being converted to a complex of D-target and L-hotspots.
Figure 20A:
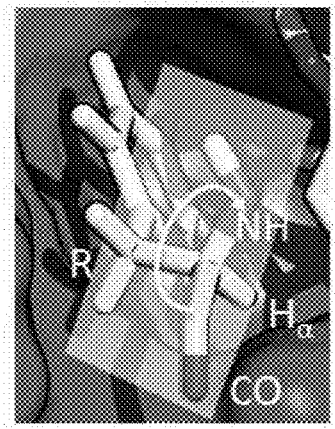
Figure 20A:
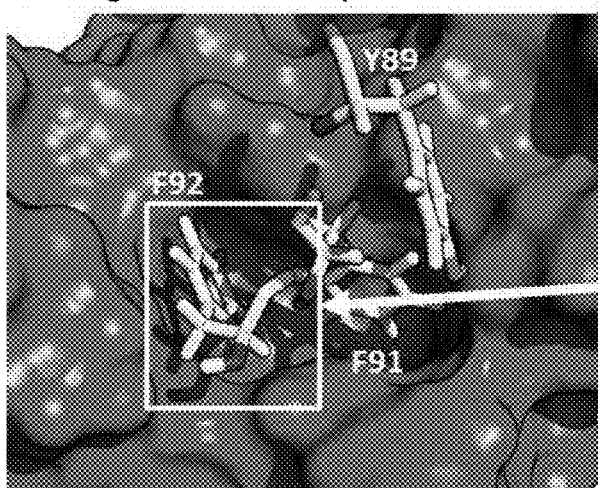
Figure 20A:
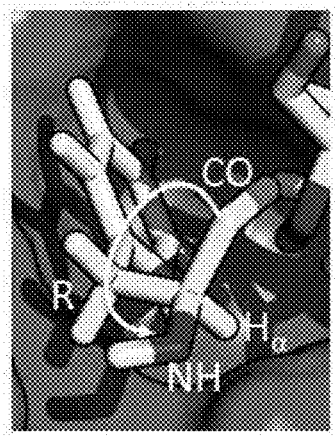
Figure 20B:
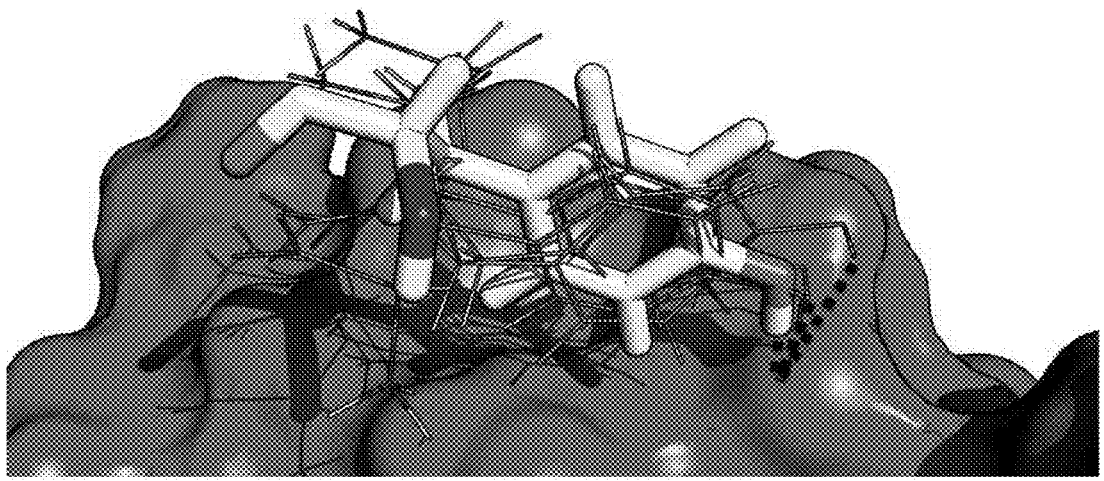
FIG. 20B includes an image that shows inverted hotspot library generation for Y89, preserving hotspot-target hydrogen-bond.
Figure 20C:
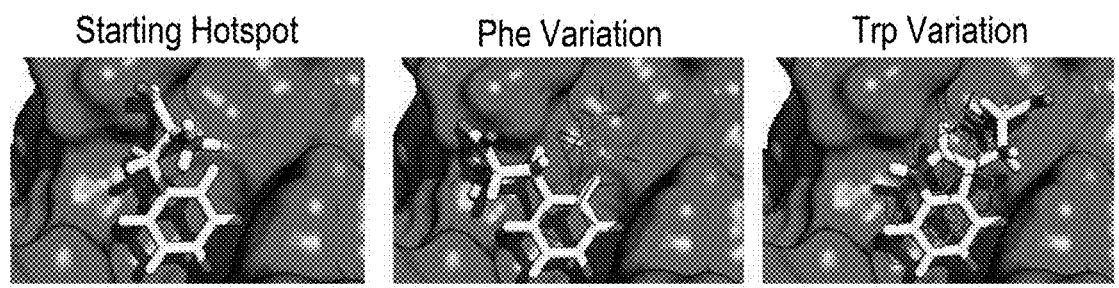
FIG. 20C includes images that show alternative hotspots that are found by exploiting chemical similarity and internal structural symmetry for hotspot F92.
Figure 20D:
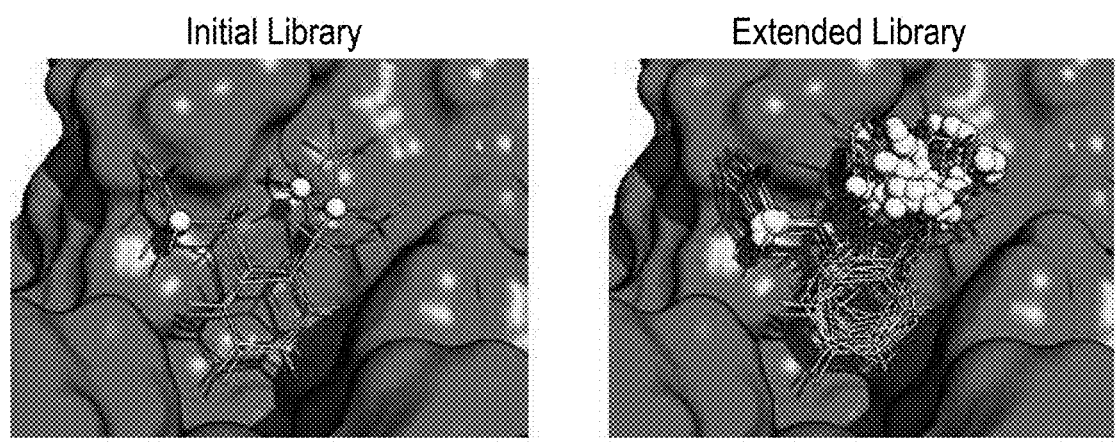
FIG. 20D includes images that show the generation of alternative backbone conformations for the inverted hotspot library, in the case of F92 hotspot. Alternative sidechain orientations in the left panel are used to perform redocking and backbone sampling (shown in the right panel). The procedure increases the number of alternative C-alpha positions indicated with white spheres.
Figure 20E:
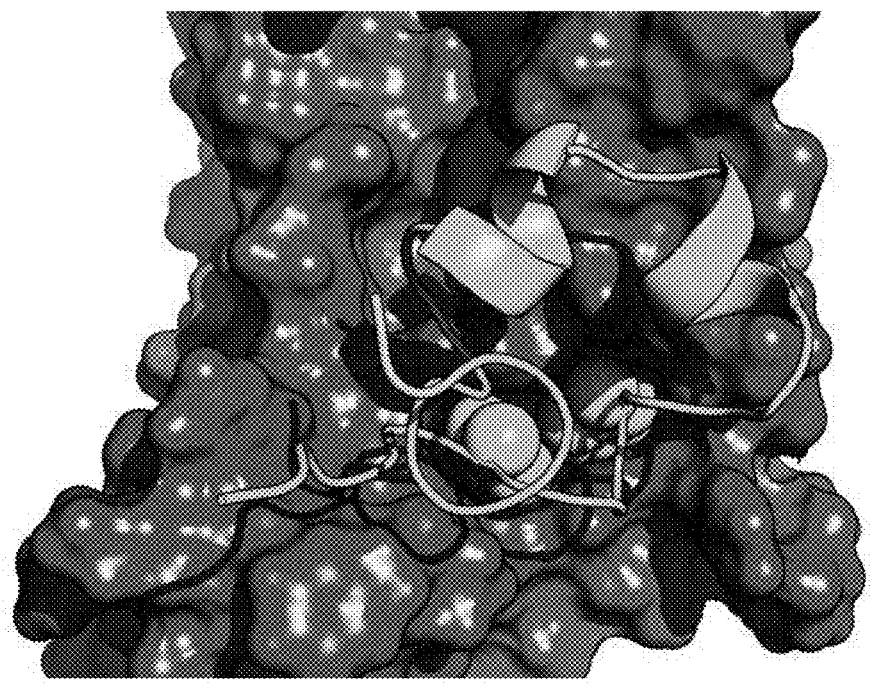
FIG. 20E shows an L-scaffold hit (PDBID 1ROO) grafted with two inverted hotspot residues F91 and F92.

The IL17-hotspots L-complex was mirror inverted to a D-complex, by changing the sign of the x-coordinates in the protein database (PDB) file of the L-complex and changing the residue names so to reflect the change in chirality (FIG. 4, Step 2).

Step 3: Sidechain Library Generation

Each hotspot residue had its backbone chirality inverted (FIG. 4, Step 3) with the chirality opposite to the chirality of the target (here the backbone of each hotspot was reconstructed in L-chirality), resulting in so called "inverted hotspots". The procedure of backbone regeneration (FIG. 4, Step 3C) includes taking the original amino-acid backbone and inverting only the backbone atoms through a mirror crossing through the $H_\alpha$, $C_\alpha$ and $C_\beta$, while keeping the sidechain fixed—see FIG. 20A. The backbone inversion was performed with a Python script using Pymol API.

FIG. 20A shows the D-complex, composed of D-target and D-hotspots being converted to a complex of D-target and L-hotspots. The chirality can be deduced by the CO—R—N(H) rule: if the order of the CO—R—NH group, after positioning the amino-acid so that $H_\alpha$ in the background and $C_\alpha$ in the center, is counter-clockwise then the chirality is L, if it is clockwise then is D. The arrow indicates the order according to the CO—R—N(H) rule. In the left panel an idealized mirror is shown to better understand the process of backbone regeneration (FIG. 4, Step 3C).

For each of the inverted hotspots, a set of poses compatible with the target were added to the hotspot library. In case of a hydrogen bonded residue, the presence of the specific hydrogen bond was also considered a condition to accept the new pose, see FIG. 20B. In case of all inverted hotspots, another condition was to keep the crystal structure interactions, including hydrophobic contacts. FIG. 20B shows the inverted hotspot library generation for Y89. The starting pose of the sidechain is retained and the hydrogen bond is preserved in all poses added to the library.

Since two of the residues in the hotspot hypothesis are phenylalanines, several alternative C-alpha positions are possible while preserving the interactions formed by the side-chains. The backbone was rebuilt starting from different positions on the ring and the resulting poses were locally redocked. A pose was added to the library when the in silico computed affinity was at least 2 RUs and interactions of the sidechains were reproduced, thus providing alternative positions of the backbone (see FIG. 4, Step 3D). Similarly, by exploiting the chemical similarity among amino-acids, the phenylalanine residues were also mutated to tryptophan while keeping the six-membered ring moiety in the binding position. If, after optimization (i.e. after repeating Step 3D), the alternative pose was still providing a reasonable in silico affinity and mimicking the phenylalanine ring position, then the alternative hotspot residue was added to the inverted hotspot library, see FIG. 20C, as well as FIG. 4 Step 3A and 3B: Geometric Transformation and Changing Amino Acids. FIG. 20C shows alternative hotspots that are found by exploiting chemical similarity and internal structural symmetry for F92. The left panel shows the initial hotspot. The central panel shows the backbone position is changed by exploiting sidechain symmetry. The right panel shows the phenylalanine is mutated into a tryptophan residue where the phenyl ring is overlaying with the starting hotspot.

In the next step of the inverted hotspot library generation, each residue of the library underwent a further conformational sampling where the backbone was rotated while keeping the sidechain fixed (performed using Rosetta's Inverse Rotamers routine). This was followed by a further redocking to accommodate eventual clashes with the target, see FIG. 20D and FIG. 4, Step 3D. This step multiplied the number of backbone conformations to increase the possibility of finding a matching scaffold in the next steps of the design methodology. All conformations that fulfilled the in silico affinity threshold of 2RUs, were added to the inverted hotspot library. FIG. 20D shows the generation of alternative backbone conformations for the inverted hotspot library, in the case of F92 hotspot. Alternative sidechain interaction preserving orientations are presented in the left panel. These conformations are then used to perform redocking and backbone sampling in order to increase the number of alternative C-alpha positions (indicated with white spheres). The resulting conformational library is presented in the right panel.

Additionally, alternative conformations in the library belonging to different hotspots were often overlapping since they were generated independently. Therefore, the overlapping hotspots were removed in order to maximize the probability of complementary hotspot pairs during the hotspot-scaffold matching procedure. The final hotspot conformation library included 27 different poses for the residue Y89, 60 poses for the residue F92 and 71 poses for F91.

Step 4—Scaffold Matching

A set of scaffolds was chosen from the PDB database by selecting peptides reachable through standard chemical synthesis. Peptides no longer than 35 amino-acids were selected. Transmembrane peptides were excluded, as well as linear peptides without secondary structure stabilized by the interactions with a receptor. A set of about 300 peptides was retrieved and input into the computing system, many of them toxins, stabilized by multiple cysteine bridges. Most of the structures were determined with NMR, and contained multiple models. All models were then used for matching with the inverted hotspot library and the target. (FIG. 4, Step 4: Scaffold Matching, Steps 4A-C). During computation of the algorithm, the L-scaffolds are matched with the inverted hotspots containing L-backbones.

In order to perform the matching, each L-scaffold was docked 300 times on the epitope of the D-target. For each pose, an attempt of grafting at least two residues from the hotspot library onto the docked L-scaffold was performed. If the docked pose was compatible with the hotspot grafting step, then the rest of the paratope of the scaffold was redesigned in order to improve surface complementarity and form additional interactions with the target. Only the scaffolds that could have the hotspots grafted without significant internal strain, and without significant clashes with the target according to the Rosetta scoring function (FIG. 6, Step 4C) were further considered (FIG. 6, Step 4E).

Step 5—Hit Identification

Only the scaffolds presenting a number of mutations less than 10 in respect to its wild-type, with a Rosetta's DG score of less than −8 RUs (50% of the maximum score among all designs) and with a contact surface area of at least 1000 Å$^2$ were further considered for the next step. See FIG. 20E and FIG. 7, Steps 5A-C. The thresholds selected at the hit identification phase were not very stringent. FIG. 20E shows hotspot matching, where an example is shown for an L-scaffold hit (PDBID 1ROO) that matches with conformations of two inverted hotspot residues F91 and F92.

Step 6—Optimization

Since over-mutating the scaffold could affect folding, an in silico estimate of mutation importance was calculated (FIG. 8, Step 6A). This was done by calculating a difference of two scores (i.e., the difference between two computed binding affinities or DDG), one for the mutant and the other of mutant with a back-to-wild type mutation (FIG. 8, Step 6B). If the mutation was found to provide a DDG of $-0.5$ RU or more, the mutation was labeled negligible. All such negligible mutations were mutated back to wild-type, creating a number of designs with a range of back to wild type mutations (FIG. 8, Step 6D) including a design with significant mutations only (FIG. 8, Step 6C). Steps 6E and 6F were skipped in this example, but may be employed. At this stage, designs with 9 or more mutations were excluded from the library (FIG. 8, Step 6G).

For each entry in the hit library, two more rounds of single mutations on the paratope of the designed ligand were attempted to create variability and improve affinity (FIG. 8, Step 6H-6N loop). For each new structure all these criteria needed to hold simultaneously, for the mutant to be added to the hit library: 1000 Å$^2$ or higher change in surface area upon complexation, a DG score less than $-8$ RU, number of mutations <9 and change in DDG after mutation <$-0.5$ RU (non-negligible mutation), see FIG. 8, Step 6J-K.

A successive calculation in which the complex was locally perturbed and redocked was carried out (FIG. 8, Step 6I). The new structures were only accepted when the previous set of criteria was simultaneously fulfilled. A final round of mutation was carried out on the redocked set of hits. Again, the same criteria needed to be simultaneously valid for the mutated ligands to be included in the hits library (FIG. 8, Step 6J-K).

At the end of the procedure the redundant designs (ligands having the same sequences) were removed. A final visual inspection of all the structures can be used to reduce the final set and avoid artifacts [FIG. 4, Step 6—Hit Optimization]. Hits that lost the original hotspot orientation as a result of redocking and mutating were all excluded (FIG. 8, Step 6P).

For all these steps reported above including mutating residues, optimization and in silico binding affinity estimate, Rosetta modelling package was used, but many of the procedures can be carried out with a variety of modelling packages available on the market or can be developed. The thresholds used can be calibrated for different scoring functions. A set of controls was added to the list of hits. The negative controls were created by taking the most promising in silico ligand and mutating each of the hotspots to a corresponding wild-type amino acid whenever the WT amino acid was chemically significantly different from the hotspot. Otherwise the hotspot was mutated to a significantly chemically different residue in order disrupt the hotspot interactions with the target. These negative controls are called "hotspot knock-outs". The wild type sequence was also included as negative control.

Step 7—Mirror Inversion

The final set of sequences was "mirror inverted" through a simple text operation of converting uppercase amino acid abbreviations in the sequences to lowercase abbreviations in the sequences [FIG. 4, Step 7: Hit Mirror Inversion]. Such upper case to lower case operation results in converting all L-amino acids to D-amino-acids, and therefore turning them to D-protein (e.g., for non-chiral glycine g=G). The final peptide library for scaffold 1ROO is presented in Table 1. Noncanonical amino acids have been demarked with the following symbols: "<" 3-naphtyl-D-alanine, "x" D-norleucine. The knock-outs have been designed by mutating the hotspot amino acid phenylalanine to glutamic acid.

TABLE 1

| MOLECULE ID | CONTROLS | Sequence |
| --- | --- | --- |
| DP141050 | WT | H-rscidtipksrctafqckhsmkyrlsfcrktcGtc-OH |
| DP141071 | | H-rsciatfpksfctaflckhlmkarlsycrktcGtc-OH |
| DP141090 | | H-rsciatfpkyfctaflckhlmkarlsycrktcGtc-OH |
| DP141087 | | H-rsciatfpkyfctaflckhlmkarlsfcrktcGtc-OH |
| DP141072 | | H-rscqatfpksfctaflckhlmkarlsycrktcGtc-OH |
| DP141092 | | H-rsciaafpkyfctaflckhlmkarlsycrktcGtc-OH |
| DP141080 | | H-rsciaafpksfctaflckhlmkarlsycrltcGtc-OH |
| DP141073 | | H-rsciaafpksfctaflckhlmkarlsycrktcGtc-OH |
| DP141094 | | H-rsciatfpkyfctaflckhlmkarlsycrltcGtc-OH |
| DP141088 | | H-rscqatfpkyfctaflckhlmkarlsfcrktcGtc-OH |
| DP141063 | KNOCK-OUT | H-rsciatepksfctaflckhlmkarlsycrktcGtc-OH |
| DP141065 | KNOCK-OUT | H-rscqatepkyfctaflckhlmkarlsycrktcGtc-OH |
| DP142130 | | H-rscqatfpklfctaflckhlmkarlsycrktcGtc-OH |
| DP142131 | | H-rscqatfpksfctaflckhlmkarls<crktcGtc-OH |
| DP142133 | | H-rscqatfpksfctaflckhlmkarlsncrktcGtc-OH |

TABLE 1-continued

| MOLECULE ID | CONTROLS | Sequence |
| --- | --- | --- |
| DP142134 | | H-rscqatfpksfctaflckhlmksrlsycrktcGtc-OH |
| DP142135 | | H-rscqatfpksfctaflckhlmkxrlsycrktcGtc-OH |
| DP142136 | | H-rscqatfpklfctaflckhlmkxrlsycrktcGtc-OH |
| DP142137 | | H-rscqatfpklfctaflckhlmkxrls<crktcGtc-OH |

Step 8—Synthesis and Screening

All D-proteins were synthesized employing routine Fmoc-based solid phase peptide chemistry. A purity criterion of 90+% was enforced for the resulting linear D-proteins and this was assessed for all individual cases by a combination of HPLC (purity) and mass spectrometry (identity). All D-proteins were delivered as solid, lyophilized materials in individual 1.0 mg aliquots. The proteins were folded to their respective functional form.

Figure 21:
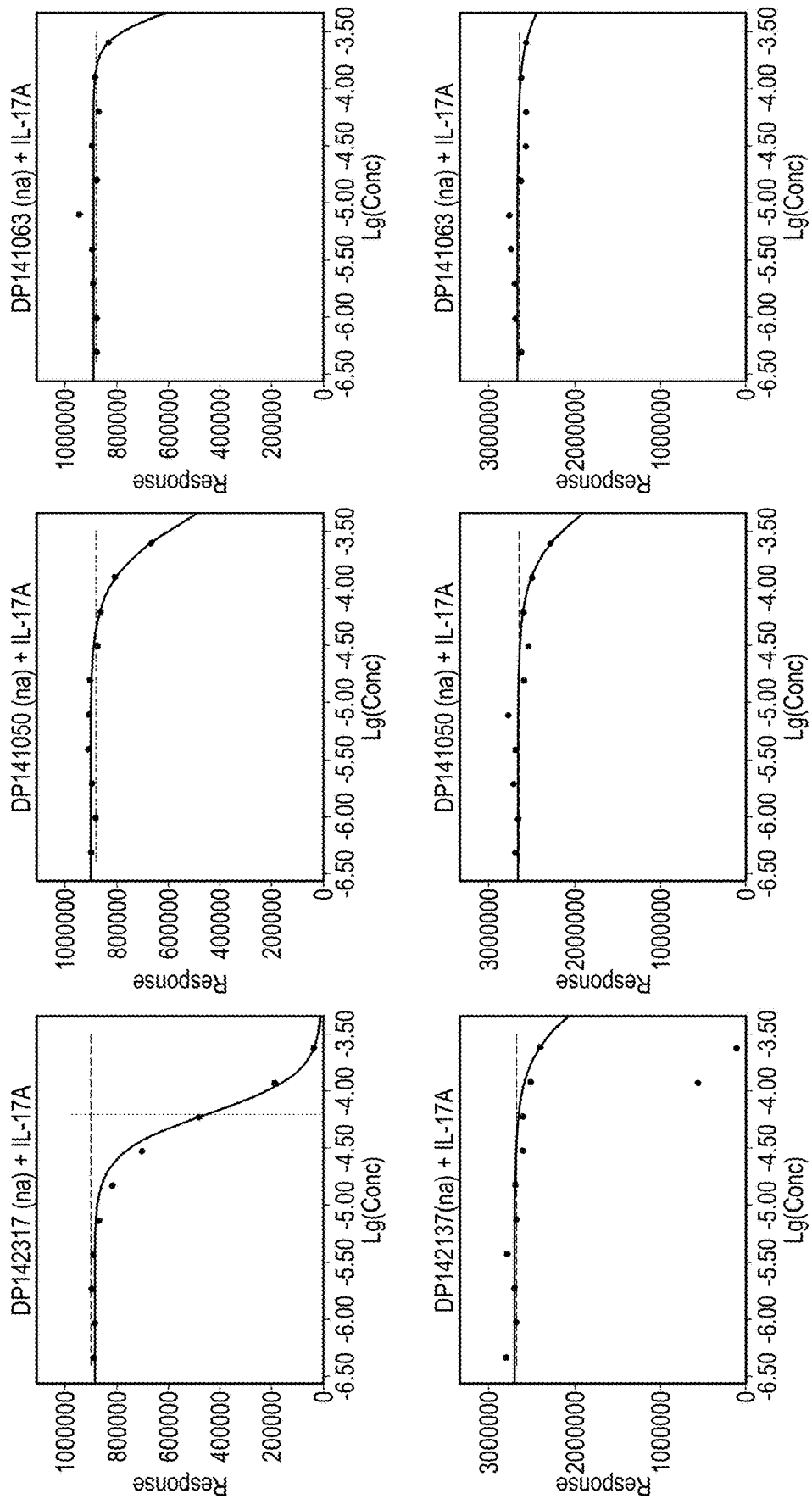
FIG. 21 includes graphs that show the competition ELISA results for the optimized IL17 hit DP142137 (left graphs), wild-type DP141050 (center graphs) and hotspot knock-out DP141063 (right graphs), where upper graphs show competition with centyrin WPW, and lower graphs are with antibody CAT2200, binding to a non-overlapping epitope.

In order to assess the potential binding of the D-Proteins to IL17A at the binding site of CNT06785, the D-Proteins were screened in an ELISA competition assay against a known competitor of antibody CNT06785, Centyrin WPW-His. To show the specific binding to the epitope, negative control antibody CAT2200 was taken along that binds to a different, non-overlapping epitope on IL17A. Results of the competition ELISA performed on IL17A are presented in FIG. 21. FIG. 21 shows the competition ELISA results for the optimized hit DP142137 (left graphs), wild-type DP141050 (center graphs) and hotspot knock-out DP141063 (right graphs). Upper graphs show competition with centyrin WPW, lower graphs—with antibody CAT2200 binding to a non-overlapping epitope. Response is plotted as a function of logarithm of concentration.

From the library of 19 proteins (including negative controls—WT and two knock-outs), one hit was identified having a pIC50 of 4.2 (64 µM) and showing lack of activity for all negative controls. The negative controls included: Competition of the lead DP142137 with CAT2200—antibody binding a non-overlapping epitope; Competition of the wild-type scaffold DP141050 with centyrin WPW; Competition of the wild-type scaffold DP141050 with CAT2200; Competition of two knock-outs DP141063 and DP141065 with centyrin WPW; and Competition of two knock-outs DP141063 and DP141065 with CAT2200. None of the negative controls showed activity, as compared to a clear binding curve for DP142137 and centyrin WPW competition. This example shows that the methodology described herein can be used to design ligands for a target, and that the designed ligands can be constructed and tested to show the physical ligands bind the physical target.

Example 2: Computational Design of a D-Protein Binding to Influenza Hemagglutinin In this example, the structure of a complex between the FAB of the broadly neutralizing antibody FI6 and the H1 influenza hemagglutinin (HA) is used in order to design a D-protein ligand that can bind to the L-target influenza H1 hemagglutinin. A class of D-protein ligands is shown to exhibit competition with the designer protein HB80.4 ligand for binding to an epitope overlapping with the epitope of FI6, and to not compete with an HA-head binding antibody. Additionally, the designer D-protein ligand is confirmed to bind the FI6 epitope of the L-target via means of X-Ray crystallography.

Step A: Data Acquisition.

The starting point for designing the D-protein binder to HA was a crystal structure of a complex between H1 HA and the broadly neutralizing antibody FI6 (PDB ID 3ZTN). The missing hydrogen atoms were added and the sidechains were rebuilt and repacked with Rosetta. Subsequently, the model was optimized by choosing the lowest score among twenty independent optimization runs. Each optimization process included a succession of prepacking, backbone optimization, local minimization, local redocking of the FAB followed by further local minimization and prepacking. The backbone was allowed to change only minimally since the full optimization of a reduced complex could affect the final conformation. Five rounds of optimization were performed, with the complex with the best score being selected after each round and input into the next optimization round. At all steps, the sidechain of the central epitope residue W21 (HA2 subunit) was constrained, following an observation that this particular residue significantly changed a rotamer state during repacking and the alternative rotamer state was not consistent with H1 HA crystal structure. After five rounds of optimization and convergence of the Rosetta score, the complex was deemed ready to be used for the next step.

Step 1: Hotspot Hypothesis.

Each residue belonging to the paratope was locally optimized after being isolated from the context of the FAB. This was done to see whether the amino-acid interactions were retained in absence of the FAB (FIG. 4, Step 1). Four residues—L100A, Y100C, F100D and W100F, were identified as having DG (e.g., the calculated binding free-energy) below 2.5 RUs and preserved the original interactions when taken away from the context of the FAB. The same residues were initially identified as forming most atomic contacts with the target, and were tagged as hotspots by visual inspection. Based on all indications, the four amino-acids were selected as the starting point for designing the D-protein ligand, and from now on called hotspots.

Step 2: Mirror Inversion.

The HA-hotspots L-complex was mirror inverted to a D-complex, by changing the sign of the x-coordinates in the PDB file of the L-complex and changing the residue names to reflect the change in chirality.

Step 3: Hotspot Library Generation.

Each hotspot residue had its backbone chirality inverted (here the backbone of each hotspot was reconstructed in L-chirality), resulting in so called "inverted hotspots." The procedure of backbone regeneration included taking the original amino-acid backbone and inverting only the backbone atoms through a mirror crossing through the $H_\alpha$, $C_\alpha$ and $C_\beta$, while keeping the sidechain fixed. The backbone inversion was performed with a Python script using Pymol API.

For each of the inverted hotspots, a set of poses compatible with the target was generated and added to the hotspot library. In all inverted hotspots, preservation of the crystal structure interactions, including hydrophobic contacts, was a set condition. In the hydrogen bonded residues Y100C and W100F, the presence of the specific hydrogen bond was also set. In order to obtain alternative poses, each inverted hotspot was redocked with Rosetta. Poses were added to the library when the in silico computed affinity was as least 2 RU's and interactions of the sidechains were reproduced. In the final step of the inverted hotspot library generation, each residue of the library underwent a further conformational sampling where the backbone was rotated while keeping the sidechain fixed (performed using Rosetta's Inverse Rotamers routine). This was followed by a further redocking to accommodate eventual clashes with the target. All conformations that fulfilled the in silico affinity threshold of 2 RUs, were added to the inverted hotspot library. In the end, the hotspot library included 486 poses for L100A, 316 poses for Y100C, 431 poses for F100D and 531 poses for W100F.

Step 4—Scaffold Matching.

Different combinations of inverted hotspots from the hotspot library were used for matching with the scaffolds. The following combinations of inverted hotspots were tested: FWL, LY, LF, LW, and FW. The same scaffold set as in Example 1 was used for matching with the hotspot library. In order to perform the matching, each scaffold was docked 30 times on the epitope of the D-target. For each pose, an attempt of grafting at least two residues from the library onto the docked scaffold was performed. If the docked pose was compatible with the hotspot grafting step, then the rest of the paratope of the scaffold was redesigned in order to improve surface complementarity and form additional interactions with the target. Only the scaffolds that could have the hotspots grafted without significant internal strain, and without significant clashes with the target according to the Rosetta scoring function Step 5—Hit Identification.

Only the scaffolds presenting a number of mutations less than 10 in respect to its wild-type, with a Rosetta's DDG score of less than −8 RUs (50% of the maximum score among all designs) and with a contact surface area of at least 1000 Å² were further considered for the next step. See FIG. 7, Steps 5A-C. The thresholds selected at the hit identification phase were not very stringent.

Step 6—Optimization.

Since every mutation in the wild-type scaffold could affect folding, an in silico estimate of how important each mutation is, was calculated (FIG. 8, Step 6A) in order to reduce over-mutation. This was done by calculating a difference of two scores (i.e., the difference between two computed binding affinities or DDG), one for the mutant and the other of mutant with a back-to-wildtype mutation (FIG. 8, Step 6B). If the mutation was found to provide a DDG of −0.5 RU or more, the mutation was labeled negligible. All such negligible mutations were mutated back to wild-type, creating a number of designs with a range of back to wild type mutations (FIG. 8, Step 6D) including a design with no negligible mutations (FIG. 8, Step 6C). In steps 6E and 6F negative controls are created. In these example, negative control was only the wild-type sequence, so these steps were skipped. Finally, designs with 9 or more mutations were excluded from the hit library (FIG. 8, Step 6G).

For each entry in the hit library, two more rounds of single mutations on the paratope of the designed ligand were attempted to create variability and improve affinity (FIG. 8, Step 6H-6N loop). For each new structure, it is desirable to hold all these criteria simultaneously, for the mutant to be added to the hit library: 1000 Å² or higher change in surface area upon complexation, a DG score less than −8 RU, number of mutations <9 and change in DDG after mutation <−0.5 RU (non-negligible mutation), see FIG. 8, Step 6J-K.

A successive calculation in which the complex was locally perturbed and redocked was carried out (FIG. 8, Step 6I). The new structures were only accepted when the previous set of criteria was simultaneously fulfilled. A final round of mutation was carried out on the redocked set of hits. Again, the same criteria was simultaneously valid for the mutated ligands to be included in the hit library (FIG. 8, Step 6J-K).

At the end of the procedure the redundant designs (e.g., ligands having the same sequences) were excluded. A final visual inspection of all structures was necessary to reduce the final set (FIG. 4, Step 6—Hit Optimization). Hits that lost the original hotspot orientation as a result of redocking and mutating were all excluded (FIG. 8, Step 6P).

For all the steps reported above including mutating residues, optimization and in silico binding affinity estimate, Rosetta modelling package was used, but many of the procedures can be carried out with a variety of modelling packages available on the market or later developed. The thresholds used need to be calibrated for different scoring functions.

Step 7—Mirror Inversion.

The final set of sequences was "mirror inverted" through a simple text operation of converting uppercase sequences to lowercase (FIG. 4, Step 7: Hit Mirror Inversion). Such operation results in converting all L-amino acids to D-amino-acids, and therefore turning the design into a D-protein (for non-chiral glycine g=G). The final peptide library for scaffold 2LJS is presented in Table 2. Noncanonical amino acids have been demarked with the following symbols: "!" stands for D-homophenylalanine and "b" for D-homoleucine.

TABLE 2

| MOLECULE ID | CONTROLS | SEQUENCE |
|---|---|---|
| DP142093 | | rfcpsibkkcrrdsdcpG!cickGnGycG |
| DP141747 | | rfcpnilkkcrrdsdcpG!cickGnGycG |
| DP141748 | | rfcpnilkkcrrdsdcpGecickGnGycG |
| DP141749 | | rfcpsilkkcrrdsdcpG!cickGnGycG |
| DP141750 | | rfcpsilkkcrrdsdcpGecickGnGycG |
| DP141751 | | rfcpsibkkcrrdsdcpG!cickGnGycG |
| DP141752 | | rfcpsibkkcrrdsdcpGecickGnGycG |
| DP141753 | Wild-type | racprilkkcrrdsdcpGecickGnGycG |

Step 8—Synthesis and Screening

Figure 22:
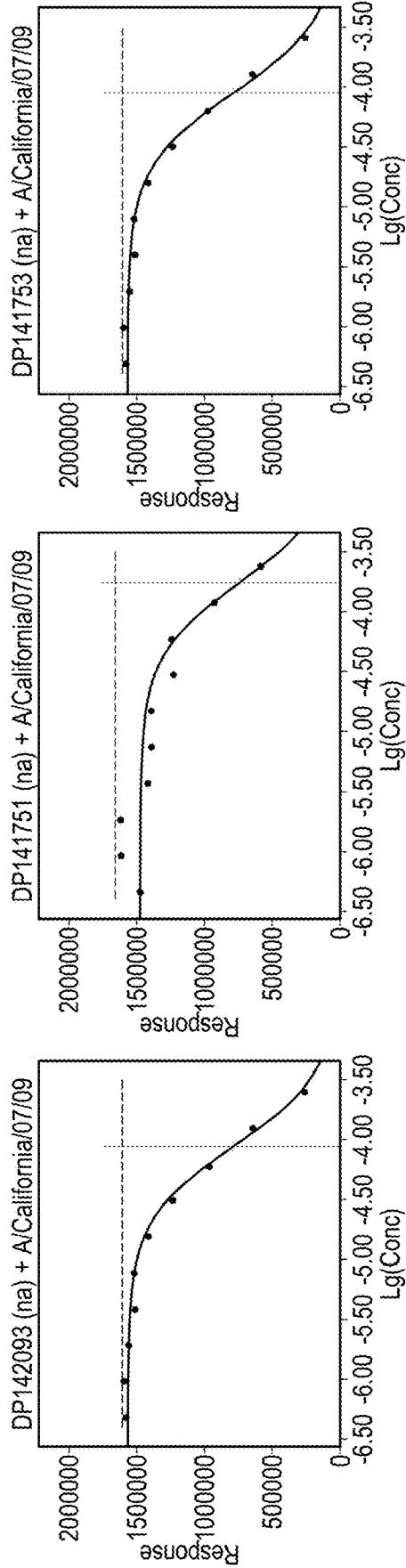
FIG. 22 includes graphs that show competition ELISA results for the optimized HA hit DP142093 (left graphs), optimized hit DP141751 (center graphs) and wild-type DP141753 (right graphs), where upper graphs show competition with HB80.4, and lower graphs are with the head binding antibody CR11054 binding to a non-overlapping epitope.
Figure 22:
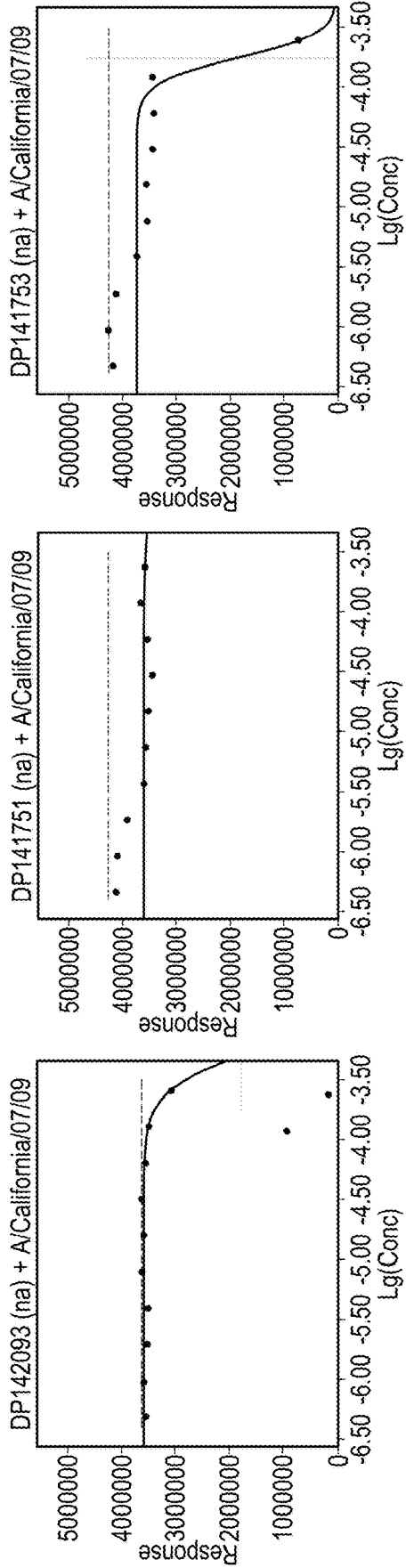

See Example 1 for synthesis and preparation of functional D-proteins for screening. In order to screen for D-protein ligands, binding to the stem epitope of Influenza hemagglutinin, the D-protein ligands were screened in an ELISA assay for competition with the designer protein HB80.4. To show that the binding of the D-protein ligands is specific, non-competing head binding antibody CR11054 was taken along as a control. Results of the competition Elisa are presented in FIG. 22. FIG. 22 shows competition ELISA results for the optimized hit DP142093 (left graphs), optimized hit DP141751 (center graphs) and wild-type DP141753 (right graphs). Upper graphs show competition with HB80.4, and lower graphs are with the head binding antibody CR11054 binding to a non-overlapping epitope. Response is plotted as a function of logarithm of concentration.

From the library of 8 proteins (including negative control), one hit was identified having a pIC50 of 4.1 (88 µM) and showing lack of activity for the negative controls. The negative controls included: Competition of the hit DP142093 with CR11054—antibody binding a non-overlapping epitope; Competition of the wild-type scaffold DP141753 with HB80.4; and Competition of the wild-type scaffold DP141050 with CR11054. Even though the competition for the best compound is weak, the curves in FIG. 22 show clear difference between the designer D-proteins and wild-type. Both DP142093 and DP141751 show a clear S-curve for the competition with the stem binding HB80.4, while no competition (flat curves) for the head binding antibody CR11054. The wild-type protein DP141753 shows no competition until the highest concentration, which is most likely an artifact. In order to have an alternative experimental proof that DP142093 binds in the stem of influenza HA as designed with the in silico approach presented herein, DP142093 and HA have been co-crystallized. The resulting co-crystal structure is depicted in FIG. 23. The figure shows the crystallized complex, next to the co-crystal with the antibody FI6, which the D-protein attempts to mimic. The X-Ray structure confirms the D-protein binds to the same epitope as the template antibody. This example shows that the methodology described herein can be used to design ligands for a target, and that the designed ligands can be constructed and tested to show the physical ligands bind the physical target.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least" and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

The invention claimed is:

1. A method of designing a D-polypeptide ligand that binds with an L-polypeptide target, the L-polypeptide target having an L-polypeptide ligand that has hotspot amino acids with side chains that have binding interactions with the L-polypeptide target to form a target polypeptide complex, the method comprising:
   optionally, mirror inverting in silico the target polypeptide complex;
   isolating in silico hotspot amino acids of the L-polypeptide ligand;
   transforming the side chains of the hotspot amino acids, wherein the transformed side chains retain the binding interactions of the target polypeptide complex;
   inverting the chirality of the hotspot amino acids having transformed side chains, wherein the inverted hotspot amino acids retain the binding interactions of the target polypeptide complex;
   generating in silico a hotspot library comprising a plurality of inverted hotspot amino acid conformations;
   grafting in silico the inverted hotspot amino acids of the hotspot library onto a scaffold polypeptide having the chirality of the inverted hotspot amino acids to form a test polypeptide, wherein the test polypeptide can dock on the L-polypeptide target and retains the binding interactions with the L-polypeptide target;
   mutating the test polypeptide to improve binding with the L-polypeptide target; and synthesizing the mutated test polypeptide as the D-polypeptide ligand.

2. The method of claim 1, comprising an optional mirror inversion applied at any step of the methodology, wherein the inversion is applied to the coordinates of the whole system.

3. The method of claim 1, wherein the hotspot amino acids are amino acids that bind with an epitope of the L-polypeptide target.

4. The method of claim 3, wherein the isolated hotspot amino acids comprise the hotspot amino acid side chains each retained with its carbon-alpha.

5. The method of claim 4, wherein the transformed side chains comprise rotations of the hotspot amino acid side chains that retain the binding interactions of the target polypeptide complex.

6. The method of claim 1, wherein the transformed side chains comprise chemical modifications of the hotspot amino acid side chains that retain the binding interactions of the target polypeptide complex, and wherein the chemical modifications resulting in canonical or non-canonical amino acid side chains.

7. The method of claim 5, comprising:
analyzing interactions between the transformed amino acid side chains and the target to determine whether the transformed amino acid side chains retain the hotspot binding interactions with the target; and selecting the transformed side chains if the hotspot binding interactions with the target are retained; or discarding the transformed side chains if the hotspot binding interactions with the target are not retained.

8. The method of claim 5, comprising:

analyzing interactions between the transformed amino acid side chains and the target to determine whether the transformed amino acid side chains sterically clash with the target; and selecting the transformed side chains if the transformed amino acid side chains do not sterically clash with the target; or discarding the transformed side chains if the transformed amino acid side chains sterically clash with the target.

9. The method of claim 1, comprising:

transforming the inverted hotspot amino acids;

analyzing interactions between the transformed inverted hotspot amino acids and the target to determine whether the transformed inverted hotspot amino acids sterically clashes with the target; and adding the transformed inverted hotspot amino acid to the hotspot library if the transformed inverted hotspot amino acid does not clash with the target; or discarding the transformed inverted hotspot amino acid if the transformed inverted hotspot amino acid clashes with the target.

10. The method of claim 9, comprising:

selecting a transformed inverted hotspot amino acid; and generating a plurality of backbone conformations of the selected transformed inverted hotspot amino acid, each maintaining the same side chain interactions with the target.

11. The method of claim 9, comprising:

selecting a transformed inverted hotspot amino acid; and generating a plurality of amino acid poses in the epitope of the selected transformed inverted hotspot amino acid, each maintaining the same side chain interactions with the target.

12. The method of claim 1, further comprising analyzing the test polypeptide for docking on the L-polypeptide target using conformational sampling techniques and protein-protein docking algorithms.

13. The method of claim 12, wherein the conformational sampling techniques comprise molecular dynamics.

14. The method of claim 1, wherein the step of mutating the test polypeptide comprises:

mutating amino acids of the test polypeptide in the proximity of the L-polypeptide target to improve a predicted binding score;

determining whether the mutated test polypeptide has an improved binding score over the initial test polypeptide; and selecting mutated test polypeptides having the improved binding score as hits.

15. The method of claim 14, comprising:

changing amino acid sequences of the selected hits to optimize the binding score.

16. The method of claim 15, wherein the changing of sequences of the selected hits comprises conformational sampling techniques and algorithms that determine protein-protein docking that are performed on a modeled mutated test polypeptide L-polypeptide target complex.

17. The method of claim 16, wherein the conformational sampling techniques comprise molecular dynamics.

18. The method of claim 14, comprising:

changing the sequence of the selected hits to determine one or more optimal hits having increased binding scores with the L-polypeptide target per number of mutations in the scaffold polypeptide.

19. The method of claim 18, wherein changing the sequence of the selected hits includes one or more of:

mutating one or more amino acids in the selected hits that are different from the scaffold polypeptide back to the amino acids of the scaffold polypeptide;

introducing single amino acid mutations in the proximity of an epitope of the L-polypeptide target or in the direct neighborhood of the hotspot amino acids;

introducing double amino acid mutations in the proximity of an epitope of the L-polypeptide target or in the direct neighborhood of the hotspot amino acids;

introducing triple amino acid mutations in the proximity of an epitope of the L-polypeptide target or in the direct neighborhood of the hotspot amino acids;

mutating amino acids with less water solubility to amino acids with more solubility;

mutating any amino acids in the selected hits with the purpose of forming chemical bonds that result in introduction of cycles;

mutating non-canonical amino acids to canonical amino acids;

mutating canonical amino acids to non-canonical amino acids; and applying conformational sampling techniques and protein-protein docking algorithms.

20. The method of claim 19, comprising:

performing one or more of the changes to the amino acid sequence of the selected hit as one or more iterative loops;

determining whether the one or more changes to the sequence of the selected hit results in an improved binding score with the target per number of mutations in the scaffold polypeptide; and selecting hits with improved binding score with the target per number of mutations in the scaffold polypeptide as optimized hits.

21. The method of claim 20, comprising synthesizing one or more of the optimized hits, wherein the synthesized optimized hits are capable of binding with the L-polypeptide target.

22. The method of claim 20, wherein the optimized hits are D-polypeptide ligands.

23. An in silico method of designing a D-polypeptide ligand that binds with an L-polypeptide target that has an L-polypeptide ligand, the L-polypeptide ligand having hotspot residues with binding interactions with residues of the L-polypeptide target to form a target polypeptide complex, the method comprising:
  isolating a hotspot residue of the L-polypeptide ligand;
  inverting the chirality of the hotspot residue carbon-alpha;
  transforming the inverted hotspot residue to generate a plurality of conformations of the inverted hotspot residue that retain the binding interaction with the residue of the L-polypeptide target; and
  grafting the transformed inverted hotspot residues onto a scaffold polypeptide having one or more D-amino acids to form a test polypeptide that interacts in silico with the residue of the L-polypeptide target mutating the test polypeptide to improve binding with the L-polypeptide target; and synthesizing the mutated test polypeptide as the D-polypeptide ligand.

24. The method of claim 23, wherein the target L-polypeptide complex is mirror inverted in silico to form a D-polypeptide complex.

25. The method of claim 23, wherein the hotspot carbon-alpha is inverted by modifying the hotspot backbone conformation and keeping the hotspot side chain fixed.

26. The method of claim 23, further comprising grafting the transformed inverted hotspot residues onto a plurality of scaffold polypeptides having the chirality of the inverted hotspots to form a plurality of test polypeptides.

27. The method of claim 26, further comprising the steps of:
  docking in silico the test polypeptides to the L-polypeptide target or mirror inversion of the L-polypeptide target; and
  discarding the test polypeptides that do not correctly dock with the L-polypeptide target or mirror inversion of the L-polypeptide target.

28. The method of claim 26, wherein the L-polypeptide target comprises epitope residues and the L-polypeptide ligand comprises paratope residues, and further comprising:
  varying the paratope residues of the test polypeptides to improve docking with the L-polypeptide target.

29. The method of claim 26, wherein the L-polypeptide target comprises epitope residues and the L-polypeptide ligand comprises paratope residues, and further comprising:
  varying the paratope residues of the test polypeptides to improve docking with a mirror inversion of the L-polypeptide target; and
  mirror inverting the improved test polypeptides.

30. A method of making a D-polypeptide ligand that binds to a target L-polypeptide, comprising the steps of:
  providing a target complex comprising a polypeptide ligand and a target polypeptide that have L-chirality, the polypeptide ligand having hotspot amino acids with side chains that have binding interactions with the target polypeptide;
  isolating the hotspot amino acid side chains of the target complex;
  transforming the isolated hotspot amino acid side chains to produce a hotspot side chain library comprising a plurality of transformed hotspot amino acid side chains, wherein the transformed hotspot amino acid side chains retain the binding interactions of the target complex;
  regenerating the amino acid backbones of the transformed hotspot amino acid side chains of the hotspot side chain library with inverted chirality to produce a hotspot library comprising a plurality of inverted hotspot amino acids;
  grafting the inverted hotspot amino acids of the hotspot library to a scaffold polypeptide to form a plurality of test polypeptides, the scaffold polypeptide having the chirality of the inverted hotspot amino acids;
  selecting the test polypeptides that can dock with and that retain the binding interactions with the target polypeptide;
  mutating the test polypeptides to improve binding to the target polypeptide; and
  synthesizing one or more of the mutated test polypeptides as the D-polypeptide ligand.

31. The method of claim 30, further comprising the steps of:
  mirror inverting the target complex before isolating the hotspot amino acid side chains; and
  mirror inverting the mutated test polypeptides before synthesizing the mutated test polypeptide.

\* \* \* \* \*